United States Patent [19]
Bryan

[11] Patent Number: 6,113,886
[45] Date of Patent: *Sep. 5, 2000

[54] BIOLUMINESCENT NOVELTY ITEMS

[75] Inventor: Bruce Bryan, 716 N. Arden Dr., Beverly Hills, Calif. 90210

[73] Assignee: Bruce Bryan, Beverly Hills, Calif.

[ * ] Notice: This patent is subject to a terminal disclaimer.

[21] Appl. No.: 09/447,208

[22] Filed: Nov. 22, 1999

Related U.S. Application Data

[60] Division of application No. 09/135,988, Aug. 17, 1998, which is a continuation-in-part of application No. 08/757,046, Nov. 25, 1996, Pat. No. 5,876,995, which is a continuation-in-part of application No. 08/597,274, Feb. 6, 1996.

[51] Int. Cl.[7] ............................. A61K 7/16; A61K 7/021; A61K 7/035; A61K 7/075; C11D 9/00

[52] U.S. Cl. ............................... 424/49; 424/63; 424/64; 424/69; 424/70.1; 424/70.6; 424/70.7; 424/78.02; 424/94.4; 435/189; 510/119; 510/135; 510/392; 510/481

[58] Field of Search ........................... 435/189; 510/119, 510/135, 392, 481; 424/49, 63, 64, 69, 70.1, 70.6, 70.7, 78.02, 94.4

[56] References Cited

U.S. PATENT DOCUMENTS

| | | | |
|---|---|---|---|
| Re. 31,801 | 1/1985 | Moore, Jr. | 71/29 |
| Re. 32,973 | 7/1989 | Panzarella | 446/16 |
| Re. 35,320 | 8/1996 | Kinnersley et al. | 504/161 |
| D. 340,750 | 10/1993 | Salmon et al. | D21/147 |
| 2,249,608 | 7/1941 | Greene | 221/31.5 |
| 2,541,851 | 2/1951 | Wright | 260/37 |
| 2,579,714 | 2/1951 | Treuthart | 46/8 |
| 2,738,616 | 3/1956 | Windle | 46/1 |
| 3,384,498 | 5/1968 | Ahrabi | 106/38.5 |
| 3,511,612 | 5/1970 | Kennerly et al. | 252/188.3 |
| 3,539,794 | 11/1970 | Rauhut et al. | 240/2.25 |
| 3,565,815 | 2/1971 | Christy | 252/301.3 |
| 3,584,211 | 6/1971 | Rauhut | 240/2.25 |
| 3,597,877 | 8/1971 | Speers | 46/116 |
| 3,634,280 | 1/1972 | Dean et al. | 252/301.3 R |
| 3,649,029 | 3/1972 | Worrell | 273/186 |
| 3,661,790 | 5/1972 | Dean et al. | 252/301.3 R |
| 3,669,891 | 6/1972 | Greenwood et al. | 252/90 |
| 3,727,236 | 4/1973 | Lloyd et al. | 2/51 |
| 3,749,311 | 7/1973 | Hruby | 239/17 |
| 3,773,258 | 11/1973 | Hruby | 239/17 |
| 3,804,654 | 4/1974 | Liu | 106/134 |
| 3,820,715 | 6/1974 | Hamilton | 239/17 |
| 3,838,816 | 10/1974 | Huff et al. | 239/18 |
| 3,843,443 | 10/1974 | Fishman | 195/63 |
| 3,859,125 | 1/1975 | Miller | 117/155 |
| 3,873,485 | 3/1975 | Fichera | 260/29.2 |
| 3,889,880 | 6/1975 | Hruby | 239/18 |
| 3,894,689 | 7/1975 | Billingsley | 239/18 |
| 3,933,488 | 1/1976 | Noguchi et al. | 96/1 |
| 3,939,123 | 2/1976 | Matthews | 260/77.5 |
| 4,002,839 | 1/1977 | Karl et al. | 179/15 BS |
| 4,006,117 | 2/1977 | Merrifield et al. | 260/45.9 |
| 4,016,880 | 4/1977 | Theeuwes et al. | 128/260 |
| 4,021,364 | 5/1977 | Speiser | 252/316 |
| 4,076,547 | 2/1978 | Lester et al. | 106/109 |
| 4,081,394 | 3/1978 | Bartley | 252/91 |
| 4,151,994 | 5/1979 | Stalberger | 273/58 A |
| 4,162,355 | 7/1979 | Tsibris | 526/293 |
| 4,171,412 | 10/1979 | Čoupek et al. | 525/329 |
| 4,172,054 | 10/1979 | Ogawa et al. | 260/8 |
| 4,175,183 | 11/1979 | Ayers | 536/57 |
| 4,177,038 | 12/1979 | Biebricher et al. | 8/192 |
| 4,178,439 | 12/1979 | Ayers et al. | 536/59 |
| 4,179,402 | 12/1979 | Kim et al. | 252/431 |
| 4,180,524 | 12/1979 | Reusser et al. | 585/644 |
| 4,202,905 | 5/1980 | Asai et al. | 426/1 |
| 4,214,674 | 7/1980 | Jones et al. | 222/79 |
| 4,225,581 | 9/1980 | Kreuter et al. | 424/88 |
| 4,229,790 | 10/1980 | Gilliland et al. | 364/200 |
| 4,241,537 | 12/1980 | Wood | 47/77 |
| 4,244,721 | 1/1981 | Gupta et al. | 65/31 |
| 4,246,717 | 1/1981 | Wachtel | 46/6 |
| 4,269,821 | 5/1981 | Kreuter | 424/19 |
| 4,282,287 | 8/1981 | Giese | 428/407 |
| 4,282,678 | 8/1981 | Tsui | 46/175 |
| 4,292,754 | 10/1981 | Lukaszewski | 46/6 |
| 4,313,843 | 2/1982 | Bollyky et al. | 252/188.3 |
| 4,322,311 | 3/1982 | Lim et al. | 252/316 |
| 4,324,683 | 4/1982 | Lim et al. | 252/316 |
| 4,329,332 | 5/1982 | Couvreur et al. | 424/9 |
| 4,334,383 | 6/1982 | Melotti | 46/7 |
| 4,438,869 | 3/1984 | Vierkötter et al. | 222/1 |

(List continued on next page.)

FOREIGN PATENT DOCUMENTS

| | | |
|---|---|---|
| 0025350 | 9/1980 | European Pat. Off. . |
| 0194102 | 9/1986 | European Pat. Off. . |
| 0226979 | 7/1987 | European Pat. Off. . |

(List continued on next page.)

OTHER PUBLICATIONS

"AquaLite®. A calcium–triggered photoprotein," *SeaLite Sciences Technical Report No. 3* (1994).

Anctil et al., Mechanism of photoinactivation and re–activatioon in the bioluminescence system of the ctenophore Mnemiopsis, *Biochem. J.* 22(1): 269–272 (1984).

Apt et al., Evolution of phycobiliproteins, *J. Mol. Biol.* 248: 79–96 (1995).

Assil et al., Sustained release of the antimetabolite cytarabine in the eye multivesicular liposomes, *Arch. Opthalmol.* 105: 400–403 (1987).

(List continued on next page.)

*Primary Examiner*—Robert A. Wax
*Attorney, Agent, or Firm*—Stephanie L. Seidman; Heller Ehrman White & McAuliffe LLP

[57] ABSTRACT

Novelty items that are combinations of articles of manufacture with bioluminescence generating systems and/or fluorescent proteins are provided. These novelty items, which are articles of manufacture, are designed for entertainment, recreation and amusement, and include toys, personal items, such as cosmetics, bath powders, body lotions, gels, powders and creams, toothpastes and other dentifrices, soaps, body paints, and bubble bath, fountains, including liquid "fireworks" and other such jets or sprays or aerosols of compositions that are solutions, mixtures, suspensions, powders, pastes, particles or other formulations.

30 Claims, 9 Drawing Sheets

U.S. PATENT DOCUMENTS

| | | | |
|---|---|---|---|
| 4,439,585 | 3/1984 | Gould et al. | 525/127 |
| 4,485,227 | 11/1984 | Fox | 528/61 |
| 4,507,230 | 3/1985 | Tam et al. | 260/112.5 |
| 4,511,497 | 4/1985 | Ehrlich | 252/542 |
| 4,522,811 | 6/1985 | Eppstein et al. | 514/2 |
| 4,525,306 | 6/1985 | Yajima | 260/428.5 |
| 4,528,180 | 7/1985 | Schaeffer | 424/52 |
| 4,534,317 | 8/1985 | Walsh | 119/51 R |
| 4,542,102 | 9/1985 | Dattagupta et al. | 435/6 |
| 4,556,392 | 12/1985 | Chang | 446/16 |
| 4,562,157 | 12/1985 | Lowe et al. | 435/291 |
| 4,563,726 | 1/1986 | Newcomb et al. | 362/34 |
| 4,565,647 | 1/1986 | Llenado | 252/354 |
| 4,569,981 | 2/1986 | Wenzel et al. | 528/67 |
| 4,581,335 | 4/1986 | Baldwin | 435/172.3 |
| 4,615,488 | 10/1986 | Sands | 239/391 |
| 4,624,976 | 11/1986 | Amano et al. | 524/13 |
| 4,676,406 | 6/1987 | Frischmann et al. | 222/136 |
| 4,681,870 | 7/1987 | Balint et al. | 502/403 |
| 4,687,663 | 8/1987 | Schaeffer | 424/52 |
| 4,697,374 | 10/1987 | Simms | 43/17.5 |
| 4,700,872 | 10/1987 | Keyes et al. | 222/162 |
| 4,700,965 | 10/1987 | Kinbeg | 280/289 |
| 4,701,329 | 10/1987 | Nelson et al. | 426/74 |
| 4,711,659 | 12/1987 | Moore | 71/93 |
| 4,714,682 | 12/1987 | Schwartz | 436/10 |
| 4,717,158 | 1/1988 | Pennisi | 273/58 A |
| 4,733,799 | 3/1988 | Wiskur | 222/79 |
| 4,735,660 | 4/1988 | Cane | 106/203 |
| 4,750,641 | 6/1988 | Chin-Fu | 222/79 |
| 4,762,881 | 8/1988 | Kauer | 525/54.11 |
| 4,764,141 | 8/1988 | D'Andrade | 446/16 |
| 4,765,510 | 8/1988 | Rende | 222/79 |
| 4,767,206 | 8/1988 | Schwartz | 356/73 |
| 4,768,681 | 9/1988 | Dean et al. | 222/79 |
| 4,774,189 | 9/1988 | Schwartz | 436/10 |
| 4,781,647 | 11/1988 | Doane, Jr. | 446/219 |
| 4,784,293 | 11/1988 | Hiroshi | 222/79 |
| 4,789,633 | 12/1988 | Huang | 435/240.2 |
| 4,804,346 | 2/1989 | Sheng | 446/17 |
| 4,804,403 | 2/1989 | Moore | 71/28 |
| 4,808,138 | 2/1989 | von Braunhut | 446/16 |
| 4,808,143 | 2/1989 | Kuo | 446/406 |
| 4,840,597 | 6/1989 | Perez | 446/16 |
| 4,849,213 | 7/1989 | Schaeffer | 424/53 |
| 4,852,801 | 8/1989 | Fuller et al. | 239/12 |
| 4,853,327 | 8/1989 | Dattagupta | 435/6 |
| 4,854,480 | 8/1989 | Shindo | 222/79 |
| 4,861,303 | 8/1989 | Mong-Sheng | 446/17 |
| 4,861,709 | 8/1989 | Ulitzur et al. | 435/6 |
| 4,867,208 | 9/1989 | Fitzgerald et al. | 141/18 |
| 4,867,724 | 9/1989 | Sheng | 446/17 |
| 4,867,908 | 9/1989 | Recktenwald et al. | 252/408.1 |
| 4,871,090 | 10/1989 | Hoffman | 222/81 |
| 4,882,165 | 11/1989 | Hunt et al. | 424/450 |
| 4,885,250 | 12/1989 | Eveleigh et al. | 435/181 |
| 4,891,043 | 1/1990 | Zeimer et al. | 604/20 |
| 4,892,228 | 1/1990 | Yano | 222/79 |
| 4,895,721 | 1/1990 | Drucker | 424/53 |
| 4,900,680 | 2/1990 | Miyazawa et al. | 436/10 |
| 4,908,405 | 3/1990 | Bayer et al. | 525/61 |
| 4,919,140 | 4/1990 | Borgens et al. | 128/422 |
| 4,921,757 | 5/1990 | Wheatley et al. | 428/402.2 |
| 4,923,426 | 5/1990 | Klundt | 446/19 |
| 4,924,358 | 5/1990 | Von Heck | 362/32 |
| 4,927,879 | 5/1990 | Pidgeon | 525/54.1 |
| 4,931,498 | 6/1990 | Pidgeon | 525/54.1 |
| 4,943,255 | 7/1990 | Klundt | 446/15 |
| 4,950,588 | 8/1990 | Dattagupta | 435/6 |
| 4,954,444 | 9/1990 | Eveleigh et al. | 435/181 |
| 4,955,840 | 9/1990 | Moomaw | 446/17 |
| 4,957,464 | 9/1990 | Perez | 446/16 |
| 4,963,117 | 10/1990 | Gualdoni | 446/219 |
| 4,963,368 | 10/1990 | Antrim et al. | 424/498 |
| 4,968,613 | 11/1990 | Masuda et al. | 435/172.3 |
| 4,999,208 | 3/1991 | van Lengerrich | 426/549 |
| 5,004,444 | 4/1991 | Chih | 446/406 |
| 5,004,565 | 4/1991 | Schaap | 252/700 |
| 5,007,924 | 4/1991 | Jekel | 606/234 |
| 5,015,580 | 5/1991 | Christou et al. | 435/172.3 |
| 5,018,449 | 5/1991 | Eidson, II | 102/498 |
| 5,023,181 | 6/1991 | Inouye | 435/189 |
| 5,029,732 | 7/1991 | Wong | 222/79 |
| 5,038,963 | 8/1991 | Pettengill et al. | 222/145 |
| 5,041,042 | 8/1991 | Stein | 446/15 |
| 5,059,417 | 10/1991 | Williams et al. | 424/53 |
| 5,064,095 | 11/1991 | Camerino | 222/99 |
| 5,071,387 | 12/1991 | Pottick | 446/475 |
| 5,078,636 | 1/1992 | Clarke et al. | 446/15 |
| 5,080,623 | 1/1992 | Stein | 446/15 |
| 5,085,853 | 2/1992 | Williams et al. | 424/53 |
| 5,088,950 | 2/1992 | LaFata | 446/19 |
| 5,092,992 | 3/1992 | Crane et al. | 210/198.2 |
| 5,093,240 | 3/1992 | Inouye et al. | 435/69.1 |
| 5,096,807 | 3/1992 | Leaback | 435/6 |
| 5,098,828 | 3/1992 | Geiger et al. | 435/7.72 |
| 5,116,868 | 5/1992 | Chen et al. | 514/546 |
| 5,135,422 | 8/1992 | Bowen | 446/15 |
| 5,139,937 | 8/1992 | Inouye et al. | 435/69.1 |
| 5,141,462 | 8/1992 | Latzel | 446/28 |
| 5,141,467 | 8/1992 | Crosbie | 446/398 |
| 5,141,664 | 8/1992 | Corring et al. | 252/90 |
| 5,150,819 | 9/1992 | Johnson et al. | 222/79 |
| 5,153,231 | 10/1992 | Bouquet et al. | 521/88 |
| 5,156,564 | 10/1992 | Hasegawa | 446/15 |
| 5,158,349 | 10/1992 | Holland et al. | 362/34 |
| 5,162,227 | 11/1992 | Cormier | 435/252.33 |
| 5,166,065 | 11/1992 | Williams et al. | 435/240.1 |
| 5,167,368 | 12/1992 | Nash | 239/17 |
| 5,171,081 | 12/1992 | Pita et al. | 362/36 |
| 5,174,477 | 12/1992 | Schafer | 222/183 |
| 5,177,812 | 1/1993 | DeMars | 2/199 |
| 5,181,875 | 1/1993 | Hasegawa | 446/15 |
| 5,182,202 | 1/1993 | Kajiyama et al. | 435/189 |
| 5,183,428 | 2/1993 | Lin | 446/15 |
| 5,183,429 | 2/1993 | Bitton | 446/73 |
| 5,184,755 | 2/1993 | Brovelli | 222/79 |
| 5,188,837 | 2/1993 | Domb | 424/450 |
| 5,190,762 | 3/1993 | Yarosh | 424/450 |
| 5,192,679 | 3/1993 | Dawson et al. | 435/243 |
| 5,196,318 | 3/1993 | Baldwin et al. | 435/69.1 |
| 5,196,524 | 3/1993 | Gustafson et al. | 536/23.2 |
| 5,206,161 | 4/1993 | Drayna et al. | 435/212 |
| 5,213,089 | 5/1993 | DeLuca | 124/29 |
| 5,213,335 | 5/1993 | Dote et al. | 273/313 |
| 5,219,096 | 6/1993 | Wing | 222/79 |
| 5,219,737 | 6/1993 | Kajiyama et al. | 435/69.1 |
| 5,221,623 | 6/1993 | Legocki et al. | 435/252.3 |
| 5,222,797 | 6/1993 | Holland | 362/34 |
| 5,224,625 | 7/1993 | Holtier | 222/1 |
| 5,224,893 | 7/1993 | Routzong et al. | 446/15 |
| 5,225,212 | 7/1993 | Martin | 424/450 |
| 5,229,285 | 7/1993 | Kajiyama et al. | 435/189 |
| 5,229,531 | 7/1993 | Song | 42/58 |
| 5,234,129 | 8/1993 | Lau | 222/79 |
| 5,238,149 | 8/1993 | Johnson et al. | 222/79 |
| 5,241,944 | 9/1993 | Rappaport | 124/67 |
| 5,244,153 | 9/1993 | Kuhn et al. | 239/587.5 |
| 5,246,631 | 9/1993 | Halbritter | 252/700 |
| 5,246,834 | 9/1993 | Tsuji et al. | 435/7.91 |
| 5,256,099 | 10/1993 | Rudell et al. | 446/473 |
| 5,268,463 | 12/1993 | Jefferson | 536/23.7 |

| | | | |
|---|---|---|---|
| 5,269,715 | 12/1993 | Silveria et al. | 446/16 |
| 5,272,079 | 12/1993 | Yarosh | 435/193 |
| 5,277,913 | 1/1994 | Thompson et al. | 424/450 |
| 5,283,122 | 2/1994 | Huang et al. | 428/402.2 |
| 5,283,911 | 2/1994 | DeMars | 2/209.13 |
| 5,284,272 | 2/1994 | Wei | 222/192 |
| 5,284,274 | 2/1994 | Lee et al. | 222/79 |
| 5,284,646 | 2/1994 | Menz et al. | 424/9 |
| 5,288,018 | 2/1994 | Chikazumi | 239/20 |
| 5,288,623 | 2/1994 | Zenno et al. | 435/69.7 |
| 5,292,032 | 3/1994 | Johnson et al. | 222/79 |
| 5,292,658 | 3/1994 | Cormier et al. | 435/252.33 |
| 5,292,814 | 3/1994 | Bayer et al. | 525/243 |
| 5,296,231 | 3/1994 | Yarosh | 424/450 |
| 5,303,847 | 4/1994 | Cottone | 222/78 |
| 5,304,085 | 4/1994 | Novak | 446/15 |
| 5,305,919 | 4/1994 | Johnson et al. | 222/79 |
| 5,306,631 | 4/1994 | Harrison et al. | 435/172.3 |
| 5,310,421 | 5/1994 | Shapero et al. | 106/208 |
| 5,322,191 | 6/1994 | Johnson et al. | 222/79 |
| 5,322,464 | 6/1994 | Sanford | 446/15 |
| 5,323,492 | 6/1994 | DeMars | 2/203.13 |
| 5,326,303 | 7/1994 | D'Andrade | 446/407 |
| 5,328,603 | 7/1994 | Velander et al. | 210/198.2 |
| 5,330,906 | 7/1994 | Kajiyama et al. | 435/189 |
| 5,334,640 | 8/1994 | Desai et al. | 524/56 |
| 5,337,956 | 8/1994 | Crutcher | 239/27 |
| 5,339,987 | 8/1994 | D'Andrade | 222/79 |
| 5,341,538 | 8/1994 | Banome | 15/210.1 |
| 5,342,607 | 8/1994 | Josephson | 424/9 |
| 5,343,849 | 9/1994 | Steer | 124/72 |
| 5,343,850 | 9/1994 | Steer | 124/64 |
| 5,346,418 | 9/1994 | Arad | 446/91 |
| 5,346,455 | 9/1994 | Volkert | 493/335 |
| 5,348,392 | 9/1994 | Bouquet et al. | 366/162 |
| 5,348,507 | 9/1994 | McGhie et al. | 446/16 |
| 5,351,931 | 10/1994 | Houben et al. | 249/141 |
| 5,352,432 | 10/1994 | Menz et al. | 424/9 |
| 5,352,448 | 10/1994 | Bowersock et al. | 424/438 |
| 5,352,598 | 10/1994 | Kajiyama et al. | 435/189 |
| 5,353,378 | 10/1994 | Hoffman et al. | 395/2.81 |
| 5,360,010 | 11/1994 | Applegate | 128/745 |
| 5,360,142 | 11/1994 | Stern et al. | 222/79 |
| 5,360,726 | 11/1994 | Raikhel | 435/172.3 |
| 5,360,728 | 11/1994 | Prasher | 435/189 |
| 5,362,865 | 11/1994 | Austin | 536/24.1 |
| 5,363,984 | 11/1994 | Laird | 221/24 |
| 5,366,108 | 11/1994 | Darling | 222/1 |
| 5,366,402 | 11/1994 | Rudell et al. | 446/16 |
| 5,366,881 | 11/1994 | Singh et al. | 435/177 |
| 5,368,518 | 11/1994 | Hitchcock | 446/329 |
| 5,370,278 | 12/1994 | Raynie | 222/175 |
| 5,373,832 | 12/1994 | D'Andrade | 124/69 |
| 5,373,833 | 12/1994 | D'Andrade | 124/69 |
| 5,373,975 | 12/1994 | Husted | 222/394 |
| 5,374,534 | 12/1994 | Zomer et al. | 435/8 |
| 5,374,805 | 12/1994 | DiFranco | 219/121 |
| 5,377,656 | 1/1995 | Lewinski et al. | 124/65 |
| 5,381,928 | 1/1995 | Lee et al. | 222/79 |
| 5,381,956 | 1/1995 | Robinson et al. | 239/22 |
| 5,383,100 | 1/1995 | Kikos | 362/34 |
| 5,383,684 | 1/1995 | Smath | 281/29 |
| 5,388,285 | 2/1995 | Belniak | 4/507 |
| 5,389,033 | 2/1995 | Rauch | 446/473 |
| 5,389,449 | 2/1995 | Afeyan et al. | 428/523 |
| 5,390,086 | 2/1995 | Holland | 362/34 |
| 5,393,256 | 2/1995 | Mitchell et al. | 446/15 |
| 5,393,580 | 2/1995 | Ma et al. | 428/29 |
| 5,396,408 | 3/1995 | Szczech | 362/397 |
| 5,397,014 | 3/1995 | Aydt | 220/269 |
| 5,397,609 | 3/1995 | Chapman | 428/17 |
| 5,397,827 | 3/1995 | Armstrong et al. | 215/6 |
| 5,398,972 | 3/1995 | Todaro | 283/67 |
| 5,399,122 | 3/1995 | Slater | 472/51 |
| 5,400,698 | 3/1995 | Savage | 99/439 |
| 5,401,773 | 3/1995 | Noel | 514/547 |
| 5,402,836 | 4/1995 | Hasper et al. | 141/364 |
| 5,403,221 | 4/1995 | Savage | 446/45 |
| 5,403,750 | 4/1995 | Braatz et al. | 436/531 |
| 5,405,056 | 4/1995 | Mills | 222/136 |
| 5,405,206 | 4/1995 | Bedol | 401/7 |
| 5,405,905 | 4/1995 | Darr | 524/420 |
| 5,405,958 | 4/1995 | VanGermert | 544/71 |
| 5,407,391 | 4/1995 | Monroe et al. | 472/61 |
| 5,407,691 | 4/1995 | Przelomski et al. | 426/249 |
| 5,410,962 | 5/1995 | Collier | 101/375 |
| 5,411,427 | 5/1995 | Nelson et al. | 446/71 |
| 5,411,730 | 5/1995 | Kirpotin et al. | 424/322 |
| 5,412,085 | 5/1995 | Allen et al. | 536/24.1 |
| 5,412,118 | 5/1995 | Vermeer et al. | 549/417 |
| 5,413,332 | 5/1995 | Montgomery | 273/58 |
| 5,413,454 | 5/1995 | Movesesian | 414/729 |
| 5,415,151 | 5/1995 | Fusi et al. | 124/56 |
| 5,416,017 | 5/1995 | Burton et al. | 435/240.2 |
| 5,416,193 | 5/1995 | Desai | 530/334 |
| 5,416,927 | 5/1995 | Spangrud | 2/195.1 |
| 5,418,155 | 5/1995 | Cormier et al. | 435/189 |
| 5,419,458 | 5/1995 | Mayer | 222/79 |
| 5,419,558 | 5/1995 | Jones | 273/153 |
| 5,419,728 | 5/1995 | Dallara | 446/15 |
| 5,421,583 | 6/1995 | Gluck | 273/293 |
| 5,422,075 | 6/1995 | Saito et al. | 422/52 |
| 5,422,266 | 6/1995 | Cormier et al. | 435/252.3 |
| 5,424,216 | 6/1995 | Nagano et al. | 436/116 |
| 5,427,320 | 6/1995 | Mark et al. | 239/587.5 |
| 5,429,351 | 7/1995 | Hanson | 273/58 |
| 5,432,081 | 7/1995 | Jefferson | 435/252.3 |
| 5,432,623 | 7/1995 | Egan et al. | 359/15 |
| 5,435,010 | 7/1995 | May | 2/67 |
| 5,435,787 | 7/1995 | Ratcliffe | 472/56 |
| 5,435,937 | 7/1995 | Bell et al. | 252/301.18 |
| 5,436,392 | 7/1995 | Thomas et al. | 800/205 |
| 5,439,139 | 8/1995 | Brovelli | 222/79 |
| 5,439,170 | 8/1995 | Dach | 239/18 |
| 5,448,984 | 9/1995 | Brovelli | 124/69 |
| 5,451,347 | 9/1995 | Akhavan-Tafti et al. | 252/700 |
| 5,451,683 | 9/1995 | Barrett et al. | 548/302.7 |
| 5,455,357 | 10/1995 | Herrmann et al. | 548/147 |
| 5,457,182 | 10/1995 | Wiederrecht | 530/402 |
| 5,458,931 | 10/1995 | Mankes | 428/14 |
| 5,460,022 | 10/1995 | Parsons | 70/456 |
| 5,462,469 | 10/1995 | Lei | 446/15 |
| 5,464,758 | 11/1995 | Gossen et al. | 435/69.1 |
| 5,470,881 | 11/1995 | Charlton et al. | 514/588 |
| 5,472,140 | 12/1995 | Versaw et al. | 239/24 |
| 5,476,779 | 12/1995 | Chen et al. | 435/240.1 |
| 5,478,267 | 12/1995 | McDonald et al. | 446/15 |
| 5,478,490 | 12/1995 | Russo et al. | 252/153 |
| 5,478,501 | 12/1995 | Rau | 252/547 |
| 5,480,094 | 1/1996 | Fuller et al. | 239/17 |
| 5,480,334 | 1/1996 | Wilson et al. | 446/46 |
| 5,482,719 | 1/1996 | Guillet et al. | 424/486 |
| 5,484,589 | 1/1996 | Salganik | 424/94.2 |
| 5,484,723 | 1/1996 | Zenno et al. | 435/189 |
| 5,486,455 | 1/1996 | Stults | 435/6 |
| 5,489,742 | 2/1996 | Hammer et al. | 800/2 |
| 5,510,099 | 4/1996 | Short et al. | 424/9.2 |
| 5,512,421 | 4/1996 | Burns et al. | 435/320.1 |
| 5,547,486 | 8/1996 | Detrick et al. | 71/28 |
| 5,553,853 | 9/1996 | Sackitey | 273/236 |
| 5,554,035 | 9/1996 | Gooch | 434/297 |
| 5,604,123 | 2/1997 | Kazami et al. | 435/189 |
| 5,625,048 | 4/1997 | Tsien et al. | 536/23.4 |
| 5,632,957 | 5/1997 | Heller et al. | 422/68.1 |

| | | | |
|---|---|---|---|
| 5,671,998 | 9/1997 | Collet | 362/101 |
| 5,730,321 | 3/1998 | McAllister et al. | 222/1 |
| 5,770,371 | 6/1998 | Thompson | 435/6 |
| 5,776,681 | 7/1998 | Virta et al. | 435/6 |
| 5,777,079 | 7/1998 | Tsien et al. | 530/350 |
| 5,795,737 | 8/1998 | Seed et al. | 435/69.1 |
| 5,804,387 | 9/1998 | Cormack et al. | 435/6 |
| 5,876,995 | 3/1999 | Bryan | 435/189 |

FOREIGN PATENT DOCUMENTS

| | | |
|---|---|---|
| 0245093 | 11/1987 | European Pat. Off. . |
| 0246174 | 11/1987 | European Pat. Off. . |
| 0302819 | 2/1989 | European Pat. Off. . |
| 0386691 | 9/1990 | European Pat. Off. . |
| 0387355 | 9/1990 | European Pat. Off. . |
| 0418049 | 3/1991 | European Pat. Off. . |
| 0540064 | 5/1993 | European Pat. Off. . |
| 0713089 | 5/1996 | European Pat. Off. . |
| 2292595 | 6/1976 | France . |
| 2674223 | 9/1992 | France . |
| 3935974 | 5/1991 | Germany . |
| 3030678 | 2/1991 | Japan . |
| 7241192 | 9/1995 | Japan . |
| 1105927 | 3/1968 | United Kingdom . |
| 2235931 | 3/1991 | United Kingdom . |
| 2288232 | 10/1995 | United Kingdom . |
| 8603840 | 7/1986 | WIPO . |
| 8703304 | 6/1987 | WIPO . |
| 9001542 | 2/1990 | WIPO . |
| 9117286 | 11/1991 | WIPO . |
| 9204577 | 3/1992 | WIPO . |
| 9215673 | 9/1992 | WIPO . |
| 9404918 | 3/1994 | WIPO . |
| 9418342 | 8/1994 | WIPO . |
| 9425855 | 11/1994 | WIPO . |
| 9507463 | 3/1995 | WIPO . |
| 9512808 | 5/1995 | WIPO . |
| 9518853 | 7/1995 | WIPO . |
| 9521191 | 8/1995 | WIPO . |
| 9525798 | 9/1995 | WIPO . |
| 9607917 | 3/1996 | WIPO . |
| 9711094 | 3/1997 | WIPO . |
| 9728261 | 8/1997 | WIPO . |
| 9729319 | 8/1997 | WIPO . |
| 9814605 | 4/1998 | WIPO . |
| 9826277 | 6/1998 | WIPO . |
| 9949019 | 9/1999 | WIPO . |

OTHER PUBLICATIONS

Badminton et al., Nucleoplasmin–targeted aequorin provides evidence for a nuclear calcium barrier, *Expt. Cell Research* 216(1): 236–243 (1995).

Baldwin et al., Cloning of the luciferase structural genes from *Vibro harveyi* and expression of bioluminescene in *Escherichia coli*, *Biochemistry* 23: 3663–3667 (1984).

Baldwin et al., Applications of the cloned bacterial luciferase genes LUXA and LUXB to the study of transcriptional promoters and terminators, *Bioluminescence and Chemiluminescence: Basic Chemistry and Analytical Applications*, pp. 373–375 (1981).

Batra et al., Insertion of constant region domains of human $IgG_1$ Into CD4–PE40 increases its plasma half–life, *Mol. Immunol.* 30: 379–386 (1993).

Becvar et al., A thermodynamic explanation for the kinetic differences observed using different chain length aldehydes in the in vitro bacterial bioluminescent reaction, in *Bioluminescence and Chemiluminescence: New Perspectives*, pp. 147–155, 180–185, John Wiley & Sons (1981).

Belas et al., Bacterial bioluminescene: Isolation and expression of the luciferase genes from *Vibrio harveyi*, *Science* 218: 791–793 (1982).

Berg et al., Peptide synthesis on polystyrene–grafted polyethylene sheets, *Pept., Proc. Eur. Pept. Symp.*, 20th, Jung et al. (Eds.), pp. 196–198 (1989).

Berg et al., Long–chain polystyrene–grafted polyethylene film matrix: a new support for solid–phase peptide synthesis, *J. Am. Chem. Soc. 111:* 8026–8027 (1989).

Berg et al., Polystyrene–grafted polyethylene: Design of film and felt matrices for solid–phase peptide synthesis, *Innovation Perspect. Solid Phase Synth. Collect. Pap.*, Int. Symp., 1st, Epton (ed.), pp. 453–459 (1990).

Bhalerao et al., Cloning of the cpcE and cpcF genes from *Synechococcus* sp. PCC 6301 and their inactivation in *Synechoccoccus* sp. PCC 7942, *Plant Molec. Biol.* 26: 313–326 (1994).

Blinks et al., Multiple forms of the calcium–sensitive bioluminescent protein aequorin, *Fed. Proc. 1435:* 474 (1975).

Bondar et al., Cadmium–induced luminescence of recombinant photoprotein obelin, *Biochim. Biophys. Acta 1231:* 29–32 (1995).

Bunnin et al., The combinatorial synthesis and chemical and biological evaluation of a 1,4–benzodiazepine library, *Proc. Natl. Acad. Sci. U.S.A.* 91:4708 (1994).

Button et al., Aequorin–expressing mammalian cell lines used to report $Ca^{2+}$ mobilization, *Cell Calcium* 14(9):663–671 (1993).

Butz et al., Immunization and affinity purification of antibodies usig resin–immobilized lysine–branched synthetic peptides, *Peptide Res.* 7: 20–23 (1994).

Campbell et al., Formation of the $Ca^{2+}$–activated photoprotein obelin from apo–obelin and mRNA inside human neutrophils, *Biochem. J.* 252(1):143–9 (1988).

Casadei et al., Characterization of a chimeric aequorin molecule expressed in myeloma cells, *J. Bioluminescence & Chemiluminescence* 4(1): 346–350 (1989).

Chalfie, Green fluorescent protein, *Photochemistry and Photobiology*, 62(4):651–656 (1995).

Charbonneau et al., "Amino acid sequence of the calcium––dependent photoprotein aequorin," *Biochem.* 24:6762–6771 (1985).

Charbonneau H, and Cormier M. Ca2 +–induced bioluminescence in *Renilla reniformis*. Purification and Characterization of a calcium–triggered luciferin–binding protein. *J. Biol. Chem.* 254(3):769–80 (1979).

Chemical Abstract #115(5)43510b (citing, Japanese Patent Application No. JP 3–30678 Osaka).

Chen et al., "Analogous" organic synthesis of small–compound libraries: validation of combinatorial chemistry in small molecule synthesis, *J. Am. Chem. Soc.* 116:2661, (1994).

Cohn et al., Nucleotide sequence of the luxa gene of *Vibrio harveyi* and the complete amino acid sequence of the α subunit of bacterial luciferase, *J. Biol. Chem.* 260: 6139–6146 (1985).

Cohn D et al. Cloning of the *Vibrio harveyi* luciferace genes: use of a synthetic oligonucleotide probe. *Proc. Natl. Acad. Sci. USA* 80(1):120–123 (1983).

Cormier et al., Evidence for similar biochemical requirements for bioluminescene among the coelenterates, *J. Cell Physiol.* 81: 291–298 (1972).

Cormier "Renilla and Aequorea biolunimescence" pp 225–233 in *Bioluminescence and Chemiluminescence. Basic Chemistry and Analytical Applications.* DeLuca et al eds, Academic Press 1981.

Crescitelli, Adaptations of visual pigments to the photic environment of th edeep sea, *J. Exptl. Zool. Supp. 5:* 66–75 (1991).

Database EMBL Nucleotide and Protein Sequences, AC=AF025844, Co–reporter vector pRL–Null, complete sequence, abstract, (1997).

de Wet et al., "Cloning of firefly luciferase cDNA and the expression of active luciferase in *Escherichia coli,*" *Proc. Natl. Acad. Sci. USA 82:*7870–7873 (1985).

de Wet et al., "Cloning and expression of the firefly luciferase gene in mammalian cells," *Bioluminescence and Chemiluminescence. Basic Chemistry and Analytical Applications,* DeLuca et al., eds., pp. 368–371, Academic Press (1981).

de Wet et al., "Cloning firefly luciferase," *Meth. Enzymol. 133:*3–14 (1986).

Delagrave et al., Red–shifted excitation mutants of the green fluorescent protein, *Bio/Technology* 13(2):151–154 (1995).

Derwent #009443237 WPI Acc. No. 93–136754/17 (citing, Japanese Patent Application No. JP 5064583, published Mar. 19, 1993).

Derwent #010423635 WPI Acc. No. 95–324955/42 (citing, Japanese Patent Application No. JP 7222590, published Aug. 22, 1995).

Derwent # 007778737 WPI Acc. No. 89–043849/06 (citing Japanese Patent Application No. JP 63317079, published Dec. 26, 1988).

Derwent #009227258 WPI Acc. No. 92–354680/43 (citing, Japanese Patent Application No. JP 4258288, published Sep. 14, 1993).

DeWitt et al., Diversomers: an approach to nonpeptide, nonoligomeric chemical diversity, *Proc. Natl. Acad. Sci. USA 90:* 6909–6913 (1993).

DIALOG Abstract 001641802, citing: FR 2292595.
DIALOG Abstract 008629835, citing: DE 3935974 A1.
DIALOG Abstract 007325798, citing: EP 246174 A1.
DIALOG Abstract 007775837, citing: EP 302819 A1.
DIALOG Abstract 009182471, citing: FR 2674223 A1.
DIALOG Abstract 002042687, citing: JP 7241192.

Düzgunes et al., Fusion of phospholipid vesicles induced by divalent cations and protons; modulation by phase trasitions, free fatty acids, monovalent cations, and polyamines, *Cell Fusion, Ch. 11 Divalent Cations and Protons,* Sowers, A.E. (ed.) pp. 241–267 (1984).

Ehrig et al., Green–fluorescent protein mutants with altered fluorence excitationspectra, *FEBS Letters* 367:163–166 (1995).

Eichler et al., Identification of substrate–analog trypsin inhibitors through the screening of synthetic peptide combinatorial libraries, *Biochemistry 32:* 11035–11041 (1993).

Ellens et al., pH–induced Destabilization of phosphatidylethanolamine–containing liposomes: Role of bilayer contact, *Biochemistry,* 23: 1532–1538 (1984).

Engebrecht et al., "Techniques for cloning and analyzing bioluminescence genes from marine bacteria," *Meth. Enzymol. 133:*83–99, 234 (1986).

Engebrecht et al., Bacterial bioluminescence: Isolation and genetic analysis of functions from *Vibrio fischeri, Cell 32:* 773–781 (1983).

Engebrecht et al., Identification of genes and gene products necessary for bacterial bioluminescene, *Proc. Natl. Acad. Sci. USA 81:* 4154–4158 (1984).

Fairchild et al., Oligomeric structure, enzyme kinetics, and substrate specificity of the phycocyanin α subunit phycocyanobilin lyase, *J. Biol. Chem. 269(12):* 8686–8694 (1994).

Frackman et al., "Cloning, organization, and expression of the bioluminescence genes of *Xenorhabdus luminescens,"J. Bacteriol. 127(10):*5767–5773 (1990).

Fratamico et al., Construction and characterization of *Escherichia coli* 0157:H7 strains expressing firefly luciferase and green fluorescent protein and their use in survival studies, *J of Food Protection* 60(10):1167–1173 (1997).

Gast et al., Separation of a blue fluorescence protein from bacterial luciferase. Biochem. Biophys. Res. Commun. 80(1): 14–21 (1978).

Gautier et al., Alternate determination of ATP and NADH with a single bioluminescence–based fiber–optic sensor, Fifth International Conference on Solid State Sensors and Actuators and Eurosensors III, Montreux, Switzerland, Jun. 25–30, 1989.

Gesztes et al., Topical anesthesia of the skin by liposome–encapsulated tetracaine, *Anesthesia Analg. 67:* 1079–1081 (1988).

Gilbert et al., Expression of genes involved in phycocyanin biosynthesis following recovery of *Synechococcus* PCC 6301 from nitrogen starvation, and the effect of gabaculine on cpcBa transcript levels, *FEMS Microbiol. Lett.* 140: 93–98 (1996).

Glazer, Phycobilisomes: structure and dynamics, *Ann. Rev. Miocrobiol. 36:* 173–98 (1982).

Goldmacher et al., Photoactivation of toxin conjugates, *Bioconj. Chem. 3:*104–107 (1992).

Goto et al., Preliminary report on the pink–colored Cypridina luciferse, a natural model of the luciferin–luciferase complex, in *Bioluminescence and Chemiluminescence. Basic Chemistry and Analytical Applications,* DeLuca et al., eds., pp. 203–207, Academic Press (1981).

Grentzmann et al., A dual–luciferase system for studying recoding signals, *RNA* 479–486 (1998).

Guyomard et al., Integration and germ line transmission of foreign genes microinjected into fertilized trout eggs, *Biochimie 71:*857–863 (1989).

Hart et al., *Renilla reniformis* bioluminescence: luciferase–catalyzed production of nonradiating excited states from luciferin analogues and elucidation of the excited states species involved in energy transfer to Renilla green fluorescent protein, *Biochemistry 18:* 2204–2210, (1979).

Hastings, Bioluminescence, in *Cell Physiol.: Source Book,* Sperelakis, ed., pp. 665–681, Academic Press (1995).

Hastings, *Bioluminescence and Chemiluminescence. Basic Chemistry and Analytical Applications,* DeLuca et al., eds., pp. 343–349, Academic Press (1981).

Hazum et al., A photocleavalble protecting group for the thiol function of cysteine, *Pept., Proc. Eur. Pept. Symp.,* 16th, Brunfeldt, K (Ed), pp. 105–110 (1981).

Heim et al., Engineering green fluorescent protein for improved brightness, longer wavelengths and fluorescence resonance energy transfer, *Current Biology* 6(2):178–182 (1996).

Hermanson et al., *Immobilized Affinity Ligand Techniques,* Chaps. 1 and 2, Academic Press, Inc. (1992).

Hill et al., *Bioluminescence and Chemiluminescence. Basic Chemistry and Analytical Applications,* DeLuca et al., eds., pp. 396–399, Academic Press (1981).
Hiller–Adams et al., The visual pigments of four deep–sea crustacean species, *J. Comp. Physiol. A 163:* 63–72 (1988).
Hori et al., Structure of native *Renilla reniformis* luciferin, *Proc. Natl. Acad. Sci. USA 74:* 4285–4287 (1977).
Hori et al., Renilla luciferin as the substrate for calcium induced photoprotein bioluminescence. Assignment of luciferin plutomers in aequorin and mnemiopsin, *Biochemistry 14:* 2371–2376, (1975).
Houmard et al., Genes encoding core components of the phycobilisome in cyanobacterium *Calothrix* sp. strain PCC 7601: occurrence of a multigene family, *J. Bacteriol. 170(12):* 5512–5321 (1988).
Illarionov et al., Sequence of the cDNA encoding the $Ca^{2+}$–activated photoprotein obelin from the hydroid poly *Obelia longissima, Gene 153:*273–274 (1995).
*Immobilized Enzyme, Antigens, Antibodies and Peptides. Preparation and Characterization,* Marcel Dekker, Inc., N.Y., Howard H. Weetall (ed.) (1975).
*Immobilized Biochemicals and Affinity Chromatography, Advances in Experimental Medicine and Biology,* vol. 42, ed. R. Dunlap, Plenum Press, N.Y. (1974).
Inoue et al., Electroporation as a new technique for producing transgenic fish, *Cell Differ. Devel. 29:*123–128 (1990).
Inouye et al., "Overexpression and purification of the rcombinant $Ca^{2+}$—binding protein, apoaequorin," *J. Biochem. 105(3):*473–477 (1989).
Inouye et al., "Expression of apoaequorin complementary DNA in *Escherichia coli," Biochem. 25:*8425–8429 (1986).
Inouye et al., "Imaging of luciferase secretion from transformed Chinese hamster ovary cells," *Proc. Natl. Acad. Sci. USA 89:*9584–9587 (1992).
Inouye et al., Monitoring gene expression in Chinese hamster ovary cells using secreted apoaequorin, *Analyt. Biochem. 201(1):* 114–118 (1992).
Inouye et al., *Jap. Soc. Chem. Lett.*141–144 (1975).
Inouye et al., "Cloning and sequence analysis of cDNA for the luminescent protein aequorin," *Proc. Natl. Acad. Sci. USA 82:*3154–3158 (1985).
Johnson, *Luminescence, Narcosis, and Life in the Deep Sea,* pp. 51–56, Vantage Press.
Johnson et al., "Introduction to the Cypridina system," *Methods in Enzymology. Bioluminescence and Chemiluminescence. 57:*331–349 (1978).
Karatani et al., A blue fluorescent protein from a yellow–e-mitting luminous bacterium, *Photochem. Photobiol. 55(2):* 293–299 (1992).
Karp et al., *Bioluminescence and Chemiluminescence. Basic Chemistry and Analytical Applications,* DeLuca et al., eds., pp. 360–363, Academic Press (1981).
Kendall et al., Changes in free calcium in the endoplasmic reticulum of living cells detected using targeted aequorin, *Anal. Biochem. 22(1):* 173–81 (1994).
Kennedy and Cabral, Immobilized Enzymes, in *Solid Phase Biochemistry, Analytical and Synthetic Aspects,* Scouten, Ed., 7:253–391 (1983).
Kent et al., Preparation and properties of tert–butyloxycarbonylaminocayl–4–(oxymethyl) phenylac-etamidomethyl–(Kel F–g styrene) resin, an insoluble, noncrosslinked support for solid phase peptide synthesis, *Israel J. Chem. 17:* 243–247 (1978).
Kim et al., Preparation of multivesicular liposomes, *Biochim. Biophys. Acta. 728:* 339–348 (1983).
Kleine et al., Lipopeptide–polyoxyethylene conjugates as mitogens and adjuvants, *Immunobiology 190:* 53–66 (1994).
Knight et al., Imaging calcium dynamics in living plants using semi–synthetic recombinant aequorins, *J. Cell Biol. 121(1):*83–909 (1993).
Knight et al., Transgenic plant aequorin reports the effects of touch and cold–shock and elicitors on cytoplasmic calcium, *Nature 352(6335):* 524–526 (1991).
Koch et al., The oxidative cleavability of protein cross–linking reagents containing organoselenium bridges, *Bioconj. Chem. 1:* 296–304 (1990).
Kohama et al., Molecular weight of the photoprotein aequorin, *Biochemistry 10:* 4149–4152 (1971).
Kronick, The use of phycobiliproteins as fikuorescent labels in immunoassay, *J. Immunolog. Meth. 92:* 1–13 (1986).
Kurose et al., Bioluminescence of the $Ca^{2+}$–binding photoprotein aequorin after cysteine modification, *Proc. Natl. Acad. Sci. USA 86(1):* 80–84 (1989).
Kusumi et al., Liposomes that can be disintegrated by photo–irradiation, *Chemistry Letters* 433–436 (1989).
Leach et al., Commercially available firefly luciferase reagents, in *Methods in Enzymology. Bioluminescence and Chemiluminescence Part B 133:*51–69, Academic Press (1986).
Lee et al., *Methods in Enzymology. Bioluminescence and Chemiluminescence. 57:*226–233, DeLuca, ed., pp. 372–375, Academic Press (1978).
Legocki et al., Bioluminescence in soybean root nodules: Demonstration of a general approach to assay gene expression in vivo by using bacterial luciferase, *Proc. Natl. Acad. Sci. USA 81:* 9080–9084 (1986).
*Liposome Technology, Targeted Drug Delivery and Biological Interaction,* vol. III, G. Gregoriadis (ed.), CRC Press, Inc., 1984.
Liu et al., A cyanidium caldarium Allophycocyanin β subunit gene, *Plant Physiol. 103:*293–294 (1993).
Lorenz et al., Isolation and expression of a cDNA encoding *Renilla reniformis* luciferase, *Proc. Natl. Acad. Sci. USA 88:* 4438–4442 (1991).
Lucas et al., Coelenterazine is a superoxide anion–sensitive chemiluminescent probe: its usefulness in the assay of respiratory burst in neutrophils, *Analyt. Biochem. 206(2):*273–277 (1992).
Matthews et al., Purification and properties of *Renilla reniformis* luciferase, *Biochemistry,* 16: 85–91 (1977).
McElroy et al., The colors of bioluminescence: Role of enzyme and substrate structure, in *Molecular Architecture in Cell Physiology,* pp. 63–80, Hayashi et al., eds., Prentice–Hall, Inc., Englewood Cliffs, NJ (1966).
Merrifield, Solid–phase peptide synthesis. III. An improved synthesis of bradykinin, *Biochemistry 3(9):* 1385–1390 (1964).
Mezei et al., Liposomes—A selective drug delivery system for the topical route of administration, *Life Sci. 26:* 1473–1477 (1980).
Mezei et al., Liposomes—A selective drug delivery system for the topical route of administration: Gel dosage form, *J. Pham. Pharmacol. 34:* 473–474 (1981).
Mitchell et al., Preparation of aminomethyl–polystyrene resin by direct aminomethylation, *Tetra. Lett.,* 42: 3795–3798 (1976).
Mitchell et al., A new synthetic route to tert–butyloxycarbonylaminoacyl–4–(oxymethyl)phenylace tamidomethyl–resin, an improved support for solid–phase peptide synthesis, *J. Org. Chem. 43:* 2845–2852 (1978).

Mitra et al., Fluorescence resonance energy tranfer between blue–emitting and red–shifted excitation derivatives of the green fluorescent protein, *Gene* 73(1):13–17 (1996).

Miyamoto et al., Cloning and expression of the genes from the bioluminescent system of marine bacteria, *Meth. Enzymol. 133:*70–81 (1986).

*Molecular Biology of the Gene,* 4th Edition, 1987, ed. Watson et al. The Benjamin/Cummings Pub. co. p. 224.

Mosbach, K and Mattiasson, B. Multistep enzyme systems. *Methods in Enzymology 44:*453–478 (1976).

Mosbach, K. Immobilized Enzymes. *Methods in Enzymology 44:*3–7 (1976).

Mosbach, AMP and NAD as 'general ligands', *Affinity Techniques. Enzyme Purification: Part B. Methods in Enzymology,* vol. 34, W. B. Jakoby, et al. (eds.), Acad. Press, N.Y. (1974).

Mosbach et al. Immobilization of enzymes to various acrylic copolymers. *Methods in Enzymology 44:*53–65 (1976).

Nakajima–Shimada et al., Monitoring of intracellular calcium in *Saccharomyces cerevisiae* with an apoaequorin cDNA expression system, *Proc. Natl. Acad. Sci. USA 88(15)*: 6878–6882 (1991).

Nicoli et al., Bacterial luciferase: The hydrophobic environment of the reactive sulfhydryl, *J. Biol. Chem. 249:* 2393–2396 (1974).

O'Day et al., *Aristostomias scintillans (Malacostiedae)*: a deep sea fish with visual pigments apparently adapted to its own bioluminescence, *Vision Res. 14:*545–550 (1974).

Ozato et al., Production of transgeniuc fish: introduction and expression of chicken γ–crystalline gene in medaka embryos, *Cell Differ. Devel. 19:*237–244 (1986).

Padwa and Carls, Thermal rearrangement of allyl substituted 2H–azirines to 3 azabicylo [3.1.0] hex–2–enes, *J. Org. Chem. 41:* 180–182 (1976).

Padwa et al. Photoelimination of a β–Keto Sulfide with a Low–Lyingπ–π* Triple State *J. Org. Chem. 36(23)*:3550–3552 (1971).

Patel, Liposomes as a controlled–release system, *Biochem. Soc. Trans. 13:* 513–516 (1985).

Pidgeon, Solid Phase membrane mimetics: Immobilized artificial membranes, *Enzyme Microbiology Technology 12:*149–150 (1990).

Pierce Catalog, Immuno Technology Catalog & Handbook (1992–1993).

Pilot et al., Cloning and sequencing of th egenes encoding the α and β subunits of C–phycocyanin from the cyanobacterium *Agmenellum quadruplicatum, Proc. Natl. Acad. Sci. USA 81:* 6983–6987 (1984).

Powers et al., Protein purification by affinity binding to unilamellar vesicles, *Biotechnol. Bioeng. 33:* 173–182 (1989).

Prasher et al., Primary structure of the *Aequorea victoria* green–fluorescent protein, *Gene 111:*229–233 (1992).

Prasher et al., Isolation and expression of a cDNA coding for aequorin, the $Ca^{2+}$—activated photoprotein from *Aequorea victoria, Meth. Enzymol. 133:*288–297 (1986).

Prasher et al., *Bioluminescence and Chemiluminescence. Basic Chemistry and Analytical Applications,* DeLuca et al., eds., pp. 365–367, Academic Press (1981).

Prasher et al., Cloning and expression of the cDNA coding for aequorin, a bioluminescent calcium–binding protein, *Biochem. Biophys. Res. Commun. 126(3)*:1259–1268 (1985).

Prasher et al., Sequence comparisons of complementary DNAs encoding aequorin isotypes, *Biochem. 26:*1326–1332 (1987).

Prendergast et al., Chemical and physical properties of aequorin and the green fluorescent protein isolated from *Aequorea forskålea, Biochemistry 17:* 3448–53 (1978).

Rivera et al., AquaLite® Streptavidin for supersentive TSH assays in microtiter plates and coated tubes, *SeaLite Sciences Technical Report No. 6.*

Rizzuto et al., Rapid changes of mitochondrial $Ca^{2+}$ revealed by specifically targeted recombinant aequorin, *Nature 358(6384)*: 325–327 (1992).

Rokkones et al., Microinjection and expression of a mouse metallothionein human growth hormone fusion gene in fertilized salmonid eggs, *J. Comp. Phyiol.B 158:*751–758 (1989).

Romoser et al., Detection in living cells of Ca2+–dependent changes in the fluorescence emission of an indicator composed of two green fluorescent protein variants liked by a calmodulin–binding sequence, *J. of Biolog. Chem.* 272(20):13270–13274 (1997).

Rutter et al., Involvement of MAP kinase in insulin signalling revealed by non–invasive imaging of luciferase gene expression in single living cells, *Current Biology 5(8)*: 890–9 (1995).

Sandalova, Some notions about structure of bacterial luciferase, obtained by analysis of amino acid sequence, and study of monoclonal antibodies binding, In *Biological Luminescence, Proceedings of International School,* 1st, ed., Jezowska–Trzebiatowska et al., World Science (1990).

Saran et al., Intracellular free calcium level and its response to cAMP stimulation in developing Dictyostelium cells transformed with jellyfish apoaequorin cDNA, *FEBS Lett. 337(1)*: 43–7 (1994).

Sedlak et al., Bioluminescent Technology for Reagents, Diagnostics and Toxicology, *Genetic Engineering News,* Sep. 15, 1995.

Senter et al., Novel photocleavable protein crosslinking reagents and their use in the preparation of antibody–toxin conjugates, *Photochem. Photobiol. 42:* 231–237 (1985).

Sgoutas et al., AquaLite® bioluminescence assay of thyrotropin in serum evaluated, *Clin. Chem. 41(11)*:1637–1643 (1995).

Sherf et al., Dual–luciferase reporter assay: an advanced co–reporter technology integrating firefly and Renilla luciferase assays, *Promega Notes* 57:2–5 (1996).

Sheu et al., Measurement of intracellular calcium using bioluminescent aequorin exposed in human cells, *Analyt. Biochem. 209(2)*: 343–347 (1993).

Shimomura et al., Resistivity to denaturation of the apoprotein of aequorin and reconstitution of the luminescent photoprotein from the partially denatured apoprotein, *Biochem J. 199:*825–828 (1981).

Shimomura et al., Recombinant aequorin and recombinant semi–synthetic aequorins. Cellular $Ca^{2+}$ ion indicators, *Biochem. J. 270(2)*: 309–12 (1990).

Shimomura et al. Reactions involved in bioluminescence systems of limpet (*Latia neritoides*) and luminous bacteria. *Proc. Natl. Acad. Sci. USA 69(8)*:2086–2089 (1972).

Shimomura, Biolouminescence in the sea: photoprotein systems [Review], Symposia of the *Society for Experimental Biology 39:* 351–372 (1985).

Shimomura et al., Properties and reaction mechanism of the bioluminescence system of the deep–sea shrimp *Oplophorus gracilorostris, Biochem 17(6)*: 994–998 (1978).

Shimomura et al., Properties of the bioluminescent protein aequorin, *Biochemistry 8:* 3991–3997 (1969).

Shimomura O, and Johnson F. Structure of the light–emitting moiety of aequorin. *Biochemistry 11(9)*:1602–1608 (1972).

Shimomura O, and Johnson F. The structure of Latia luciferin. *Biochemistry 7(5)*:1734–1738 (1968).

Shimomura et al., Semi–synthetic aequorins with improved sensitivity to $Ca^{2+}$ ions, *Biochem. J. 261(3)*: 913–920 (1989).

Shimomura et al., Extraction, purification and properties of a aequorin, a bioluminescent protein from the luminous hydromedusan, Aequorea, *J. Cell. Comp. Physiol. 59:* 233–238 (1962).

Shimomura et al., Peroxidized coelenterazine, the active group in the photoprotein aequorin, *Proc. Natl. Acad. Sci. USA 75(6)*: 2611–5 (1978).

Shimomura et al., Regeneration of the photoprotein aequorin, *Nature 256:* 236–238 (1975).

Shimomura et al., Semi–synthetic aequorin. An improved tool for the measurement of calcium ion concentration, *Biochem. J. 251(2)*: 405–10 (1988).

Shimomura et al., The relative rate of aequorin regeneration from apoaequorin and coelenterazine analogues, *Biochem. J. 296(Pt. 3)*: 549–551 (1993).

Smith et al., Bioluminescent immunoassays using streptavidin and biotin conjugates of recombinant aequorin, reprinted from *American Biotechnology Laboratory,* Apr. 1995.

Smith et al., Kinetically inert Co(III) linkage through an engineered metal binding site: specific orientation of recombinant human papillomavirus type 16 E7 protein on a solid support, *Methods: A Companion to Methods in Enzymology,* 4: 73–78, (1992).

Spurlok et al., A fine structure study of the anthocodium in *Ranilla mulleri, J. of Cell Biology* 64:15–28 (1975).

Stability of AquaLite®: lyophilized and in solution, *SeaLite Sciences Technical Report No. 8* (1994).

Stephenson et al., Studies on the luminescent response of the $Ca^{2+}$–activated photoprotein, obelin, *Biochim. Biophys. Acta 678:* 65–75 (1981).

Stewart and Young, Laboratory techniques in solid phase peptide synthesis, *Solid Phase Peptide Synthesis,* 2d Ed., Pierce Chemical Co., pp. 53–73 (1984).

Straubinger et al., Endocytosis of liposomes and intracellular fate of encapsulated molecules: Encounter with a low pH compartment after internalization in coated vesicles, *Cell 32:* 1069–1079 (1983).

Strubinger et al., pH–sensitive liposomes mediate cytoplasmic delivery of encapsulated macromolecules, *FEBS Letters 179:* 148–154 (1985).

Sucholeiki, Solid–phase photochemical C–S Bond cleavage of thioethers—A New approach to the solid–phase production of non–peptide molecules, *Tetrahedron Lttrs. 35*:7307 (1994).

Thompson et al., *Vargula hilgendorfii* luciferase: a secreted reporter enzyme for monitoring gene expression in mammalian cells, *Gene 96:*257–262 (1990).

Thompson et al., Cloning and expression of cDNA for th eluciferase from the marine ostracod *Vargula hilgendorfi xi, Proc. Natl. Acad. Sci. USA 86:* 6567–6571 (1989).

Tsuji et al., Mechanism of the enzyme–catalyzed oxidation of Cypridina and firefly luciferins studied by means of $^{17}O_2$ and $H_2{}^{18}O^1$, *Biochem. Biophys.Res. Commun. 74(2):*606–613 (1977).

Tsuji et al., Some properties of luciferase from the bioluminescent crustacean, *Cypridina hilgendorfii, Biochem. 13(25)*:5204–5209 (1974).

Tsuji et al., Site–specific mutagenesis of the calcium–binding photoprotein aequorin, *Proc. Natl. Acad. Sci. USA 83:*8107–8111 (1986).

Tsuji, Cypridina luciferin and luciferase, *Meth. Enzymol. 57:*364–372 (1978).

Vedejs et al., A method for mild photochemical oxidation: Conversion of phenacyl sulfides into carbonyl compounds, *J. Org. Chem. 49:* 573–575 (1984).

Vysotski et al., Luminescence of $Ca^{2+}$–activated photoprotein obelin initiated by NaOCl and $MnCl_2$, *J. Biolumin. Chemilumin. 8:*301–305 (1993).

Vysotski et al., $Mn^{2+}$–activated luminescence of the photoprotein obelin, *Arch. Bioch. Biophys. 316:*92–93 (1995).

Wang, Solid phase synthesis of protected peptides via photolytic cleavage of the α–methylphenacyl ester anchoring linkage, *J. Org. Chem. 41:* 3258–3261 (1976).

Ward et al., Extraction of Renilla–type luciferin from the calcium–activated photoproteins aequorin, mnemiopsin, and berovin, *Proc. Natl. Acad. Sci. USA 72:* 2530–2534 (1975).

Ward et al., An energy transfer protein in coelenterate bioluminescence, *J. Biol. Chem. 254:* 781–788 (1979).

Ward, General Aspects of Bioluminescence, in *Chemi– and Bioluminescence,* Burr, ed., Marcel Dekker, Inc., New York.

Watanabe et al., Bunding of murine monoclonal antibodies to the active and inactive configurations of aequorin, *FEBS Lett. 246(1–2)*: 73–77 (1989).

Watkins et al., Requirement of the C–terminal proline residue for stability of the $Ca^{(2+)}$–activated photoprotein aequorin, *Biochem. J. 293(Pt. 1)*: 181–185 (1993).

Welches et al., Active center studies on bacterial luciferase: Modification of the enzyme with 2,4–dinitrofluorobenzene, *Biochemistry 20:* 512–517 (1981).

Wienhausen et al., Luciferases from different species of fireflies are antigenically similar, *Photochem. Photobiol. 42:* 609–611 (1985).

Wohlrab et al., Penetration Kinetics of liposomal hydrocortisone in human skin, *Dermatologica 174:* 18–22 (1987).

Wong, Conjugation of proteins to solid matrices, *Chemistry of Protein Conjugation and Cross Linking,* 12:295–317 (1993).

Xu et al., A bioluminiscence resonance energy transfer (BRET) system: application to interacting circadian clock proteins, *Proc. Natl. Acad. Sci. U.S.A. 96:*151–156 (1999).

Yatvin et al., Temperature– and pH–sensitive liposomes for drug targeting, *Meth. Enzymol. 149:* 77–87 (1987).

Yen et al., Synthesis of water–soluble copolymers containing photocleavabel bonds, *Makromol. Chemistry 190:* 69–82 (1989).

Ziegler et al., Active center studies on bacterial luciferase: Locations of the protease labile regions and the reactive cysteinyl residue in the primary structure of the α subunit, *Bioluminescence and Chemiluminescence. Basic Chemistry and Analytical Applications,* DeLuca et al., eds., pp. 376–377, Academic Press (1981).

Zuckermann et al. Efficient Method for the Preparation of Peptoids [Oligo(N–substituted glycines)] by Submonomer Solid–Phase Synthesis *J. Am. Chem. Soc. 114:*10646 (1992).

Zuckermann et al., Discovery of nanomolar ligands for 7–transmembrane G–protein–coupled receptors from a diverse N–(substituted) glycine peptoid library, *J. Med. Chem. 37:* 2678–2685 (1994).

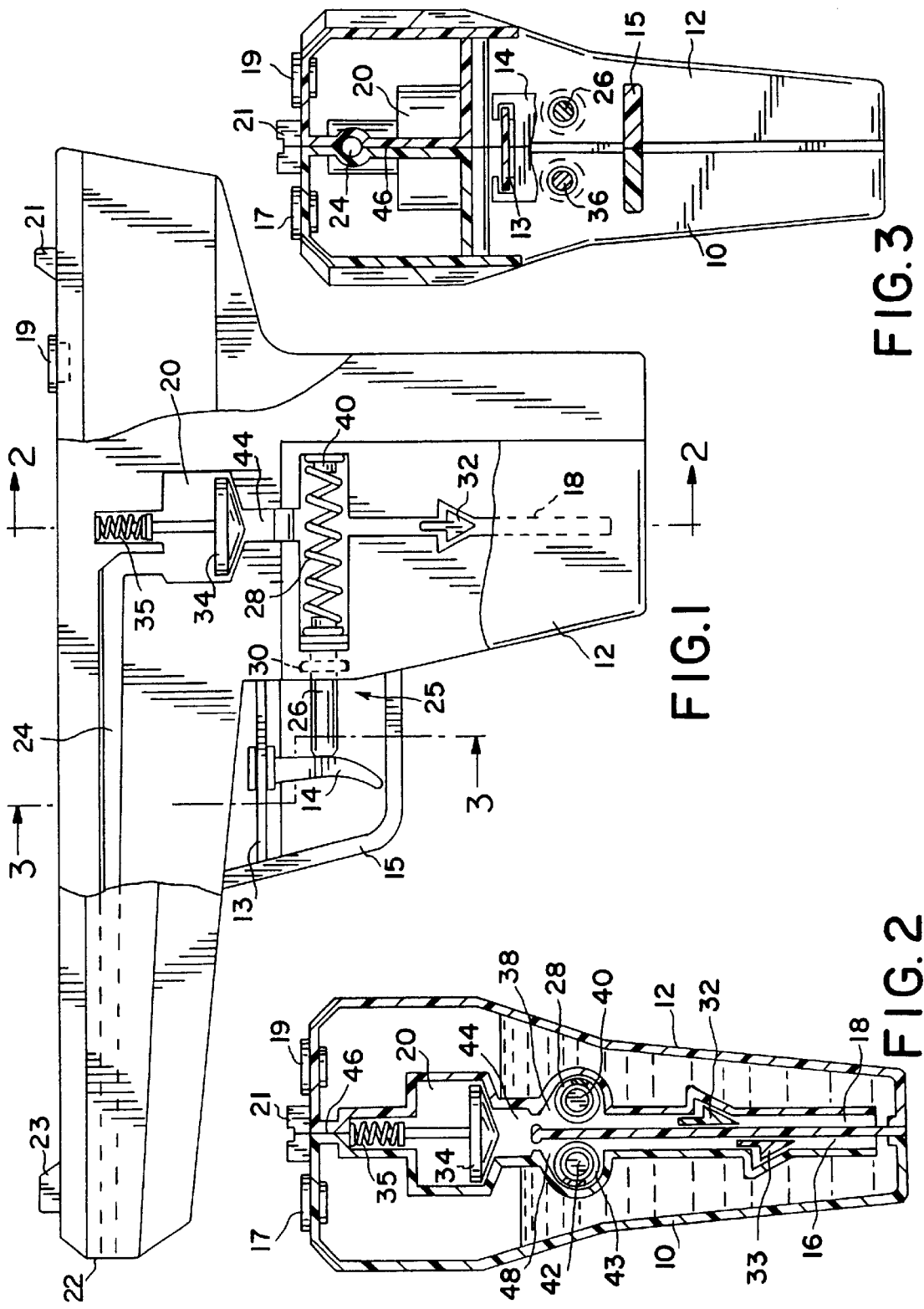

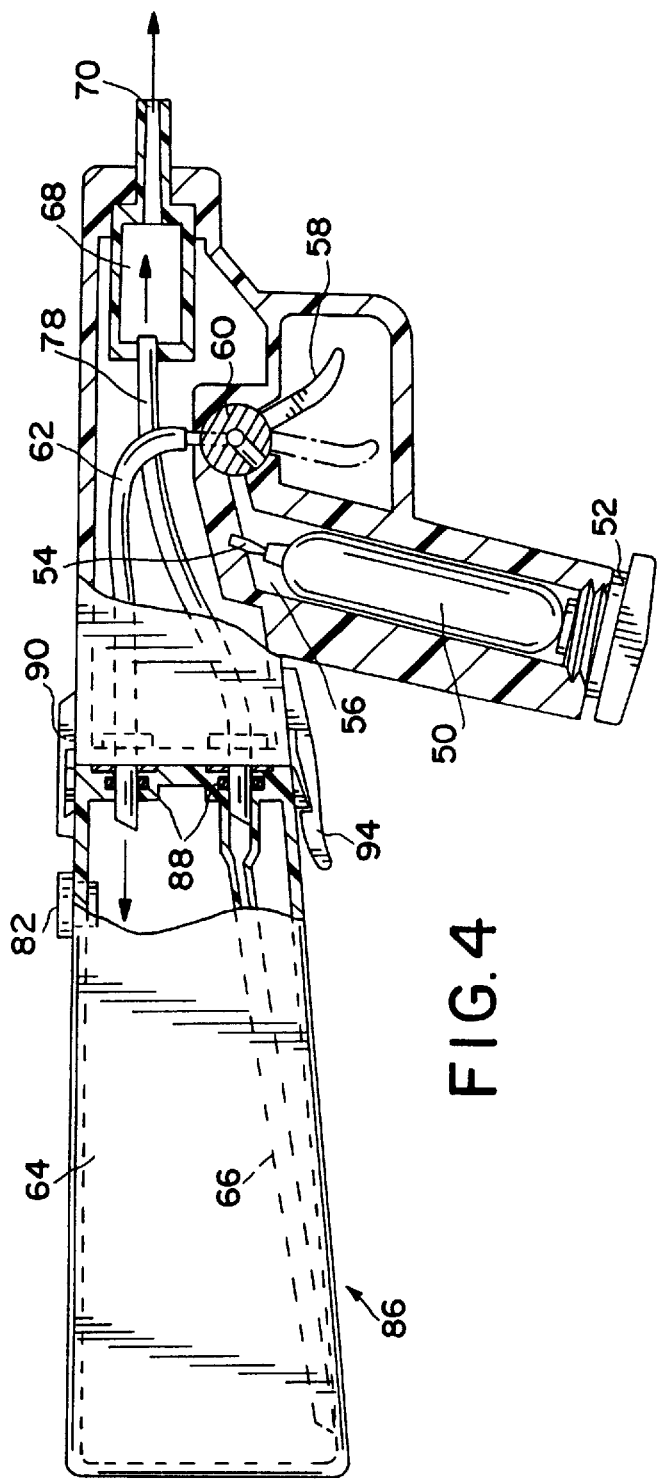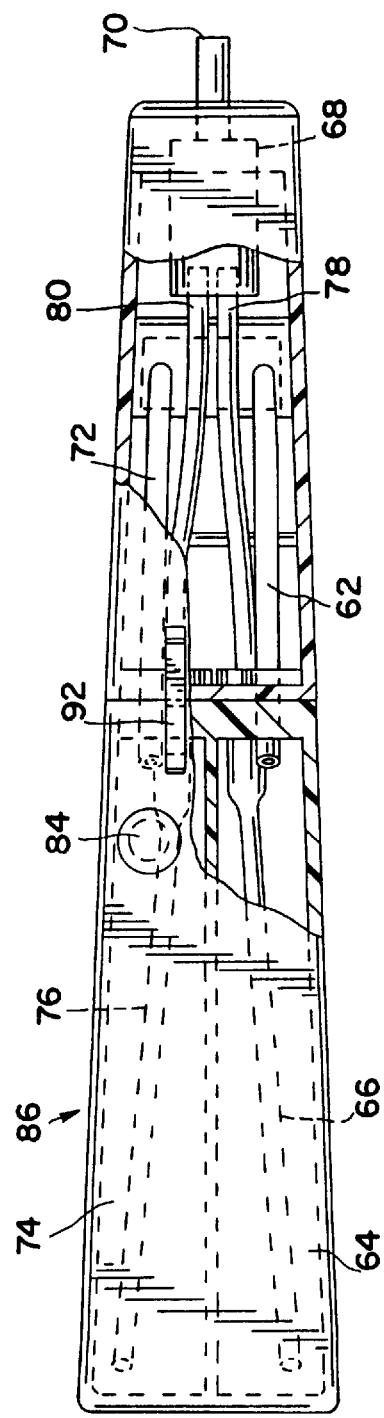
FIG. 4
FIG. 5

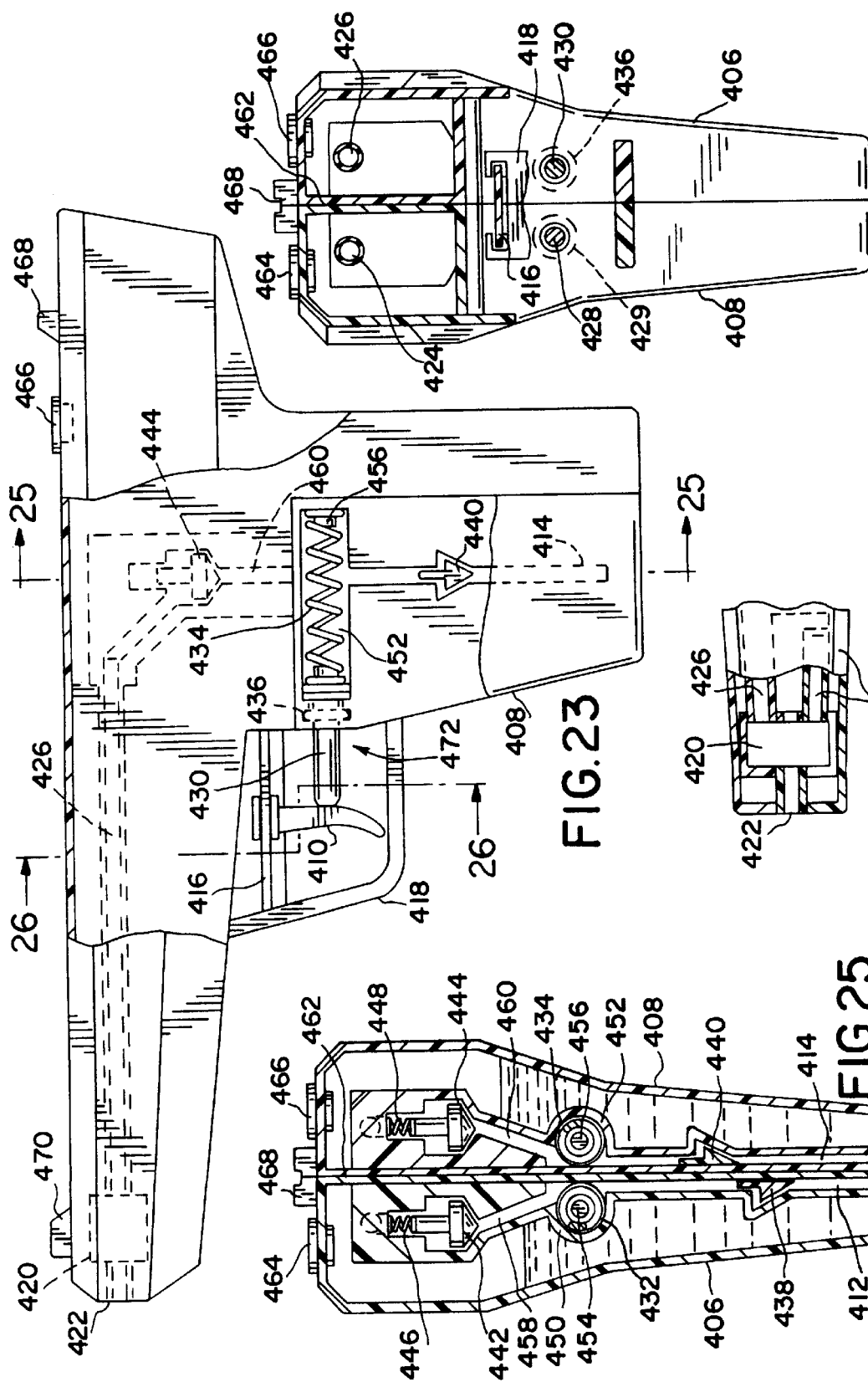

BIOLUMINESCENT NOVELTY ITEMS

RELATED APPLICATIONS

This application is a divisional of U.S. application Ser. No. 09/135,988 to Bruce Bryan, filed Aug. 17, 1998, entitled "BIOLUMINESCENT NOVELTY ITEMS." This application is also continuation-in-part of U.S. application Ser. No. 08/757,046, now U.S. Pat. No. 5,876,995, to Bruce Bryan, filed Nov. 25, 1996, entitled "BIOLUMINESCENT NOVELTY ITEMS." This application is also a continuation-in-part of U.S. application Ser. No. 08/597,274, now allowed, to Bruce Bryan, filed Feb. 6, 1996, entitled "BIOLUMINESCENT NOVELTY ITEMS".

U.S. Pat. No. 09/135,988 is a continuation-in-part of U.S. application Ser. No. 08/757,046, which is a continuation-in-part of U.S. application Ser. No. 08/597,274. The subject matter of each of U.S. application Ser. Nos. 09/135,988, 08/597,274 and 08/757,046 is herein incorporated in its entirety by reference thereto. This application is also related to provisional application Ser. Nos. 60/079,624 and 60/089,367. The disclosures of each of the above noted applications and provisional applications is incorporated herein by reference thereto.

FIELD OF INVENTION

The present invention relates to systems for producing bioluminescent light, and to combinations of the systems with articles of manufacture including toys, textiles, food and beverages, to produce novelty items. By virtue of the combination, the novelty items glow or produce or expel a bioluminescent composition. Also, provided are compositions, encapsulated bioluminescence generating reagents, and methods for producing the bioluminescence.

BACKGROUND OF THE INVENTION

Luminescence is a phenomenon in which energy is specifically channeled to a molecule to produce an excited state. Return to a lower energy state is accompanied by release of a photon (hγ). Luminescence includes fluorescence, phosphorescence, chemiluminescence and bioluminescence. Bioluminescence is the process by which living organisms emit light that is visible to other organisms. Luminescence may be represented as follows:

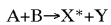

where X* is an electronically excited molecule and hγ represents light emission upon return of X* to a lower energy state. Where the luminescence is bioluminescence, creation of the excited state derives from an enzyme catalyzed reaction. The color of the emitted light in a bioluminescent (or chemiluminescent or other luminescent) reaction is characteristic of the excited molecule, and is independent from its source of excitation and temperature.

An essential condition for bioluminescence is the use of molecular oxygen, either bound or free in the presence of a luciferase. Luciferases, are oxygenases, that act on a substrate, luciferin, in the presence of molecular oxygen and transform the substrate to an excited state. Upon return to a lower energy level, energy is released in the form of light [for reviews see, e.g., McElroy et al. (1966) in *Molecular Architecture in Cell Physiology,* Hayashi et al., eds., Prentice-Hall, Inc., Englewood Cliffs, N.J., pp. 63–80; Ward et al., Chapter 7 in *Chemi-and Bioluminescence,* Burr, ed., Marcel Dekker, Inc. NY, pp.321–358; Hastings, J. W. in (1995) *Cell Physiology: Source Book,* N. Sperelakis (ed.), Academic Press, pp 665–681; *Luminescence, Narcosis and Life in the Deep Sea,* Johnson, Vantage Press, NY, see, esp. pp. 50–56].

Though rare overall, bioluminescence is more common in marine organisms than in terrestrial organisms. Bioluminescence has developed from as many as thirty evolutionarily distinct origins and, thus, is manifested in a variety of ways so that the biochemical and physiological mechanisms responsible for bioluminescence in different organisms are distinct. Bioluminescent species span many genera and include microscopic organisms, such as bacteria [primarily marine bacteria including Vibrio species], fungi, algae and dinoflagellates, to marine organisms, including arthropods, mollusks, echinoderms, and chordates, and terrestrial organism including annelid worms and insects.

Bioluminescence, as well as other types of chemiluminescence, is used for quantitative determinations of specific substances in biology and medicine. For example, luciferase genes have been cloned and exploited as reporter genes in numerous assays, for many purposes. Since the different luciferase systems have different specific requirements, they may be used to detect and quantify a variety of substances. The majority of commercial bioluminescence applications are based on firefly [*Photinus pyralis*] luciferase. One of the first and still widely used assays involves the use of firefly luciferase to detect the presence of ATP. It is also used to detect and quantify other substrates or co-factors in the reaction. Any reaction that produces or utilizes NAD(H), NADP(H) or long chain aldehyde, either directly or indirectly, can be coupled to the light-emitting reaction of bacterial luciferase.

Another luciferase system that has been used commercially for analytical purposes is the Aequorin system. The purified jellyfish photoprotein, aequorin, is used to detect and quantify intracellular $Ca^{2+}$ and its changes under various experimental conditions. The Aequorin photoprotein is relatively small [~20 kDa], nontoxic, and can be injected into cells in quantities adequate to detect calcium over a large concentration range [$3 \times 10^{-7}$ to $10^{-4}$ M].

Because of their analytical utility, many luciferases and substrates have been studied and well-characterized and are commercially available [e.g., firefly luciferase is available from Sigma, St. Louis, Mo., and Boehringer Mannheim Biochemicals, Indianapolis, Ind.; recombinantly produced firefly luciferase and other reagents based on this gene or for use with this protein are available from Promega Corporation, Madison, Wis.; the aequorin photoprotein luciferase from jellyfish and luciferase from Renilla are commercially available from Sealite Sciences, Bogart, Ga.; oelenterazine, the naturally-occurring substrate for these luciferases, is available from Molecular Probes, Eugene, Oreg.]. These luciferases and related reagents are used as reagents for diagnostics, quality control, environmental testing and other such analyses. These reagents have not been used in connection with entertainment and recreation for the glow, illumination and color produced upon generation of bioluminescence.

Thus, it is an object herein to exploit bioluminescence for use as a recreational product in combination with articles of manufacture to produce novelty items, including toys, personal items, foods, fountains, beverages, coating compositions, such as paints and inks, textiles, including clothing, toy cigarettes, fish food, particularly for feeding transgenic fish that express a luciferase, jewelry and other such items. It is also an object herein to provide such combinations and to provide means for producing and using such combinations.

SUMMARY OF THE INVENTION

Systems and apparatus for generating bioluminescence, and combinations of these systems and apparatus with inanimate articles of manufacture to produce novelty items are provided. These novelty items, which are articles of manufacture, are designed for entertainment, recreation and amusement, and include, but are not limited to: toys, particularly squirt guns, toy cigarettes, toy "Halloween" eggs, footbags and board/card games; finger paints and other paints, slimy play material; textiles, particularly clothing, such as shirts, hats and sports gear suits, threads and yarns; bubbles in bubble making toys and other toys that produce bubbles; balloons; figurines; personal items, such as bath powders, body lotions, gels, powders and creams, nail polishes, make-up, toothpastes and other dentifrices, soaps, body paints, and bubble bath; items such as inks, paper; foods, such as gelatins, popcorn, icings and frostings; fish food containing luciferins and transgenic fish, particularly transgenic fish that express a luciferase; plant food containing a luciferin or luciferase, preferably a luciferin for use with transgenic plants that express luciferase; and beverages, such as beer, wine, champagne, soft drinks, and ice cubes and ice in other configurations; fountains, including liquid "fireworks" and other such jets or sprays or aerosols of compositions that are solutions, mixtures, suspensions, powders, pastes, particles or other suitable form.

Thus, the novelty items provided herein include but are not limited to: textiles that glow, ink that glows, paints, particularly fingerpaints, that glow, paper products that glow, toys, particularly reloadable squirt guns that eject a bioluminescent fluid, dolls and dummies with internal organs or parts that glow, figurines and novelty items that glow; toy "cigarettes" that produce glowing "smoke" upon exhalation, toy eggs with glowing yolks and/or whites, toy footbags that glow and toy board and card games with glowing parts, such as glowing cards, dice, game boards, etc.; foods and beverages that glow, soapy compositions for blowing bubbles that produce bubbles that glow, bubble bath compositions that produce bubbles that glow, fountains that expel glowing fluid, bioluminescent "fireworks", sparklers, magic-wand toys, and numerous other such items. Food containing a luciferin for use with plants and animals that express luciferase, such as transgenic fish, then when fed a food containing an appropriate substrate glow, is also contemplated herein.

Bioluminescence is advantageously used in combination with such novelty items because it can be generated using reagents that are nontoxic, noncorrosive and nonstaining. Bioluminescence is also advantageously used because it can be sustained to provide a glow that lasts, if desired, from minutes up to hours.

Any article of manufacture that can be combined with a bioluminescence-generating system as provided herein and thereby provide entertainment, recreation and/or amusement, including use of the items for recreation or to attract attention, such as for advertising goods and/or services that are associated with a logo or trademark is contemplated herein. Such uses may be in addition to or in conjunction with or in place of the ordinary or normal use of such items. As a result of the combination, the items glow or produce, such as in the case of squirt guns and fountains, a glowing fluid or spray of liquid or particles. The novelty in the novelty item derives from its bioluminescence.

The preferred bioluminescence-generating reactions are performed by adding oxygen (or water containing oxygen) or calcium ions or other appropriate metal ion to luciferin and luciferase mixtures using apparatus and systems as described herein. Apparatus, systems and substrates for generating the bioluminescence are provided. The systems include matrix materials that are coated with bioluminescence generating reagents, capsular vehicles containing the reagents and single chamber and multiple chamber apparatus containing the reagents. The matrix materials are used, for example, in the fabrication of clothing items and also in the loading cartridges described herein.

Methods and compositions for producing bioluminescence in combination with the novelty items are also provided. Micro- and macro-capsular vehicles containing bioluminescence generating reagents are provided. The capsular vehicles are capsules, such as liposomes, isolated endosomes, isolated vacuoles, gelatin capsules, and other such delivery vehicles, and the apparatus include vessels, and single chamber, dual chamber and three chamber or more apparatus. These vehicles encapsulate bioluminescence generating system reagents, and typically contain less than all of the reagents necessary to generate a bioluminescent reaction. The capsular vehicles include vehicles often used for drug delivery, such as liposomes, and time release capsules; and also capsules made of glass, plastic and other such materials.

For example, the bioluminescence generating reagents (or components) may be coated on the inside of a glass container, such as a glass capillary tube [see, e.g., U.S. Pat. No. 5,387,526]. Upon addition of a composition containing the necessary activating agents, such as molecular oxygen, ATP, a reductase, $Ca^{2+}$ [or other suitable metal ion], the coating will be contacted with the activator and will produce a glow. The capsular vehicles are intended for use in combination with the articles of manufacture.

Thus, the micro- or macro-capsular vehicles, when crushed, opened, dissolved or otherwise placed under conditions that cause delivery of the contents, release material that glows upon contact with air and/or moisture and/or other activator(s). These vehicles vary in size [in the largest dimension] from as small as less than 0.1 μm up to 0.1 cm or more.

Matrix materials, such as glass, plastics, cotton and other textile material, that contain linked bioluminescence-generating reagents are also provided. For example, one or more components of the bioluminescence generating system is (are) linked by adsorption, absorption or other means, directly or indirectly (such as via a linker) to a matrix material. Matrix materials, such as textiles, glass, plastic or ceramic surfaces or particles adapted for linking molecules, for example such as luciferases or luciferins, are combined with at least one component of the bioluminescence generating system, particularly the luciferin, luciferase, or, where the components are amenable, the luciferin and luciferase. The component(s) such as the luciferase are linked to the matrix, such as cotton, using methods known to those of skill in the art of protein synthesis for linking peptides or proteins to solid substrates [see, e.g., Eichler et al. (1993) *Biochemistry* 32:11035–11041; Merrifield (1964) Biochemistry 3:1385–1390.] Linkage is effected either covalently or non-covalently and can be direct or via linkers. Such methods and linkers are well known to those of skill in the chemical arts. The matrix materials with linked bioluminescence generating system components are contacted with an article of manufacture resulting in a novelty item that, when appropriately treated, such as by spraying on a composition that contains the remaining components of the reactions, glows or produces bioluminescence. The matrix materials are advantageously used in the loading cartridges provided herein.

Also provided are single and multi-chamber, particularly dual chamber, apparatus for producing bioluminescence, and combinations of these apparatus with bioluminescence generating reagents are also provided. Such apparatus include at least one chamber that contains all but at least one reagent or component required to produce bioluminescence. Upon addition of the component either to the chamber or after ejection of some or all of the contents of the chamber a bioluminescent glow or glowing fluid, spray or jet is produced. Recharging or charging cartridges adapted for loading these apparatus are also provided.

The charging, or recharging, cartridges are designed to be used to load components of a bioluminescence generating system into or onto an article of manufacture to produce the novelty items, and also to permit reuse after the bioluminescence generating system is spent. The cartridge, which contains one or more chambers, is in an exemplary embodiment fabricated with two-chambers. In a preferred embodiment, the cartridge includes a matrix material, such as a porous membrane or a cotton ball to which a bioluminescence generating agent, such as a luciferase or luciferin, is adsorbed or absorbed such that when flushed with an appropriate composition will be released from the matrix. The first chamber contains one or more components of a bioluminescence generating system used in the bioluminescent process, and the second chamber contains a composition that will flush or otherwise desorb a quantity of the component from the matrix material. Typically, the composition is contained in an easily puncturable or compressible vial and positioned adjacent to the matrix material. In operation, a plunger, a dual pronged plunger where there are two or more chambers, is aligned so that one prong of the plunger is positioned in each chamber, or the plunger may be movably attached to the cartridge, and the output nozzles of the cartridge are aligned against the filler ports of a novelty item, such as a squirt gun. The plunger is then forced into the cartridge, thereby dispensing the components out the nozzle of the first chamber and into the first chamber in the novelty item, and compressing the vial of fluid to flush the remaining components of the bioluminescence generating system from the nozzle of the second chamber and into the second chamber of the novelty item. In this manner, the novelty items contemplated herein may be initially charged, or recharged again and again, by replenishing any or all of the components necessary for generating bioluminescence.

Articles of manufacture containing one or more components of a bioluminescence generating system or a composition, such as a composition containing ATP or $Ca^{2+}$ or other activator, within the packaging material, and a label that indicates that the contents is used for generating bioluminescence are also provided.

Kits containing an article of manufacture and appropriate reagents for generating bioluminescence are also provided.

DESCRIPTION OF THE DRAWINGS

In the accompanying drawings:

FIG. 1 is a side elevation, with portions cut away, of a squirt gun incorporating the dual chamber structure;

FIG. 2 is a sectional view taken on line 2—2 of FIG. 1;

FIG. 3 is a sectional view taken on line 3—3 of FIG. 1;

FIG. 4 is a side elevation view, with portions cut away, of a gas powered toy gun with dual chamber detachable fluid reservoir;

FIG. 5 is a top plan view of the toy gun of FIG. 4, with portions cut away;

FIG. 23 is a side elevation, with portions cut away, of another embodiment of a squirt gun incorporating the dual chamber structure;

FIG. 24 is a top view, with portions cut away, of the nozzle end of the squirt gun of FIG. 23;

FIG. 25 is a sectional view taken on line 25—25 of FIG. 23; and

FIG. 26 is a sectional view taken on line 26—26 of FIG. 23.

DETAILED DESCRIPTION OF THE INVENTION

Table of Contents

Figure 6:
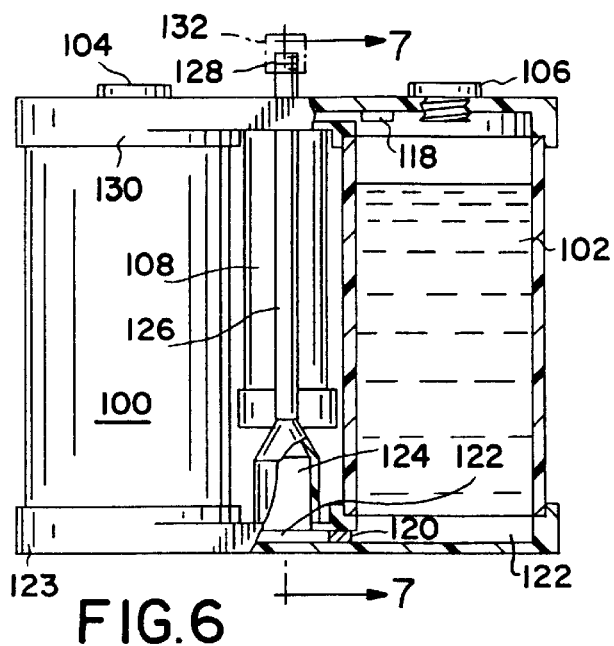
FIG. 6 is a side elevation view, partially cut away of a gas-charged fluid dispensing apparatus incorporating the dual chamber system.

A. Definitions
B. Bioluminescence generating systems
 1. General description
  a. Luciferases
  b. Luciferins
  c. Activators
  d. Reactions
 2. Ctenophore and coelenterate systems
  a. The aequorin system
   (1) Aequorin photoprotein
   (2) Luciferin
  b. The Renilla system
 3. Crustacean, particular Cyrpidina [Vargula], systems
  a. Vargula luciferase
   (1) Purification from Cypridina
   (2) Preparation by Recombinant Methods
  b. Vargula luciferin
  c. Reaction
 4. Insect bioluminescence generating systems including fireflies, click beetles, and other insect systems
  a. Luciferase
  b. Luciferin
  c. Reaction
 5. Bacterial systems
  a. Luciferases
  b. Luciferins
  c. Reactions
 6. Other systems
  a. Dinoflagellate bioluminescence generating systems
  b. Systems from molluscs, such as Latia and Pholas
  c. Earthworms and other annelids
  d. Glow worms
  e. Marine polycheate worm systems
  f. South American railway beetle
  g. Fish
 7. Fluorescent proteins
  a. Green and blue fluorescent proteins
  b. Phycobiliproteins
C. Practice of the reactions in combination with articles of manufacture
D. Packaging of Bioluminescence Systems
 1. Dispensing and Packaging Apparatus for Combination with the Bioluminescence Generating System Components
 2. Capsules, pellets, liposomes, micronized particles
  a. Encapsulating vehicles—in general
  b. Encapsulating vehicles—liposomes
  c. Encapsulating vehicles—gelatin and polymeric vehicles
  d. Endosomes and vacuoles
  e. Micronized particles
 3. Apparatus and substrates
  a. Matrix materials
  b. Immobilization and activation
 4. Apparatus containing a single chamber, housing or a vessel
 5. Dual and multiple chamber fluid dispensing apparatus
  a. Mechanical pump dispensing apparatus
  b. Gas-charged dispensing apparatus
  c. Compressible dispensing apparatus
 6. Other fluid dispensing and packaging apparatus particularly designed for single or multiple uses
  a. Bottle-type single chamber container/bladder apparatus
  b. Dual chambered bottle type container/bladder apparatus for use with foods and beverages
  c. Can type container/bladder apparatus for use with foods and beverages
  d. Spray containers for use to produce a glowing spray
 7. Cap Apparatus for use a single chamber vessel
E. Combinations of articles of manufacture and bioluminescence
 1. Personal care products, including bath powders, bubble baths, products for use on the nails, hair, skin, lips and elsewhere
  a. Bath powders
  b. Glowing dust or powder
  c. Lotions, gels and other topical application formulations
   (1) Lotions
   (2) Creams
   (3) Solutions and suspensions for topical application
   (4) Gels
   (5) Solids
 2. Glowing toys and other items
  a. Single chamber toy guns and other toy weapons that shoot pellets or liquid
  b. Bubble-making toys
  c. Board/Card games
  d. Toy Eggs
  e. Footbags, bean bags and balls
  f. Figurines
 3. Glowing textiles and paper products
 4. Foods and beverages, including ice cubes
  a. Beverages
  b. Ice
  c. Popcorn
 5. Jewelry, Clothing and Other Items of Manufacture
 6. Fountains
 7. Non-Tobacco Toy Cigarettes
 8. Fish, Fish Bait and Fish Food
 9. Plant Food and Animal Food
F. Cartridges for loading (charging or filling) or reloading (recharging) the novelty items A. Definitions Unless defined otherwise, all technical and scientific terms used herein have the same meaning as is commonly understood by one of skill in the art to which this invention belongs. All patents and publications of referred to herein are incorporated by reference in their entirety.

As used herein, novelty items refer to inanimate articles of manufacture that are intended to provide, even for only a few moments, amusement, entertainment, decoration or recreation. The use for recreation or entertainment may be the items only use or may be in addition to other uses or benefits of the items, such as clothing that is modified, as described herein, by combination with bioluminescence.

Novelty items are understood by those of skill in manufacture of such items as well as by the purchasing public and are intended herein to include items, such as, toys, including toy guns, dolls, dummies, figurines, balloons, bubbles, "fairy dust", such as micronized lyophilized particles, puzzles, and inks and paints, particularly fingerpaints; theatrical vapors when mixed, for example with dry ice or a fog; souvenirs; textiles, particularly clothing, including T-shirts, hats, swimsuits, bathing suit, wet suits, scuba diving suits, surfing suits, and other water sport or sports attire; foods and beverages, including gelatins, ice cubes and ice in other shapes, beer, wine, champagne, soft drinks, ice creams, sorbets, ices, frostings, and candy; jewelry, medallions, decorative articles, artificial flowers, articles for displaying names, business trade names, slogans, trademarks on promotional or other such items, such as T-shirts, hats, paints, wrapping paper, gifts intended to promote business goodwill; personal items, such as body paints, body sprays, bubble baths, make-up, body lotions, dentifrices; fountains; jets or sprays of particles or fluids, including "fireworks", sparklers, and magic-wand toys, and many other such novelty items [see, e.g., U.S. Pat. Nos. 5,435,010, 5,460,022, 5,458,931, 5,435,787, 5,435,010, 5,432,623, 5,421,583, 5,419,558, 5,416,927, 5,413,454, 5,413,332, 5,411,427, 5,410,962, 5,407,691, 5,407,391, 5,405,958, 5,405,206, 5,400,698, 5,399,122, 5,398,972, 5,397,609, 5,396,408, 5,393,580, 5,390,086, 5,389,033, 5,383,684, 5,374,805, 5,368,518, 5,363,984, 5,360,010, 5,353,378, 5,351,931, 5,346,455, 5,341,538, 5,323,492, 5,283,911, 5,222,797, 5,177,812, 5,158,349, 4,924,358, 3,597,877 and many others, which describe types of items are considered novelty items]. Any such inanimate item that is combined with bioluminescence is intended to be encompassed herein.

Thus, for purposes herein, a novelty item refers to any inanimate article of manufacture that, upon combination with bioluminescence, provides amusement, entertainment, recreation or enjoyment, if only for even a few moments. Addition of the bioluminescence to the article of manufacture does not add to the function of the item, but adds entertainment, amusement or recreational aspects to the item so that the resulting combination is a novelty item. Therefore, the combinations provided herein are novelty items by virtue of the combination of an inanimate article of manufacture with bioluminescence.

As used herein, inanimate means that the articles of manufacture are not alive nor formerly living [i.e., dead] items. Thus, the novelty items herein, do not encompass living organisms, such as genetically modified fireflies or genetically engineered plants that express luciferase or other such organisms that produce bioluminescence. Animal food and plant food containing luciferin (or luciferase) and/or other activators for use with a transgenic animal or plant that expresses the corresponding luciferase (or luciferin) are provided. These are intended to result in an illuminated animal or plant upon ingestion or consumption or absorption of the food. Transgenic fish and food therefor are also provided herein.

As used herein, personal items include items that are used on the body, such as toothpastes, dentifrices, make-up, nail polishes, body lotions, body creams, body paints and body powders.

As used herein, chemiluminescence refers to a chemical reaction in which energy is specifically channeled to a molecule causing it to become electronically excited and subsequently to release a photon thereby emitting visible light. Temperature does not contribute to this channeled energy. Thus, chemiluminescence involves the direct conversion of chemical energy to light energy. Bioluminescence refers to the subset of chemiluminescence reactions that involve luciferins and luciferases (or the photoproteins). Bioluminescence does not herein include phosphorescence.

As used herein, "fairy dust" refers to particles, such as light sensitive liposomes or micronized powdered particles, that glow upon contact with the air, such as "dust" that a child would use when pretending to be Tinker Bell or other such character.

As used herein, reference to ice cubes include ice in any shape or form, including, but not limited to: cubes; ice formations made from precast molds, such as figurines, icicles, ice sculptures and other such novelty items formed from ice.

As used herein, luminescence refers to the detectable EM radiation, generally, UV, IR or visible EM radiation that is produced when the excited product of an exergic chemical process reverts to its ground state with the emission of light. Chemiluminescence is luminescence that results from a chemical reaction. Bioluminescence is chemiluminescence that results from a chemical reaction using biological molecules [or synthetic versions or analogs thereof] as substrates and/or enzymes.

As used herein, bioluminescence, which is a type of chemiluminescence, refers to the emission of light by biological molecules, particularly proteins. The essential condition for bioluminescence is molecular oxygen, either bound or free in the presence of an oxygenase, a luciferase, which acts on a substrate, a luciferin. Bioluminescence is generated by an enzyme or other protein [luciferase] that is an oxygenase that acts on a substrate luciferin [a bioluminescence substrate] in the presence of molecular oxygen and transforms the substrate to an excited state, which upon return to a lower energy level releases the energy in the form of light.

As used herein, the substrates and enzymes for producing bioluminescence are generically referred to as luciferin and luciferase, respectively. When reference is made to a particular species thereof, for clarity, each generic term is used with the name of the organism from which it derives, for example, bacterial luciferin or firefly luciferase.

As used herein, luciferase refers to oxygenases that catalyze a light emitting reaction. For instance, bacterial luciferases catalyze the oxidation of flavin mononucleotide [FMN] and aliphatic aldehydes, which reaction produces light. Another class of luciferases, found among marine arthropods, catalyzes the oxidation of Cypridina [Vargula] luciferin, and another class of luciferases catalyzes the oxidation of Coleoptera luciferin.

Thus, luciferase refers to an enzyme or photoprotein that catalyzes a bioluminescent reaction [a reaction that produces bioluminescence]. The luciferases, such as firefly and Renilla luciferases, that are enzymes which act catalytically and are unchanged during the bioluminescence generating reaction. The luciferase photoproteins, such as the aequorin and obelin photoproteins to which luciferin is non-covalently bound, are changed, such as by release of the luciferin, during bioluminescence generating reaction. The luciferase is a protein that occurs naturally in an organism or a variant or mutant thereof, such as a variant produced by mutagenesis that has one or more properties, such as thermal or pH stability, that differ from the naturally-occurring protein. Luciferases and modified mutant or variant forms thereof are well known.

Thus, reference, for example, to "Renilla luciferase" means an enzyme isolated from member of the genus Renilla or an equivalent molecule obtained from any other source, such as from another Anthozoa, or that has been prepared synthetically.

The luciferases and luciferin and activators thereof are referred to as bioluminescence generating reagents or components. Typically, a subset of these reagents will be provided or combined with an article of manufacture. Bioluminescence will be produced upon contacting the combination with the remaining reagents. Thus, as used herein, the component luciferases, luciferins, and other factors, such as $O_2$, $Mg^{2+}$, $Ca^{2+}$ are also referred to as bioluminescence generating reagents [or agents or components].

As used herein, "not strictly catalytically" means that the photoprotein acts as a catalyst to promote the oxidation of the substrate, but it is changed in the reaction, since the bound substrate is oxidized and bound molecular oxygen is used in the reaction. Such photoproteins are regenerated by addition of the substrate and molecular oxygen under appropriate conditions known to those of skill in this art.

As used herein, bioluminescence substrate refers to the compound that is oxidized in the presence of a luciferase, and any necessary activators, and generates light. These substrates are referred to as luciferins, which are substrates that undergo oxidation in a bioluminescence reaction. These bioluminescence substrates include any luciferin or analog thereof or any synthetic compound with which a luciferase interacts to generate light. Preferred substrates are those that are oxidized in the presence of a luciferase or protein in a light-generating reaction. Bioluminescence substrates, thus, include those compounds that those of skill in the art recognize as luciferins. Luciferins, for example, include firefly luciferin, Cypridina [also known as Vargula] luciferin [coelenterazine], bacterial luciferin, as well as synthetic analogs of these substrates or other compounds that are oxidized in the presence of a luciferase in a reaction the produces bioluminescence.

As used herein, capable of conversion into a bioluminescence substrate means susceptible to chemical reaction, such as oxidation or reduction, that yields a bioluminescence substrate. For example, the luminescence producing reaction of bioluminescent bacteria involves the reduction of a flavin mononucleotide group (FMN) to reduced flavin mononucleotide ($FMNH_2$) by a flavin reductase enzyme. The reduced flavin mononucleotide [substrate] then reacts with oxygen [an activator] and bacterial luciferase to form an intermediate peroxy flavin that undergoes further reaction, in the presence of a long-chain aldehyde, to generate light. With respect to this reaction, the reduced flavin and the long chain aldehyde are substrates.

As used herein, bioluminescence system [or bioluminescence generating system] refers to the set of reagents required for a bioluminescence-producing reaction. Thus, the particular luciferase, luciferin and other substrates, solvents and other reagents that may be required to complete a bioluminescent reaction form a bioluminescence system. Therefore, a bioluminescence system (or equivalently a bioluminescence generating system) refers to any set of reagents that, under appropriate reaction conditions, yield bioluminescence. Appropriate reaction conditions refers to the conditions necessary for a bioluminescence reaction to occur, such as pH, salt concentrations and temperature. In general, bioluminescence systems include a bioluminescence substrate (a luciferin), a luciferase, which includes enzymes luciferases and photoproteins, and one or more activators. A particular bioluminescence system may be identified by reference to the specific organism from which the luciferase derives; for example, the Vargula [also called Cypridina] bioluminescence system (or Vargula system) includes a Vargula luciferase, such as a luciferase isolated from the ostracod, Vargula or produced using recombinant means or modifications of these luciferases. This system would also include the particular activators necessary to complete the bioluminescence reaction, such as oxygen and a substrate with which the luciferase reacts in the presence of the oxygen to produce light.

As used herein, recharging or reloading the item refers to the means by which spent bioluminescence generating components are added to an item. Recharging generally refers to a process in which one component, such as a luciferase is added to an item, such as a textile; reloading refers to the process in which all components are added to an item, such as a refillable squirt gun.

As used herein, ATP, AMP, NAD+ and NADH refer to adenosine triphosphate, adenosine monophosphate, nicotinamide adenine dinucleotide (oxidized form) and nicotinamide adenine dinucleotide (reduced form), respectively.

As used herein, production by recombinant means by using recombinant DNA methods means the use of the well known methods of molecular biology for expressing proteins encoded by cloned DNA.

As used herein, substantially identical to a product means sufficiently similar so that the property of interest is sufficiently unchanged so that the substantially identical product can be used in place of the product.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein equivalent, when referring to two sequences of nucleic acids means that the two sequences in question encode the same sequence of amino acids or equivalent proteins. When "equivalent" is used in referring to two proteins or peptides, it means that the two proteins or peptides have substantially the same amino acid sequence with only conservative amino acid substitutions [see, e.g., Table 2, below] that do not substantially alter the activity or function of the protein or peptide. When "equivalent" refers to a property, the property does not need to be present to the same extent [e.g., two peptides can exhibit different rates of the same type of enzymatic activity], but the activities are preferably substantially the same. "Complementary," when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: stringency of hybridization in determining percentage mismatch is as follows:

1) high stringency: 0.1× SSPE, 0.1% SDS, 65° C.
2) medium stringency: 0.2× SSPE, 0.1% SDS, 50° C.
3) low stringency: 1.0× SSPE, 0.1% SDS, 50° C.

It is understood that equivalent stringencies may be achieved using alternative buffers, salts and temperatures.

The term "substantially" varies with the context as understood by those skilled in the relevant art and generally means at least 70%, preferably means at least 80%, more preferably at least 90%, and most preferably at least 95%.

As used herein, biological activity refers to the in vivo activities of a compound or physiological responses that result upon administration of a compound, composition or other mixture. Biological activities may be observed in in vitro systems designed to test or use such activities. Thus, for purposes herein the biological activity of a luciferase is its oxygenase activity whereby, upon oxidation of a substrate, light is produced.

As used herein, a composition refers to a any mixture. It may be a solution, a suspension, liquid, powder, a paste, aqueous, non-aqueous or any combination thereof.

As used herein, a combination refers to any association between two or among more items.

As used herein, fluid refers to any composition that can flow. Fluids thus encompass compositions that are in the form of semi-solids, pastes, solutions, aqueous mixtures, gels, lotions, creams and other such compositions.

As used herein, plant food refers to any liquids, water-soluble or water-insoluble solids, such as fertilizers containing any ratio of nitrogen, potassium and/or phosphorous, formulations, combinations, polymers or plant growth promoters, such as auxins and hormones, that is applied to a plant to promote or maintain growth [e.g., see U.S. Pat. Nos. 4,016,880, 4,711,659, 4,804,403, 5,547,486, 5,553,853, RE 35,320, and RE 31,801]. The plant food may be applied directly to the soil, sprayed on the foliage of the plant or a combination thereof. The plant food may be slow releasing or available immediately for consumption by the plant. The plant food may be applied to any plant that can be genetically engineered to contain a heterologous gene encoding a component of a bioluminescence generating system, preferably a luciferase. Examples of such plants, but not meant to be limiting to, are grasses, agricultural plants and ornamental plants.

B. Bioluminescence Generating Systems

A bioluminescence generating system refers to the components that are necessary and sufficient to generate bioluminescence. These include a luciferase, luciferin and any necessary co-factors or conditions. Virtually any bioluminescence generating system known to those of skill in the art will be amenable to use in the apparatus, systems, combinations and methods provided herein. Factors for consideration in selecting a bioluminescence generating system, include, but are not limited to: the item used in combination with the bioluminescence; the medium in which the reaction is run; stability of the components, such as temperature or pH sensitivity; shelf life of the components; sustainability of the light emission, whether constant or intermittent; availability of components; desired light intensity; and other such factors.

1. General Description

In general, bioluminescence refers to an energy-yielding chemical reaction in which a specific chemical substrate, a luciferin, undergoes oxidation, catalyzed by an enzyme, a luciferase. Bioluminescent reactions are easily maintained, requiring only replenishment of exhausted luciferin or other substrate or cofactor or other protein, in order to continue or revive the reaction. Bioluminescence generating reactions are well known to those of skill in this art and any such reaction may be adapted for use in combination with articles of manufacture as described herein.

There are numerous organisms and sources of bioluminescence generating systems, and some representative genera and species that exhibit bioluminescence are set forth in the following table [reproduced in part from Hastings in (1995) *Cell Physiology: Source Book*, N. Sperelakis (ed.), Academic Press, pp 665–681]:

TABLE 1

| Representative luminous organism | |
|---|---|
| Type of Organism | Representative genera |
| Bacteria | Photobacterium |
|  | Vibrio |
|  | Xenorhabdus |
| Mushrooms | Panus, Armillaria |
|  | Pleurotus |
| Dinoflagellates | Gonyaulax |
|  | Pyrocystis |
|  | Noctiluca |
| Cnidaria (coelenterates) | |
| Jellyfish | Aequorea |
| Hydroid | Obelia |
| Sea Pansy | Renilla |
| Ctenophores | Mnemiopsis |
|  | Beroe |
| Annelids | |
| Earthworms | Diplocardia |
| Marine polychaetes | Chaetopterus, Phyxotrix |
| Syllid fireworm | Odontosyllis |
| Molluscs | |
| Limpet | Latia |
| Clam | Pholas |
| Squid | Heteroteuthis |
|  | Heterocarpus |
| Crustacea | |
| Ostracod | Vargula (Cypridina) |
| Shrimp (euphausids) | Meganyctiphanes |
|  | Acanthophyra |
|  | Oplophorus |
|  | Gnathophausia |
| Decapod | Sergestes |
| Copepods | |
| Insects | |
| Coleopterids (beetles) | |
| Firefly | Photinus, Photuris |
| Click beetles | Pyrophorus |
| Railroad worm | Phengodes, Phrixothrix |
| Diptera (flies) | Arachnocampa |
| Echinoderms | |
| Brittle stars | Ophiopsila |
| Sea cucumbers | Laetmogone |
| Chordates | |
| Tunicates | Pyrosoma |
| Fish | |
| Cartilaginous | Squalus |
| Bony | |
| Ponyfish | Leiognathus |
| Flashlight fish | Photoblepharon |
| Angler fish | Cryptopsaras |
| Midshipman | Porichthys |
| Lantern fish | Benia |
| Shiny loosejaw | Aristostomias |
| Hatchet fish | Agyropelecus |

TABLE 1-continued

Representative luminous organism

| Type of Organism | Representative genera |
|---|---|
| and other fish | Pachystomias |
| | Malacosteus |
| Midwater fish | Cyclothone |
| | Neoscopelus |
| | Tarletonbeania |

Other bioluminescent organisms contemplated for use herein are Gonadostomias, Gaussia, Halisturia, Vampire squid, Glyphus, Mycotophids (fish), Vinciguerria, Howella, Florenciella, Chaudiodus, Melanocostus and Sea Pens.

It is understood that a bioluminescence generating system may be isolated from natural sources, such as those in the above Table, or may be produced synthetically. In addition, for uses herein, the components need only be sufficiently pure so that mixture thereof, under appropriate reaction conditions, produces a glow. Thus it has been found, in some embodiments, a crude extract or merely grinding up the organism may be adequate. Generally, however, substantially pure components are used, but, where necessary, the precise purity can be determined empirically. Also, components may be synthetic components that are not isolated from natural sources. DNA encoding luciferases is available [see, e.g., SEQ ID Nos. 1–13] and has been modified [see, e.g., SEQ ID Nos. 3 and 10–13] and synthetic and alternative substrates have been devised. The DNA listed herein is only representative of the DNA encoding luciferases that is available.

Any bioluminescence generating system, whether synthetic or isolated form natural sources, such as those set forth in Table 1, elsewhere herein or known to those of skill in the art, is intended for use in the combinations, systems and methods provided herein. Chemiluminescence systems per se, which do not rely on oxygenases [luciferases] are not encompassed herein.

a. Luciferases

Luciferases refer to any compound that, in the presence of any necessary activators, catalyze the oxidation of a bioluminescence substrate [luciferin] in the presence of molecular oxygen, whether free or bound, from a lower energy state to a higher energy state such that the substrate, upon return to the lower energy state, emits light. For purposes herein, luciferase is broadly used to encompass enzymes that act catalytically to generate light by oxidation of a substrate and also photoproteins, such as aequorin, that act, though not strictly catalytically [since such proteins are exhausted in the reaction], in conjunction with a substrate in the presence of oxygen to generate light. These luciferases, including photoproteins, such as aequorin, are herein also included among the luciferases. These reagents include the naturally-occurring luciferases [including photoproteins], proteins produced by recombinant DNA, and mutated or modified variants thereof that retain the ability to generate light in the presence of an appropriate substrate, co-factors and activators or any other such protein that acts as a catalyst to oxidize a substrate, whereby light is produced.

Generically, the protein that catalyzes or initiates the bioluminescent reaction is referred to as a luciferase, and the oxidizable substrate is referred to as a luciferin. The oxidized reaction product is termed oxyluciferin, and certain luciferin precursors are termed etioluciferin. Thus, for purposes herein bioluminescence encompasses light produced by reactions that are catalyzed by [in the case of luciferases that act enzymatically] or initiated by [in the case of the photoproteins, such as aequorin, that are not regenerated in the reaction] a biological protein or analog, derivative or mutant thereof.

For clarity herein, these catalytic proteins are referred to as luciferases and include enzymes such as the luciferases that catalyze the oxidation of luciferin, emitting light and releasing oxyluciferin. Also included among luciferases are photoproteins, which catalyze the oxidation of luciferin to emit light but are changed in the reaction and must be reconstituted to be used again. The luciferases may be naturally occurring or may be modified, such as by genetic engineering to improve or alter certain properties. As long as the resulting molecule retains the ability to catalyze the bioluminescent reaction, it is encompassed herein.

Any protein that has luciferase activity [a protein that catalyzes oxidation of a substrate in the presence of molecular oxygen to produce light as defined herein] may be used herein. The preferred luciferases are those that are described herein or that have minor sequence variations. Such minor sequence variations include, but are not limited to, minor allelic or species variations and insertions or deletions of residues, particularly cysteine residues. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p.224). Such substitutions are preferably made in accordance with those set forth in TABLE 2 as follows:

TABLE 2

| Original residue | Conservative substitution |
|---|---|
| Ala (A) | Gly; Ser |
| Arg (R) | Lys |
| Asn (N) | Gln; His |
| Cys (C) | Ser; neutral amino acid |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions. Any such modification of the polypeptide may be effected by any means known to those of skill in this art.

The luciferases may be obtained commercially, isolated from natural sources, expressed in host cells using DNA encoding the luciferase, or obtained in any manner known to those of skill in the art. For purposes herein, crude extracts obtained by grinding up selected source organisms may suffice. Since large quantities of the luciferase may be desired, isolation of the luciferase from host cells is preferred. DNA for such purposes is widely available as are modified forms thereof.

Examples of luciferases include, but are not limited to, those isolated from the ctenophores Mnemiopsis (mnemiopsin) and Beroe ovata (berovin), those isolated from the coelenterates Aequorea (aequorin), Obelia (obelin), Pelagia, the Renilla luciferase, the luciferases isolated from the mollusca Pholas (pholasin), the luciferases isolated from the Aristostomias and Porichthys fish and from the ostracods, such as Cypridina (also referred to as Vargula). Preferred luciferases for use herein are the Aequorin protein, Renilla luciferase and Cypridina [also called Vargula] luciferase [see, e.g., SEQ ID Nos. 1, 2, and 4–13]. Also, preferred are luciferases which react to produce red and/or near infrared light. These include luciferases found in species of Aristostomias, such as $A.$ $scintillans,$ Pachystomias, Malacosteus, such as $M.$ $niger.$ b. Luciferins The substrates for the reaction include any molecule(s) with which the luciferase reacts to produce light. Such molecules include the naturally-occurring substrates, modified forms thereof, and synthetic substrates [see, e.g., U.S. Pat. Nos. 5,374,534 and 5,098,828]. Exemplary luciferins include those described herein, as well as derivatives thereof, analogs thereof, synthetic substrates, such as dioxetanes [see, e.g., U.S. Pat. Nos. 5,004,565 and 5,455,357], and other compounds that are oxidized by a luciferase in a light-producing reaction [see, e.g., U.S. Pat. Nos. 5,374,534, 5,098,828 and 4,950,588]. Such substrates also may be identified empirically by selecting compounds that are oxidized in bioluminescent reactions.

c. Activators

The bioluminescence generating systems also require additional components discussed herein and known to those of skill in the art. All bioluminescent reactions require molecular oxygen in the form of dissolved or bound oxygen. Thus, molecular oxygen, dissolved in water or in air or bound to a photoprotein, is the activator for bioluminescence reactions. Depending upon the form of the components, other activators include, but are not limited to, ATP [for firefly luciferase], flavin reductase [bacterial systems] for regenerating $FMNH_2$ from FMN, and $Ca^{2+}$ or other suitable metal ion [aequorin].

Most of the systems provided herein will generate light when the luciferase and luciferin are mixed and exposed to air or water. The systems that use photoproteins that have bound oxygen, such as aequorin, however, will require exposure to $Ca^{2+}$ [or other suitable metal ion], which can be provided in the form of an aqueous composition of a calcium salt. In these instances, addition of a $Ca^{2+}$ [or other suitable metal ion] to a mixture of luciferase [aequorin] and luciferin [such as coelenterazine] will result in generation of light. The Renilla system and other Anthozoa systems also require $Ca^{2+}$ [or other suitable metal ion].

If crude preparations are used, such as ground up Cypridina [shrimp] or ground fireflies, it may be necessary to add only water. In instances in which fireflies [or a firefly or beetle luciferase] are used the reaction may only require addition ATP. The precise components will be apparent, in light of the disclosure herein, to those of skill in this art or may be readily determined empirically.

It is also understood that these mixtures will also contain any additional salts or buffers or ions that are necessary for each reaction to proceed. Since these reactions are well-characterized, those of skill in the art will be able to determine precise proportions and requisite components. Selection of components will depend upon the apparatus, article of manufacture and luciferase. Various embodiments are described and exemplified herein; in view of such description, other embodiments will be apparent.

d. Reactions

In all embodiments, up to all but one component of a bioluminescence generating system will be mixed with or packaged with or otherwise combined with a selected article of manufacture to produce the novelty item. When bioluminescence is desired, the remaining component(s) will be added and light will be produced.

In general, since the result to be achieved is the production of light visible to the naked eye for entertainment, amusement or recreation, for the purposes herein, the precise proportions and amounts of components of the bioluminescence reaction need not be stringently determined or met. They must be sufficient to produce light. Generally, an amount of luciferin and luciferase sufficient to generate a visible glow is used; this amount can be readily determined empirically and is dependent upon the selected system and selected application.

For purposes herein, such amount is preferably at least the concentrations and proportions used for analytical purposes by those of skill in the such arts. Higher concentrations may be used if the glow is not sufficiently bright. Also because the conditions in which the reactions are used are not laboratory conditions and the components are subject to storage, higher concentration may be used to overcome any loss of activity. Typically, the amounts are 1 mg, preferably 10 mg and more preferably 100 mg, of a luciferase per liter of reaction mixture or 1 mg, preferably 10 mg, more preferably 100 mg, coated on a portion of a T-shirt or other textile or paper. Such coating may be produced by drying a composition containing at least about 0.01 mg/l, and typically 0.1 mg/l, 1 mg/l, 10 mg/l or more of each component on the item. The amount of luciferin is also between about 0.01 and 100 mg/l, preferably between 0.1 and 10 mg/l, additional luciferin can be added to many of the reactions to continue the reaction. In embodiments in which the luciferase acts catalytically and does not need to be regenerated, lower amounts of luciferase can be used. In those in which it is changed during the reaction, it also can be replenished; typically higher concentrations will be selected. Ranges of concentration per liter [or the amount of coating on substrate the results from contacting with such composition] of each component on the order of 0.1 to 20 mg, preferably 0.1 to 10 mg, more preferably between about 1 and 10 mg of each component will be sufficient. When preparing coated substrates, as described herein, greater amounts of coating compositions containing higher concentrations of the luciferase or luciferin may be used.

Thus, for example, in presence of calcium, 5 mg of luciferin, such as coelenterazine, in one liter of water will glow brightly for at least about 10 to 20 minutes, depending on the temperature of the water, when about 10 mgs of luciferase, such as aequorin photoprotein luciferase or luciferase from Renilla, is added thereto. Increasing the concentration of luciferase, for example, to 100 mg/l, provides a particularly brilliant display of light.

If desired, the onset of the bioluminescent reaction can be delayed by adding an, an inhibitor, for example magnesium, of the bioluminescence generating reaction. Also, where inhibition is not desired, the concentration of free magnesium may be reduced by addition of a sufficient amount of chelating agent, such as ethylenediamine-tetraacetic acid [EDTA]. The amount of EDTA and also calcium can be empirically determined to appropriately chelate magnesium, without inhibiting or preventing the desired bioluminescence.

It is understood, that concentrations and amounts to be used depend upon the selected article of manufacture and they may be readily determined empirically. Proportions, particularly those used when commencing an empirical determination, are generally those used for analytical purposes, and amounts or concentrations are at least those used for analytical purposes, but the amounts can be increased, particularly if a sustained and brighter glow is desired.

2. Ctenophore and Coelenterate Systems

Ctenophores, such as Mnemiopsis (mnemiopsin) and Beroe ovata (berovin), and coelenterates, such as Aequorea (aequorin), Obelia (obelin) and Pelagia, produce bioluminescent light using similar chemistries [see, e.g., Stephenson et al. (1981) Biochimica et Biophysica Acta 678:65–75; Hart et al. (1979) Biochemistry 18:2204–2210; International PCT Application No. WO94/18342, which is based on U.S. application Ser. No. 08/017,116, U.S. Pat. No. 5,486,455 and other references and patents cited herein]. The Aequorin and Renilla systems are representative and are described in detail herein as exemplary and as among the presently preferred systems. The Aequorin and Renilla systems can use the same luciferin and produce light using the same chemistry, but each luciferase is different. The Aequorin luciferase aequorin, as well as, for example, the luciferases mnemiopsin and berovin, is a photoprotein that includes bound oxygen and bound luciferin, requires $Ca^{2+}$ [or other suitable metal ion] to trigger the reaction, and must be regenerated for repeated use; whereas, the Renilla luciferase acts as a true enzyme because it is unchanged during the reaction and it requires dissolved molecular oxygen.

a. The Aequorin System

The aequorin system is well known [see, e.g., Tsuji et al. (1986) "Site-specific mutagenesis of the calcium-binding photoprotein aequorin," Proc. Natl. Acad. Sci. USA 83:8107–8111; Prasher et al. (1985) "Cloning and Expression of the cDNA Coding for Aequorin, a Bioluminescent Calcium-Binding Protein," Biochemical and Biophysical Research Communications 126:1259–1268; Prasher et al. (1986) Methods in Enzymology 133:288–297; Prasher, et al. (1987) "Sequence Comparisons of cDNAs Encoding for Aequorin Isotypes," Biochemistry 26:1326–1332; Charbonneau et al. (1985) "Amino Acid Sequence of the Calcium-Dependent Photoprotein Aequorin," Biochemistry 24:6762–6771; Shimomura et al. (1981) "Resistivity to denaturation of the apoprotein of aequorin and reconstitution of the luminescent photoprotein from the partially denatured apoprotein," Biochem. J. 199:825–828; Inouye et al. (1989) J. Biochem. 105:473–477; Inouye et al. (1986) "Expression of Apoaequorin Complementary DNA in Escherichia coli," Biochemistry 25:8425–8429; Inouye et al. (1985) "Cloning and sequence analysis of cDNA for the luminescent protein aequorin," Proc. Natl. Acad. Sci. USA 82:3154–3158; Prendergast, et al. (1978) "Chemical and Physical Properties of Aequorin and the Green Fluorescent Protein Isolated from Aequorea forskalea" J. Am. Chem. Soc. 17:3448–3453; European Patent Application 0 540 064 A1; European Patent Application 0 226 979 A2, European Patent Application 0 245 093 A1 and European Patent Specification 0 245 093 B1; U.S. Pat. No. 5,093,240; U.S. Pat. No. 5,360,728; U.S. Pat. No. 5,139,937; U.S. Pat. No. 5,422,266; U.S. Pat. No. 5,023,181; U.S. Pat. No. 5,162,227; and SEQ ID Nos. 5–13, which set forth DNA encoding the apoprotein; and a form, described in U.S. Pat. No. 5,162,227, European Patent Application 0 540 064 A1 and Sealite Sciences Technical Report No. 3 (1994), is commercially available from Sealite, Sciences, Bogart, Ga. as AQUALITE®].

This system is among the preferred systems for use herein. As will be evident, since the aequorin photoprotein includes noncovalently bound luciferin and molecular oxygen, it is suitable for storage in this form as a lyophilized powder or encapsulated into a selected delivery vehicle. The system can be encapsulated into pellets, such as liposomes or other delivery vehicles, or stored in single chamber dual or other multiple chamber apparatus. When used, the vehicles are contacted with a composition, even tap water, that contains $Ca^{2+}$ [or other suitable metal ion], to produce a mixture that glows. This system is preferred for use in numerous embodiments herein, such as in any embodiment that uses pellets. These embodiments include, squirt guns, fairy dust, bubble toys, bubble baths, soaps, linked to textiles, for addition to beverages and foods.

(1) Aequorin and Related Photoproteins

The photoprotein, aequorin, isolated from the jellyfish, Aequorea, emits light upon the addition of $Ca^{2+}$ [or other suitable metal ion]. The aequorin photoprotein, which includes bound luciferin and bound oxygen that is released by $Ca^{2+}$, does not require dissolved oxygen. Luminescence is triggered by calcium, which releases oxygen and the luciferin substrate producing apoaqueorin.

The bioluminescence photoprotein aequorin is isolated from a number of species of the jellyfish Aequorea. It is a 22 kilodalton [kD] molecular weight peptide complex [see, e.g., Shimomura et al. (1962) J. Cellular and Comp. Physiol. 59:233–238; Shimomura et al. (1969) Biochemistry 8:3991–3997; Kohama et al. (1971) Biochemistry 10:4149–4152; and Shimomura et al. (1972) Biochemistry 11:1602–1608]. The native protein contains oxygen and a heterocyclic compound coelenterazine, a luciferin, [see, below] noncovalently bound thereto. The protein contains three calcium binding sites. Upon addition of trace amounts $Ca^{2+}$ [or other suitable metal ion, such as strontium] to the photoprotein, it undergoes a conformational change the catalyzes the oxidation of the bound coelenterazine using the protein-bound oxygen. Energy from this oxidation is released as a flash of blue light, centered at 469 nm. Concentrations of calcium ions as low as $10^{-6}$ M are sufficient to trigger the oxidation reaction.

Naturally-occurring apoaequorin is not a single compound but rather is a mixture of microheterogeneous molecular species. Aequoria jellyfish extracts contain as many as twelve distinct variants of the protein [see, e.g., Prasher et al. (187) Biochemistry 26:1326–1332; Blinks et al. (1975) Fed. Proc. 34:474]. DNA encoding numerous forms has been isolated [see, e.g., SEQ ID Nos. 5–9 and 13].

The photoprotein can be reconstituted [see, e.g., U.S. Pat. No. 5,023,181] by combining the apoprotein, such as a protein recombinantly produced in E. coli, with a coelenterazine, such as a synthetic coelenterazine, in the presence of oxygen and a reducing agent [see, e.g., Shimomura et al. (1975) Nature 256:236–238; Shimomura et al. (1981) Biochemistry J. 199:825–828], such as 2-mercaptoenthanol, and also EDTA or EGTA [concentrations between about 5 to about 100 mM or higher for applications herein] tie up any $Ca^{2+}$ to prevent triggering the oxidation reaction until desired. DNA encoding a modified form of the apoprotein that does not require 2-mercaptoethanol for reconstitution is also available [see, e.g., U.S. Pat. No. U.S. Pat. No. 5,093,240]. The reconstituted photoprotein is also commercially available [sold, e.g., under the trademark AQUALITE®, which is described in U.S. Pat. No. 5,162,227].

The light reaction is triggered by adding $Ca^{2+}$ at a concentration sufficient to overcome the effects of the chelator and achieve the $10^{-6}$ M concentration. Because such low concentrations of $Ca^{2+}$ can trigger the reaction, for use in the methods and apparatus herein, higher concentrations of chelator may be included in the compositions of photoprotein. Accordingly, higher concentrations of added $Ca^{2+}$ in the form of a calcium salt will be required. Precise amounts may be empirically determined. For use herein, it may be sufficient to merely add water to the photoprotein, which is provided in the form of a concentrated composition or in lyophilized or powdered form. Thus, for purposes herein, addition of small quantities of $Ca^{2+}$, such as those present in most tap water or in phosphate buffered saline (PBS) or other suitable buffers or possible in the moisture on the skin, should trigger the bioluminescence reaction.

Numerous isoforms of the aequorin apoprotein been identified isolated. DNA encoding these proteins has been cloned, and the proteins and modified forms thereof have been produced using suitable host cells [see, e.g., U.S. Pat. Nos. 5,162,227, 5,360,728, 5,093,240; see, also, Prasher et al. (1985) *Biophys. Biochem. Res. Commun.* 126:1259–1268; Inouye et al. (1986) *Biochemistry* 25: 8425–8429]. U.S. Pat. No. 5,093,240; U.S. Pat. No. 5,360, 728; U.S. Pat. No. 5,139,937; U.S. Pat. No. 5,288,623; U.S. Pat. No. 5,422,266, U.S. Pat. No. 5,162,227 and SEQ ID Nos. 5–13, which set forth DNA encoding the apoprotein; and a form is commercially available form Sealite, Sciences, Bogart, Ga. as AQUALITE®]. DNA encoding apoaequorin or variants thereof is useful for recombinant production of high quantities of the apoprotein. The photoprotein is reconstituted upon addition of the luciferin, coelenterazine, preferably a sulfated derivative thereof, or an analog thereof, and molecular oxygen [see, e.g., U.S. Pat. No. 5,023,181]. The apoprotein and other constituents of the photoprotein and bioluminescence generating reaction can be mixed under appropriate conditions to regenerate the photoprotein and concomitantly have the photoprotein produce light. Reconstitution requires the presence of a reducing agent, such as mercaptoethanol, except for modified forms, discussed below, that are designed so that a reducing agent is not required [see, e.g., U.S. Pat. No. 5,093,240].

For use herein, it is preferred aequorin is produced using DNA, such as that set forth in SEQ ID Nos. 5–13 and known to those of skill in the art or modified forms thereof. The DNA encoding aequorin is expressed in a host cell, such as *E. coli,* isolated and reconstituted to produce the photoprotein [see, e.g., U.S. Pat. Nos. 5,418,155, 5,292,658, 5,360, 728, 5,422,266, 5,162,227].

Of interest herein, are forms of the apoprotein that have been modified so that the bioluminescent activity is greater than unmodified apoaequorin [see, e.g., U.S. Pat. No. 5,360, 728, SEQ ID Nos. 10–12]. Modified forms that exhibit greater bioluminescent activity than unmodified apoaequorin include proteins having sequences set forth in SEQ ID Nos. 10–12, in which aspartate 124 is changed to serine, glutamate 135 is changed to serine, and glycine 129 is changed to alanine, respectively. Other modified forms with increased bioluminescence are also available.

For use in certain embodiments herein, the apoprotein and other components of the aequorin bioluminescence generating system are packaged or provided as a mixture, which, when desired is subjected to conditions under which the photoprotein reconstitutes from the apoprotein, luciferin and oxygen [see, e.g., U.S. Pat. No. 5,023,181; and U.S. Pat. No. 5,093,240]. Particularly preferred are forms of the apoprotein that do not require a reducing agent, such as 2-mercaptoethanol, for reconstitution. These forms, described, for example in U.S. Patent No. 5,093,240 [see, also Tsuji et al. (1986) *Proc. Natl. Acad. Sci. U.S.A.* 83:8107–8111], are modified by replacement of one or more, preferably all three cysteine residues with, for example serine. Replacement may be effected by modification of the DNA encoding the aequorin apoprotein, such as that set forth in SEQ ID No. 5, and replacing the cysteine codons with serine.

The photoproteins and luciferases from related species, such as Obelia are also contemplated for use herein. DNA encoding the $Ca^{2+}$-activated photoprotein obelin from the hydroid polyp *Obelia longissima* is known and available [see, e.g., Illarionov et al. (1995) *Gene* 153:273–274; and Bondar et al. (1995) *Biochim. Biophys. Acta* 1231:29–32]. This photoprotein can also be activated by $Mn^{2+}$ [see, e.g., Vysotski et al. (1995) *Arch. Bioch. Biophys.* 316:92–93, Vysotski et al. (1993) *J. Biolumin. Chemilumin.* 8:301–305].

In general for use herein, the components of the bioluminescence are packaged or provided so that there is insufficient metal ions to trigger the reaction. When used, the trace amounts of triggering metal ion, particularly $Ca^{2+}$ is contacted with the other components. For a more sustained glow, aequorin can be continuously reconstituted or can be added or can be provided in high excess.

(2) Luciferin

The aequorin luciferin is coelenterazine and analogs therein, which include molecules having the structure [formula (I)]:

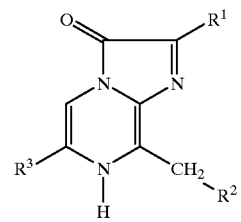

in which $R_1$ is $CH_2C_6H_5$ or $CH_3$; $R_2$ is $C_6H_5$, and $R_3$ is $p-C_6H_4OH$ or $CH_3$ or other such analogs that have activity. Preferred coelenterazine has the structure in which $R^1$ is $p-CH_2C_6H_4OH$, $R_2$ is $C_6H_5$, and $R_3$ is $p-C_6H_4OH$, which can be prepared by known methods [see, e.g., Inouye et al. (1975) *Jap. Chem. Soc., Chemistry Lttrs.* pp 141–144; and Hart et al. (1979) *Biochemistry* 18:2204–2210]. The preferred coelenterazine has the structure (formula (II)):

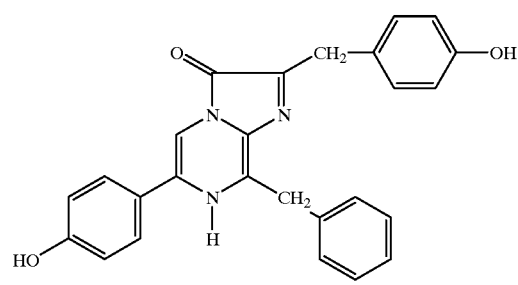

and sulfated derivatives thereof.

The reaction of coelenterazine when bound to the aequorin photoprotein with bound oxygen and in the presence of $Ca^{2+}$ can represented as follows:

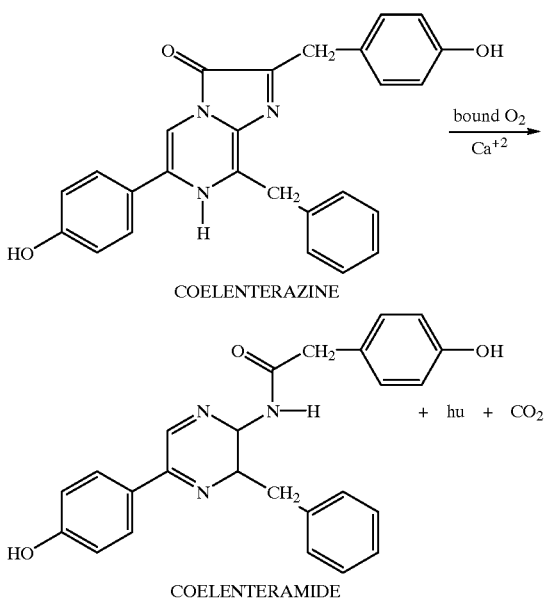

COELENTERAZINE

COELENTERAMIDE

The photoprotein aequorin [which contains apoaequorin bound to a coelenterate luciferin molecule] and Renilla luciferase, discussed below, can use the same coelenterate luciferin. The aequorin photoprotein catalyses the oxidation of coelenterate luciferin [coelenterazine] to oxyluciferin [coelenteramide] with the concomitant production of blue light [lambda$_{max}$=469 nm].

Importantly, the sulfate derivative of the coelenterate luciferin [lauryl-luciferin] is particularly stable in water, and thus may be used in a coelenterate-like bioluminescence generating system. In this system, adenosine diphosphate (ADP) and a sulpha-kinase are used to convert the coelenterazine to the sulphated form. Sulfatase is then used to reconvert the lauryl-luciferin to the native coelenterazine. Thus, the more stable lauryl-luciferin is used in the item to be illuminated and the luciferase combined with the sulfatase are added to the luciferin mixture when illumination is desired.

Thus, the bioluminescence generating system of Aequorea is particularly suitable for use in the methods and apparatus herein. The particular amounts and the manner in which the components are provided depends upon the selected combination of article of manufacture. This system can be provided in lyophilized form, that will glow upon addition of $Ca^{2+}$. It can be encapsulated, linked to matrices, such as porous glass, or in as a compositions, such as a solution or suspension, preferably in the presence of sufficient chelating agent to prevent triggering the reaction. The concentration of the aequorin photoprotein will vary and can be determined empirically. Typically concentrations of at least 0.1 mg/l, more preferably at least 1 mg/l and higher, will be selected. In certain embodiments, 1–10 mg luciferin/ 100 mg of luciferase will be used in selected volumes and at the desired concentrations will be used.

b. The Renilla System

Representative of coelenterate systems is the Renilla system. Renilla, also known as sea pansies, are members of the class of coelenterates Anthozoa, which includes other bioluminescent genera, such as Cavarnularia, Ptilosarcus, Stylatula, Acanthoptilum, and Parazoanthus. Bioluminescent members of the Anthozoa genera contain luciferases and luciferins that are similar in structure [see, e.g., Cormier et al. (1973) *J. Cell. Physiol.* 81:291–298; see, also Ward et al. (1975) *Proc. Natl. Acad. Sci. U.S.A.* 72:2530–2534]. The luciferases and luciferins from each of these anthozoans crossreact and produce a characteristic blue luminescence.

Renilla luciferase and the other coelenterate and ctenophore luciferases, such as the aequorin photoprotein, use imidazopyrazine substrates, particularly the substrates generically called coelenterazine [see, formulae (I) and (II), above]. Other genera that have luciferases that use a coelenterazine include: squid, such as Chiroteuthis, Eucleoteuthis, Onychoteuthis, Watasenia; cuttlefish, Sepiolina; shrimp, such as Oplophorus, Sergestes, and Gnathophausia; deep-sea fish, such as Argyropelecus, Yarella, Diaphus, and Neoscopelus.

Renilla luciferase does not, however, have bound oxygen, and thus requires dissolved oxygen in order to produce light in the presence of a suitable luciferin substrate. Since Renilla luciferase acts as a true enzyme [i.e., it does not have to be reconstituted for further use] the resulting luminescence can be long-lasting in the presence of saturating levels of luciferin. Also, Renilla luciferase is relatively stable to heat.

Renilla luciferase, DNA encoding Renilla luciferase, and use of the DNA to produce recombinant luciferase, as well as DNA encoding luciferase from other coelenterates, are well known and available [see, e.g., SEQ ID No. 1, U.S. Pat. Nos. 5,418,155 and 5,292,658; see, also, Prasher et al. (1985) *Biochem. Biophys. Res. Commun.* 126:1259–1268; Cormier (1981) "Renilla and Aequorea bioluminescence" in *Bioluminescence and Chemiluminescence*, pp. 225–233; Charbonneau et al. (1979) *J. Biol. Chem.* 254:769–780; Ward et al. (1979) *J. Biol. Chem.* 254:781–788; Lorenz et al. (1981) *Proc. Natl. Acad. Sci. U.S.A.* 88: 4438–4442; Hori et al. (1977) *Proc. Natl. Acad. Sci. U.S.A.* 74:4285–4287; Hori et al. (1975) *Biochemistry* 14:2371–2376; Hori et al. (1977) *Proc. Natl. Acad. Sci. U.S.A.* 74:4285–4287; Inouye et al. (1975) *Jap. Soc. Chem. Lett.*141–144; and Matthews et al. (1979) *Biochemistry* 16:85–91]. The DNA encoding Renilla luciferase and host cells containing such DNA provide a convenient means for producing large quantities of the enzyme [see, e.g., U.S. Pat. Nos. 5,418,155 and 5,292,658, which describe recombinant production of Renilla luciferase and the use of the DNA to isolate DNA encoding other luciferases, particularly those from related organisms]. A modified version of a method [U.S. Pat. Nos. 5,418,155 and 5,292,658] for the recombinant production of Renilla luciferase that results in a higher level of expression of the recombinant enzyme is presented in the EXAMPLES herein.

When used herein, the Renilla luciferase can be packaged, such as in an toy, in lyophilized form, encapsulated in a vehicle, either by itself or in combination with the luciferin substrate. Prior to use the mixture is contacted with an aqueous composition, preferably a phosphate buffered saline or other suitable buffer, such a Tris-based buffer [such as 0.1 mm Tris, 0.1 mm EDTA] pH 7–8, preferably about pH 8; dissolved $O_2$ will activate the reaction. Addition of glycerol [about 1%] increases light intensity. Final concentrations of luciferase in the glowing mixture will be on the order of 0.01 to 1 mg/l or more. Concentrations of luciferin will be at least about $10^{-8}$ M, but 1 to 100 or more orders of magnitude higher to produce a long lasting bioluminescence.

In certain embodiments herein, about 1 to 10 mg, or preferably 2–5 mg, more preferably about 3 mg of coelenterazine will be used with about 100 mg of Renilla luciferase. The precise amounts, of course can be determined empirically, and, also will depend to some extent on the ultimate concentration and application. In particular, about addition of about 0.25 ml of a crude extract from the bacteria that express Renilla to 100 ml of a suitable assay buffer and about 0.005 μg was sufficient to produce a visible and lasting glow [see, U.S. Pat. Nos. 5,418,155 and 5,292, 658, which describe recombinant production of Renilla luciferase].

Lyophilized mixtures, and compositions containing the Renilla luciferase are also provided. The luciferase or mixtures of the luciferase and luciferin may also be encapsulated into a suitable delivery vehicle, such as a liposome, glass particle, capillary tube, drug delivery vehicle, gelatin, time release coating or other such vehicle. Kits containing these mixtures, compositions, or vehicles and also a selected article of manufacture, such as a toy gun, bubble composition, balloon, item of clothing, personal item, are also provided. The luciferase may also be linked to a substrate, such as cotton, polyester, polyester-cotton blends, polypropylene, polyvinyltoluene, polyvinyl propylene, glass, ceramic, or plastics are provided in combination with or as part of an article of manufacture.

3. Crustacean, Particularly Cyrpidina Systems

The ostracods, such as *Vargula serratta, hilgendorfii* and *noctiluca* are small marine crustaceans, sometimes called sea fireflies. These sea fireflies are found in the waters off the coast of Japan and emit light by squirting luciferin and luciferase into the water, where the reaction, which produces a bright blue luminous cloud, occurs. The reaction involves only luciferin, luciferase and molecular oxygen, and, thus, is very suitable for application herein.

The systems, such as the Vargula bioluminescence generating systems, are particularly preferred herein because the components are stable at room temperature if dried and powdered and will continue to react even if contaminated. Further, the bioluminescent reaction requires only the luciferin/luciferase components in concentrations as low as 1:40 parts per billion to 1:100 parts per billion, water and molecular oxygen to proceed. An exhausted system can be renewed by addition of luciferin.

a. Vargula luciferase

Vargula luciferase is a 555-amino acid polypeptide that has been produced by isolation from Vargula and also using recombinant technology by expressing the DNA in suitable bacterial and mammalian host cells [see, e.g., Thompson et al. (1989) *Proc. Natl. Acad. Sci. U.S.A.* 86:6567–6571; Inouye et al. (1992) *Proc. Natl. Acad. Sci. U.S.A.* 89:9584–9587; Johnson et al. (1978) *Methods in Enzymology* LVII:331–349; Tsuji et al. (1978) *Methods Enzymol.* 57:364–72; Tsuji (19740 *Biochemistry* 13:5204–5209; Japanese Patent Application No. JP 3-30678 Osaka; and European Patent Application No. EP 0 387 355 A1].

(1) Purification from Cypridina

Methods for purification of Vargula [Cypridina] luciferase are well known. For example, crude extracts containing the active can be readily prepared by grinding up or crushing the Vargula shrimp. In other embodiments, a preparation of *Cypridina hilgendorfi* luciferase can be prepared by immersing stored frozen *C. hilgendorfi* in distilled water containing, 0.5–5.0 M salt, preferably 0.5–2.0 M sodium or potassium chloride, ammonium sulfate, at 0–30° C., preferably 0–10° C., for 1–48 hr, preferably 10–24 hr, for extraction followed by hydrophobic chromatography and then ion exchange or affinity chromatography [TORAY IND INC, Japanese patent application JP 4258288, published Sep. 14, 1993; see, also, Tsuji et al. (1978) *Methods Enzymol.* 57:364–72 for other methods].

The luciferin can be isolated from ground dried Vargula by heating the extract, which destroys the luciferase but leaves the luciferin intact [see, e.g., U.S. Pat. No. 4,853, 327].

(2) Preparation by Recombinant Methods

The luciferase is preferably produced by expression of cloned DNA encoding the luciferase [European Patent Application NO. 0 387 355 A1; International PCT Application No. WO90/01542; see, also SEQ ID No. 5, which sets forth the sequence from Japanese Patent Application No. JP 3–30678 and Thompson et al. (1989) *Proc. Natl. Acad. Sci. U.S.A.* 86:6567–6571] DNA encoding the luciferase or variants thereof is introduced into *E. coli* using appropriate vectors and isolated using standard methods.

b. Vargula Luciferin

The natural luciferin in a substituted imidazopyrazine nucleus, such a compound of formula (III):

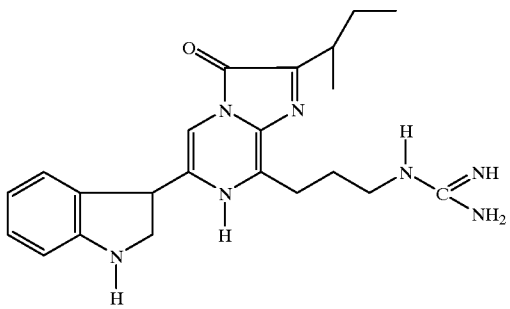

Analogs thereof and other compounds that react with the luciferase in a light producing reaction also may be used.

Other bioluminescent organisms that have luciferases that can react with the Vargula luciferin include, the genera Apogon, Parapriacanthus and Porichthys.

c. Reaction

The luciferin upon reaction with oxygen forms a dioxetanone intermediate [which includes a cyclic peroxide similar to the firefly cyclic peroxide molecule intermediate]. In the final step of the bioluminescent reaction, the peroxide breaks down to form $CO_2$ and an excited carbonyl. The excited molecule then emits a blue to blue-green light.

The optimum pH for the reaction is about 7. For purposes herein, any pH at which the reaction occurs may be used. The concentrations of reagents are those normally used for analytical reactions or higher [see, e.g., Thompson et al. (1990) *Gene* 96:257–262]. Typically concentrations of the luciferase between 0.1 and 10 mg/l, preferably 0.5 to 2.5 mg/l will be used. Similar concentrations or higher concentrations of the luciferin may be used.

4. Insect Bioluminescence Generating Systems Including Firefly, Click Beetle, and Other Insect Systems The biochemistry of firefly bioluminescence was the first bioluminescence generating system to be characterized [see, e.g., Wienhausen et al. (1985) *Photochemistry and Photobiology* 42:609–611; McElroy et al. (1966) in *Molecular Architecture in Cell Physiology,* Hayashi et al., eds. Prentice Hall, Inc., Englewood Cliffs, N.J., pp. 63–80] and it is commercially available [e.g., from Promega Corporation, Madison, Wis., see, e.g., Leach et al. (1986) *Methods in Enzymology* 133:51–70, esp. Table 1]. Luciferases from different species of fireflies are antigenically similar. These species include members of the genera Photinus, Photurins and Luciola. Further, the bioluminescent reaction produces more light at 30° C. than at 20° C., the luciferase is stabilized by small quantities of bovine albumin serum, and the reaction can be buffered by tricine.

a. Luciferase

DNA clones encoding luciferases from various insects and the use to produce the encoded luciferase is well known.

For example, DNA clones that encode luciferase from *Photinus pyralis, Luciola cruciata* [see, e.g., de Wet et al. (1985) *Proc. Natl. Acad. Sci. U.S.A.* 82:7870–7873; de We et al. (1986) *Methods in Enzymology* 133:3; U.S. Pat. No. 4,968,613, see, also SEQ ID No. 3] are available. The DNA has also been expressed in Saccharomyces [see, e.g., Japanese Application No. JP 63317079, published Dec. 26, 1988, KIKKOMAN CORP] and in tobacco.

In addition to the wild-type luciferase modified insect luciferases have been prepared. For example, heat stable luciferase mutants, DNA-encoding the mutants, vectors and transformed cells for producing the luciferases are available. A protein with 60% amino acid sequence homology with luciferases from *Photinus pyralis, Luciola mingrelica, L. cruciata* or *L. lateralis* and having luciferase activity is available [see, e.g., International PCT Application No. WO95/25798]. It is more stable above 30° C. than naturally-occurring insect luciferases and may also be produced at 37° C. or above, with higher yield.

Modified luciferases that generate light at different wavelengths [compared with native luciferase], and thus, may be selected for their color-producing characteristics. For example, synthetic mutant beetle luciferase(s) and DNA encoding such luciferases that produce bioluminescence at a wavelength different from wild-type luciferase are known [Promega Corp, International PCT Application No. WO95/18853, which is based on U.S. application Ser. No. 08/177, 081 Jan. 3, 1994]. The mutant beetle luciferase has an amino acid sequence differing from that of the corresponding wild-type *Luciola cruciata* [see, e.g., U.S. Pat. Nos. 5,182, 202, 5,219,737, 5,352,598, see, also SEQ ID No. 3] by a substitution(s) at one or two positions. The mutant luciferase produces a bioluminescence with a wavelength of peak intensity that differs by at least 1 nm from that produced by wild-type luciferases.

Other mutant luciferase have also been produced. Mutant luciferases with the amino acid sequence of wild-type luciferase, but with at least one mutation in which valine is replaced by isoleucine at the amino acid number 233, valine by isoleucine at 239, serine by asparagine at 286, glycine by serine at 326, histidine by tyrosine at 433 or proline by serine at 452 are known [see, e.g., U.S. Pat. Nos. 5,219,737, and 5,330,906]. The luciferases are produced by expressing DNA-encoding each mutant luciferase in *E. coli* and isolating the protein. These luciferases produce light with colors that differ from wild-type. The mutant luciferases catalyze luciferin to produce red [λ 609 nm and 612 nm], orange [λ595 and 607 nm] or green [λ 558 nm] light. The other physical and chemical properties of mutant luciferase are substantially identical to native wild type-luciferase. The mutant luciferase has the amino acid sequence of *Luciola cruciata* luciferase with an alteration selected from Ser 286 replaced by Asn, Gly 326 replaced by Ser, His 433 replaced by Tyr or Pro 452 replaced by Ser. Thermostable luciferases are also available [see, e.g., U.S. Pat. No. 5,229,285; see, also International PCT Application No. WO95/25798, which provides Photinus luciferase in which the glutamate at position 354 is replaced lysine and Luciola luciferase in which the glutamate at 356 is replaced with lysine].

These mutant luciferases as well as the wild type luciferases are among those preferred herein, particularly in instances when a variety of colors are desired or when stability at higher temperatures is desired. It is also noteworthy that firefly luciferases have alkaline pH optima [7.5–9.5], and, thus, are suitable for use in combination with articles of manufacture, such as the bubble compositions that have alkaline pH.

b. Luciferin

The firefly luciferin is a benzothiazole:

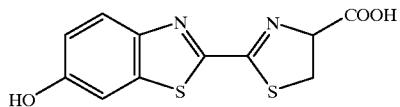

Analogs of this luciferin and synthetic firefly luciferins are also known to those of skill in art [see, e.g., U.S. Pat. Nos. 5,374,534 and 5,098,828]. These include compounds of formula (IV) [see, U.S. Pat. No. 5,098,828]:

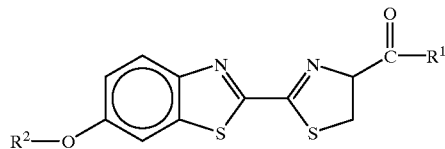

in which:

$R^1$ is hydroxy, amino, linear or branched $C_1$–$C_{20}$ alkoxy, $C_2$–$C_{20}$ alkyenyloxy, an L-amino acid radical bond via the α-amino group, an oligopeptide radical with up to ten L-amino acid units linked via the α-amino group of the terminal unit;

$R^2$ is hydrogen, $H_2PO_3$, $HSO_3$, unsubstituted or phenyl substituted linear or branched $C_1$–$C_{20}$ alkyl or $C_2$–$C_{20}$ alkenyl, aryl containing 6 to 18 carbon atoms, or $R^3$—C(O)—; and $R^3$ is an unsubstituted or phenyl substituted linear or branched $C_1$–$C_{20}$ alkyl or $C_2$–$C_{20}$ alkenyl, aryl containing 6 to 18 carbon atoms, a nucleotide radical with 1 to 3 phosphate groups, or a glycosidically attached mono- or disaccharide, except when formula (IV) is a D-luciferin or D-luciferin methyl ester.

c. Reaction

The reaction catalyzed by firefly luciferases and related insect luciferases requires ATP, $Mg^{2+}$ as well as molecular oxygen. Luciferin must be added exogenously. Firefly luciferase catalyzes the firefly luciferin activation and the subsequent steps leading to the excited product. The luciferin reacts with ATP to form a luciferyl adenylate intermediate. This intermediate then reacts with oxygen to form a cyclic luciferyl peroxy species, similar to that of the coelenterate intermediate cyclic peroxide, which breaks down to yield $CO_2$ and an excited state of the carbonyl product. The excited molecule then emits a yellow light; the color, however, is a function of pH. As the pH is lowered the color of the bioluminescence changes from yellow-green to red.

Different species of fireflies emit different colors of bioluminescence so that the color of the reaction will be dependent upon the species from which the luciferase is obtained. Additionally, the reaction is optimized at pH 7.8.

Addition of ATP and luciferin to a reaction that is exhausted produces additional light emission. Thus, the system, once established, is relatively easily maintained. Therefore, it is highly suitable for use herein in embodiments in which a sustained glow is desired or reuse of the item is contemplated. Thus, the components of a firefly system can be packaged with the item of manufacture, such as a toy gun, and then combined with the article before use. For example, the luciferin and ATP can be added to a mild bubble or a protein composition that contains luciferase each time the bubbles are used.

5. Bacterial Systems

Luminous bacteria typically emit a continuous light, usually blue-green. When strongly expressed, a single bacterium may emit $10^4$ to $10^5$ photons per second. Bacterial bioluminescence systems include, among others, those systems found in the bioluminescent species of the genera Photobacterium, Vibrio and Xenorhabdus. These systems are well known and well characterized [see, e.g., Baldwin et al. (1984) *Biochemistry* 23:3663–3667; Nicoli et al. (1974) *J. Biol. Chem.* 249:2393–2396; Welches et al. (1981) *Biochemistry* 20:512–517; Engebrecht et al. (1986) *Methods in Enzymology* 133:83–99; Frackman et al. (1990) *J. of Bacteriology* 172:5767–5773; Miyamoto et al. (1986) *Methods in Enzymology* 133:70; U.S. Pat. No. 4,581,335].

a. Luciferases

Bacterial luciferase, as exemplified by luciferase derived from *Vibrio harveyi* [EC 1.14.14.3, alkanol reduced-FMN-oxygen oxidoreductase 1-hydroxylating, luminescing], is a mixed function oxidase, formed by the association of two different protein subunits α and β. The α-subunit has an apparent molecular weight of approximately 42,000 kD and the β-subunit has an apparent molecular weight of approximately 37,000 kD [see, e.g., Cohn et al. (1983) *Proc. Natl. Acad. Sci. U.S.A.* 80:120–123]. These subunits associate to form a 2-chain complex luciferase enzyme, which catalyzes the light emitting reaction of bioluminescent bacteria, such as *Vibrio harveyi* [U.S. Pat. No. 4,581,335; Belas et al. (1982) *Science* 218:791–793], *Vibrio fischeri* [Engebrecht et al. (1983) *Cell* 32:773–781; Engebrecht et al. (1984) *Proc. Natl. Acad. Sci. U.S.A.* 81:4154–4158] and other marine bacteria.

Bacterial luciferase genes have been cloned [see, e.g., U.S. Pat. No. 5,221,623; U.S. Pat. No. 4,581,335; European Patent Application No. EP 386 691 A]. Plasmids for expression of bacterial luciferase, such as *Vibrio harveyi*, include pFIT001 (NRRL B-18080), pPALE001 (NRRL B-18082) and pMR19 (NRRL B-18081)] are known. For example the sequence of the entire lux regulon from *Vibiro fisheri* has been determined [Baldwin et al. (1984), *Biochemistry* 23:3663–3667; Baldwin et al. (1981) *Biochem.* 20: 512–517; Baldwin et al. (1984) *Biochem.* 233663–3667; see, also, e.g., U.S. Pat. Nos. 5,196,318, 5,221,623, and 4,581, 335]. This regulon includes luxI gene, which encodes a protein required for autoinducer synthesis [see, e.g., Engebrecht et al. (1984) *Proc. Natl. Acad. Sci. U.S.A.* 81:4154–4158], the luxC, luxD, and luxE genes, which encode enzymes that provide the luciferase with an aldehyde substrate, and the luxA and luxB genes, which encode the alpha and beta subunits of the luciferase.

Lux genes from other bacteria have also been cloned and are available [see, e.g., Cohn et al. (1985) *J. Biol. Chem.* 260:6139–6146; U.S. Pat. No. 5,196,524, which provides a fusion of the luxA and luxB genes from *Vibrio harveyi*]. Thus, luciferase alpha and beta subunit-encoding DNA is provided and can be used to produce the luciferase. DNA encoding the α [1065 bp] and β [984 bp] subunits, DNA encoding a luciferase gene of 2124 bp, encoding the alpha and beta subunits, a recombinant vector containing DNA encoding both subunits and a transformed *E. coli* and other bacterial hosts for expression and production of the encoded luciferase are available. In addition, bacterial luciferases are commercially available.

b. Luciferins

Bacterial luciferins include:

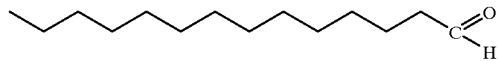

or

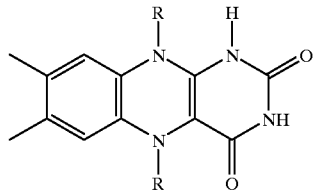

R is, for example, 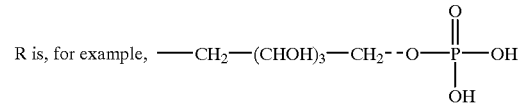

in which the tetradecanal with reduced flavin mononucleotide are considered luciferin since both are oxidized during the light emitting reaction.

c. Reactions

The bacterial systems require, in addition to reduced flavin, five polypeptides to complete the bioluminescent reaction: two subunits, α and β, of bacterial luciferin and three units of a fatty acid reductase -system complex, which supplies the tetradecanal aldehyde. Examples of bacterial bioluminescence generating systems useful in the apparatus and methods provided herein include those derived from *Vibrio fisheri* and *Vibrio harveyi*. One advantage to this system is its ability to operate at cold temperatures. It will thus be particularly amenable to use in ice cubes. All components of a bacterial system can be frozen into ice cubes. As it the ice cubes melt into a warmer beverage, which has dissolved $O_2$, the reaction will proceed, thereby providing a sustained glow.

Bacterial luciferase catalyzes the flavin-mediated hydroxylation of a long-chain aldehyde to yield carboxylic acid and an excited flavin; the flavin decays to ground state with the concomitant emission of blue green light [$\lambda_{max}$=490 nm; see, e.g., Legocki et al. (1986) *Proc. Natl. Acad. Sci. USA* 81:9080; see U.S. Pat. No. 5,196,524]:

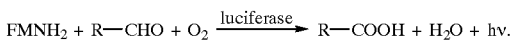

The reaction can be initiated by contacting reduced flavin mononucleotide [$FMNH_2$] with a mixture of the bacterial luciferase, oxygen, and a long-chain aldehyde, usually n-decyl aldehyde.

DNA encoding luciferase from the fluorescent bacterium *Alteromonas hanedai* is known [CHISSO CORP; see, also, Japanese application JP 7222590, published Aug. 22, 1995]. The reduced flavin mononucleotide [FMNH2; luciferin] reacts with oxygen in the presence of bacterial luciferase to produce an intermediate peroxy flavin. This intermediate reacts with a long-chain aldehyde [tetradecanal] to form the acid and the luciferase-bound hydroxy flavin in its excited state. The excited luciferase-bound hydroxy flavin then emits light and dissociates from the luciferase as the oxidized flavin mononucleotide [FMN] and water. In vivo FMN is reduced again and recycled, and the aldehyde is regenerated from the acid.

Flavin reductases have been cloned [see, e.g., U.S. Pat. No. 5,484,723; see, SEQ ID No. 14 for a representative sequence from this patent]. These as well as NAD(P)H can be included in the reaction to regenerate $FMNH_2$ for reaction with the bacterial luciferase and long chain aldehyde. The flavin reductase catalyzes the reaction of FMN, which is the luciferase reaction, into $FMNH_2$; thus, if luciferase and the reductase are included in the reaction system, it is possible to maintain the bioluminescent reaction. Namely, since the bacterial luciferase turns over many times, bioluminescence continues as long as a long chain aldehyde is present in the reaction system.

The color of light produced by bioluminescent bacteria also results from the participation of a protein blue-florescent protein [BFP] in the bioluminescence reaction. This protein, which is well known [see, e.g., Lee et al. (1978) *Methods in Enzymology LVII*:226–234], and may also be added to bacterial bioluminescence reactions in order to cause a shift in the color.

6. Other Systems a. Dinoflagellate Bioluminescence generating Systems

In dinoflagellates, bioluminescence occurs in organelles termed scintillons. These organelles are outpocketings of the cytoplasm into the cell vacuole. The scintillons contain only dinoflagellate luciferase and luciferin [with its binding protein], other cytoplasmic components being somehow excluded. The dinoflagellate luciferin is a tetrapyrrole related to chlorophyll:

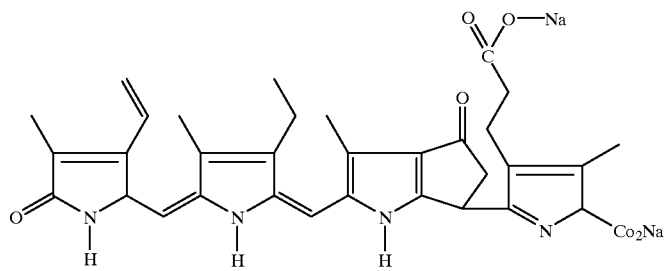

or an analog thereof.

The luciferase is a 135 kD single chain protein that is active at pH 6.5, but inactive at pH 8 [see, e.g., Hastings (1981) *Bioluminescence and Chemiluminescence,* DeLuca et al., eds. Academic Press, NY, pp.343–360]. Luminescent activity can be obtained in extracts made at pH 8 by shifting the pH from 8 to 6. This occurs in soluble and particulate fractions. Within the intact scintillon, the luminescent flash occurs for ~100 msec, which is the duration of the flash in vivo. In solution, the kinetics are dependent on dilution, as in any enzymatic reaction. At pH 8, the luciferin is bound to a protein [luciferin binding protein] that prevents reaction of the luciferin with the luciferase. At pH 6, however, the luciferin is released and free to react with the enzyme.

b. Systems from Molluscs, Such as Latia and Pholas

Molluscs *Latia neritoides* and species of Pholas are bioluminescent animals. The luciferin has the structure:

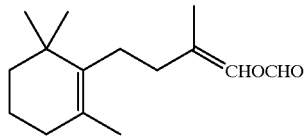

and has been synthesized [see, e.g., Shimomura et al. (1968) *Biochemistry* 7:1734–1738; Shimomura et al. (1972) *Proc. Natl. Acad. Sci. U.S.A.* 69:2086–2089]. In addition to a luciferase and luciferin the reaction has a third component, a "purple protein". The reaction, which can be initiated by an exogenous reducing agent is represented by the following scheme:

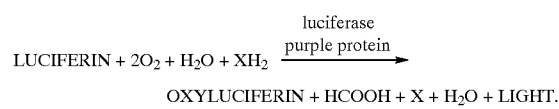

$XH_2$ is a reducing agent.

Thus for practice herein, the reaction will require the purple protein as well as a reducing agent.

c. Earthworms and Other Annelids

Earthworm species, such as Diplocardia longa, Chaetopterus and Harmothoe, exhibit bioluminescence. The luciferin has the structure:

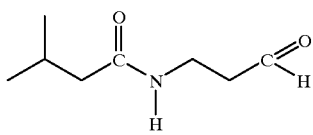

The reaction requires hydrogen peroxide in addition to luciferin and luciferase. The luciferase is a photoprotein.

d. Glow Worms

The luciferase/luciferin system from the glow worms that are found in New Zealand caves, Australia and those found in Great Britain are also intended for use herein.

e. Marine Polycheate Worm Systems

Marine polycheate worm bioluminescence generating systems, such as Phyxotrix and Chaetopterus, are also contemplated for use herein.

f. South American Railway Beetle

The bioluminescence generating system from the South American railway beetle is also intended for use herein.

g. Fish

Of interest herein, are luciferases and bioluminescence generating systems that generate red light. These include luciferases found in species of Aristostomias, such as *A. scintillans* [see, e.g., O'Day et al. (1974) *Vision Res.* 14:545–550], Pachystomias, Malacosteus, such as *M. niger.*

7. Fluorescent Proteins

Fluorescent proteins (FPs), particularly green fluorescent proteins (GFPs), such as those from Aquorea and Renilla, and other related proteins can be used in combination with any of the novelty items provided herein, including toys, beverages, foods, cosmetics, paper products and others. The FPs may be used alone with these items or may be added to bioluminescence generating systems or items with such systems as a means of altering the color of the items. Mutein GFPs from Aquorea are also known (see, e.g., U.S. Pat. No. 5,625,048).

a. Green and Blue Fluorescent Proteins

Blue light is produced using the Renilla luciferase or the Aequorea photoprotein in the presence of $Ca^{2+}$ and the coelenterazine luciferin or analog thereof. This light can be converted into a green light if a green fluorescent protein (GFP) is added to the reaction. Green fluorescent proteins, which have been purified [see, e.g., Prasher et al. (1992) *Gene* 111:229–233] and also cloned [see, e.g., International PCT Application No. WO 95/07463, which is based on U.S. application Ser. No. 08/119,678 and U.S. application Ser. No. 08/192,274, which are herein incorporated by reference], are energy-transfer acceptors. GFPs fluoresce in vivo upon receiving energy from a luciferase-oxyluciferin excited-state complex or a $Ca^{2+}$-activated photoprotein. The chromophore is formed from modified amino acid residues within the polypeptide.

The best characterized GFPs are those of Aequorea and Renilla [see, e.g., Prasher et al. (1992) *Gene* 111:229–233; Hart, et al. (1979) *Biochemistry* 18:2204–2210]. For example, a green fluorescent protein [GFP] from *Aequorea victoria* contains 238 amino acids, absorbs blue light and emits green light.

Thus, for example, inclusion of this protein in a composition containing the aequorin photoprotein charged with coelenterazine and oxygen, can, in the presence of calcium, result in the production of green light. It is contemplated that GFPs may be included in the bioluminescence generating reactions that employ the aequorin or Renilla luciferases or other suitable luciferase in order to enhance or alter color of the resulting bioluminescence.

GFPs are activated by blue light to emit green light and thus may be used in the absence of luciferase and in conjunction with an external light source with novelty items, as described herein. Similarly, blue fluorescent proteins (BFPs), such as from *Vibrio fischeri*, *Vibrio harveyi* or *Photobacterium phosphoreum*, may be used in conjunction with an external light source of appropriate wavelength to generate blue light. (See for example, Karatani, et al., "A blue fluorescent protein from a yellow-emitting luminous bacterium," *Photochem. Photobiol.* 55(2):293–299 (1992); Lee, et al., "Purification of a blue-fluorescent protein from the bioluminescent bacterium *Photobacterium phosphoreum*" *Methods Enzymol.* (Biolumin. Chemilumin.) 57:226–234 (1978); and Gast, et al. "Separation of a blue fluorescence protein from bacterial luciferase" *Biochem. Biophys. Res. Commun.* 80(1):14–21 (1978), each, as all references cited herein, incorporated in its entirety by reference herein.) In particular, GFPs, and/or BFPs or other such fluorescent proteins may be used in the beverage and/or food combinations provided herein and served in rooms illuminated with light of an appropriate wavelength to cause the fluorescent proteins to fluoresce.

GFPs and/or BFPs or other such fluorescent proteins may be used in any of the novelty items and combinations provided herein, such as the beverages and toys, including bubble making toys, particularly bubble-making compositions or mixtures and cosmetics. Such systems are particularly of interest because no luciferase is needed to activate the photoprotein and because the proteins are readily digested. These fluorescent proteins may also be used in addition to bioluminescence generating systems to enhance or create an array of different colors.

These proteins may be used alone or in combination with bioluminescence generating systems to produce an array of colors. They may be used in combinations such that the color of, for example, a beverage changes over time, or includes layers of different colors.

b. Phycobiliproteins

Phycobiliproteins are water soluble fluorescent proteins derived from cyanobacteria and eukaryotic algae [see, e.g., Apt et al. (1995) *J. Mol. Biol.* 238:79–96; Glazer (1982) *Ann. Rev. Microbiol.* 36:173–198; and Fairchild et al. (1994) *J. of Biol. Chem.* 269:8686–8694]. These proteins have been used as fluorescent labels in immunoassay [see, Kronick (1986) *J. of Immunolog. Meth.* 92:1–13], the proteins have been isolated and DNA encoding them is also available [see, e.g., Pilot et al. (1984) *Proc. Natl. Acad. Sci. U.S.A.* 81:6983–6987; Lui et al. (1993) *Plant Physiol* 103:293–294; and Houmard et al. (1988) *J. Bacteriol.* 170:5512–5521; the proteins are commercially available from, for example, ProZyme, Inc., San Leandro, Calif.].

In these organisms, the phycobiliproteins are arranged in subcellular structures termed phycobilisomes and function as accessory pigments that participate in photosynthetic reactions by absorbing visible light and transferring the derived energy to chlorophyll via a direct fluorescence energy transfer mechanism.

Two classes of phycobiliproteins are known based on their color: phycoerythrins (red) and phycocyanins (blue), which have reported absorption maxima between 490 and 570 nm and between 610 and 665 nm, respectively. Phycoerythrins and phycocyanins are heterogenous complexes composed of different ratios of alpha and beta monomers to which one or more class of linear tetrapyrrole chromophores are covalently bound. Particular phycobiliproteins may also contain a third γ-subunit which often associated with $(\alpha\beta)_6$ aggregate proteins.

All phycobiliproteins contain either phycothrombilin or phycoerythobilin chromophores, and may also contain other bilins, such as phycourobilin, cryptoviolin or a 697 nm bilin. The γ-subunit is covalently bound with phycourobilin, which results in the 495–500 nm absorbance peak of B- and R-phycoerythrins. Thus, the spectral characteristics of phycobiliproteins may be influenced by the combination of the different chromophores, the subunit composition of the apophycobiliproteins and/or the local environment that affects the tertiary and quaternary structure of the phycobiliproteins.

As described above for GFPs & BFPs, phycobiliproteins are also activated by visible light of the appropriate wavelength and thus may be used in the absence of luciferase and in conjunction with an external light source to illuminate novelty items, particularly, as described herein. In particular, phycobiliproteins may be used in the novelty items, such as beverage and/or food combinations provided herein and served in rooms illuminated with light of an appropriate wavelength to cause the fluorescent proteins to fluoresce. Cosmetics containing these proteins are also contemplated.

As noted above, these proteins may be used in combination with other fluorescent proteins and/or bioluminescence generating systems to produce an array of colors or to provide different colors over time.

Attachment of phycobiliproteins to solid support matrices is known (e.g., see U.S. Pat. Nos. 4,714,682; 4,767,206;

4,774,189 and 4,867,908). Therefore, phycobiliproteins may be coupled to microcarriers coupled to one or more components of the bioluminescent reaction, preferably a luciferase, to convert the wavelength of the light generated from the bioluminescent reaction. Microcarriers coupled to one or more phycobiliproteins may be used in any of the novelty items and combinations provided herein, such as the multicolor beverages and toys, including bubble making toys, particularly bubble-making compositions or mixtures.

C. Practice of the Reactions in Combination with Articles of Manufacture

The particular manner in which each bioluminescence system will be combined with a selected article of manufacture will be a function of the article and the desired effect. In general, however, less than all of the components of the reaction will be provided with the article and then contact with the remaining component(s) to produce a glow. There are a multitude of alternative means for achieving this result; some are described herein, and others will be apparent by virtue of the disclosure herein.

In the simplest embodiments, the organisms can be ground up and dried. For example, light will be emitted by ground up fireflies when mixed with water and ATP. Light will also be emitted merely be combining ground up Vargula shrimp and adding water, preferably cool water [room temperature or lower]. The only caveat is that the water must not be too hot; high temperatures destroy activity of the luciferases.

In other embodiments, the substantially pure reagents are combined with the article of manufacture and the article will glow or spew a glowing spray or jet. The reagents may be provided in compositions, such as suspensions, as powders, as pastes or any in other suitable form. They may be provided as sprays, aerosols, or in any suitable form. The reagents may be linked to a matrix and combined with the article of manufacture or formed into the article of manufacture. Typically all but one or more, though preferably all but one, of the components necessary for the reaction will be mixed and provided together; reaction will be triggered contacting the mixed component(s) with the remaining component(s), such as by adding $Ca^{2+}$, FMN with reductase, $FMNH_2$, ATP, air or oxygen. The resulting matrix materials are advantageously used in connection numerous novelty items, such as clothing. They are also used in the cartridges provided herein.

In preferred embodiments the luciferase or luciferase/luciferin, such as the aequorin photoprotein, will be provided in combination with the article of manufacture or added before use. The article will then be contacted with the remaining components. As will become apparent herein, there are a multitude of ways in which each system may be combined with a selected article of manufacture.

D. Packaging of Bioluminescence Systems

Packaging for bioluminescence generating reagents provided herein must be chosen according to the article of manufacture with which the reagents are to be combined. In general, the packaging is non-reactive with the compositions contained therein and must exclude water and or air to the degree those substances are required for the luminescent reaction to proceed. It will be appreciated, however, that specific uses for the bioluminescence generating systems may require specific packaging. Following are some examples of the special packaging requirements of various end uses of the bioluminescence generating systems. These are offered as examples only and are in no way intended as limiting.

The bioluminescence generating reagents may be provided in pellets, encapsulated as micro or macro-capsules, linked to matrices and included in or on articles of manufacture, or as mixtures in chambers within an article of manufacture or in some other configuration. With respect to other articles of manufacture that include chambers or vessels, such as certain toys, primary considerations are that the bioluminescence generating system be amenable to activation by the user at will and that the container be non-reactive and, if desired, translucent to the bioluminescent glow. Examples of vessels include beverage holders, plates or other dishes, vases, jars, bottles, spray cans and other containers. In general, vessels for use in practicing the methods herein have an enclosed, defined space, that contains most of the components of the bioluminescence generating system, and a separate enclosed, defined space containing the remaining necessary ingredients; such that, the two spaces are separated by a readily removable membrane which, upon removal, permits the components to mix and thereby react, resulting in illumination. Alternatively, the vessel can have a single compartment containing all but the final ingredients of the bioluminescence generating system and being amenable to addition of the final ingredients by the user; for example through an opening in the compartment.

Any toy, vessel or other article of manufacture that is amenable to having a generally translucent covering defining a space for containment of the bioluminescence generating system components and that is amenable to simple manipulation to permit addition of the final components necessary for the illumination reaction is contemplated.

Thus, whether the item that will glow or produce a glowing fluid, jet or spray, is a toy, vessel or other article of manufacture, its general design is the same. At least one of the bioluminescence generating system components is separated from the remaining components. The remaining components are added prior to use. They can be included in the article of manufacture and physically separated from the other components. For example, the physical separation means are those that are readily removed by the user, to permit mixing, resulting in illumination of the components. For example, an article of manufacture may contain a luciferase and substrate in one compartment and a bioluminescence activator in an adjacent compartment; or alternatively, one compartment may contain the luciferase, and the other the substrate luciferin and dissolved oxygen or other requisite activator(s). The compartments are separated by a dividing member, such as a membrane, that, upon compression of the article of manufacture, ruptures permitting separated components to mix and to thereby glow. For suitable embodiments, see EXAMPLES, below [see, also, e.g., containers described in U.S. Pat. Nos. 3,539,794 and 5,171,081].

Other embodiments contemplated herein, include those in which a fluid is ejected as a spray or jet and is rendered bioluminescent prior to ejection from the device, such as a toy or fountain. In general, the methods will involve addition of the bioluminescence generating system components to the water just prior to ejection thereby causing the ejected spray or jet or stream to glow. Various apparatus for accomplishing this are provided herein. In light of the disclosure herein other apparatus can be adapted for such use. Examples include chambers within a toy that inject the components into a water chamber just prior to ejection of the water, or a clip-on device housing the components, perhaps in premeasured amounts, which is attached to the toy and manually or automatically engaged to inject the ingredients into a water chamber. Similarly, the water can be introduced into a chamber containing the components and then ejected.

In other embodiments, the components may be packaged as separate compositions, that, upon mixing, glow. For example, a composition containing luciferase may be provided separately from, and for use with, an a separate composition containing a bioluminescence substrate and bioluminescence activator. In another instance, luciferase and luciferin compositions may be separately provided and the bioluminescence activator may be added after, or simultaneously with, mixing of the other two compositions.

Similarly, the luciferase and bioluminescence substrate may be provided in a single packaging apparatus, an composition that is a mixture, suspension, solution, powder, paste or other suitable composition, that is designed to exclude the necessary bioluminescence activator. Upon addition of the bioluminescence activator to the remaining components or upon addition of the components to the bioluminescence activator, the reaction commences and the mixture glows. One example of such a system is "fairy dust". In this embodiment the luciferase and bioluminescence substrate, for example, are packaged to exclude water and/or air, the bioluminescence activator. Release of the components from the packaging into the air and/or moisture in the air activates the components thereby generating luminescence. Another example is packaging the luciferase and substrate in the cap apparatus of a vessel, such that operation of the cap apparatus releases the components into the composition contained in the vessel, causing it to glow.

1. Dispensing and Packaging Apparatus for Combination with the Bioluminescence generating system Components In one aspect, the bioluminescent apparatus systems provided herein are bioluminescence [or bioluminescent] systems in combination with dispensing or packaging apparatus. The bioluminescence systems, described in detail elsewhere herein, include three components: a bioluminescence substrate [e.g., a luciferin], a luciferase [e.g., a luciferase or photoprotein], and a bioluminescence activator or activators [e.g., molecular oxygen or $Ca^{2+}$]. The dispensing and packaging apparatus are configured to keep at least one of the three components separate from the other two components, until generation of bioluminescence is desired.

In general, the dispensing and packaging apparatus are non-reactive with the bioluminescence generating system components contained therein and can exclude moisture, air or other activators, such as $O_2$ or $Ca^{2+}$, or in some manner keep all necessary components that are required for the bioluminescent reaction to come into contact until desired.

It will be appreciated, however, that specific applications and configurations of the bioluminescence systems may require specific apparatus. Following are exemplary descriptions of various dispensers and packages contemplated for use herein. These are offered as examples only and are in no way intended as limiting. It is understood that in light of the description herein, other apparatus may be modified or devised, that would be suitable for use to produce bioluminescence in combination with novelty items.

2. Capsules, Pellets, Liposomes, Endosomes, Vacuoles, Micronized Particles

Certain embodiments of the novelty item combinations provided herein require sequestering of the components from the environment prior to use or require the components to be provided in particulate form. Examples of such embodiments include beverages, foods and particles, such as for use as fairy dust or in toy guns, fountains of particles and other such applications. In particular, embodiments in which the bioluminescence generating system is manufactured as part of food or beverage producing glowing beverages or foods require specific packaging considerations. To be amenable to use as an additive to beverages for human consumption, the packaging must be non-toxic, and should be easy to open to provide for contact of the bioluminescence generating system components with the beverage. Examples of suitable packaging for such use include encapsulating the bioluminescence generating system components in one or micro- [up to about 100 μm in size] or macroparticles [larger than 100 μM] of material that permits release of the contents, such as by diffusion or by dissolution of the encapsulating material. Liposomes and other encapsulating vehicles [see, e.g., U.S. Pat. No. 4,525,306, which describes encapsulation of compounds in gelatin; U.S. Pat. Nos. 4,021,364, 4,225,581, 4,269,821, 4,322,311, 4,324,683, 4,329,332, 4,525,306, 4,963,368 describe encapsulation of biologically active materials in various polymers] known to those of skill in the art, including those discussed herein and known to those of skill in the art [such as soluble paper, see U.S. Pat. No. 3,859,125]. Likewise, packaging of the system components for addition to food products must address the same considerations. The components may be added to the food substance directly, e.g., by sprinkling the dried and powdered ingredients onto the food, or indirectly, e.g., via addition, to the food, of a capsule containing the ingredients.

a. Encapsulating Vehicles in General

All components of the bioluminescence generating system, except for the oxygen or water or $Ca^{2+}$, depending upon the selected system can be incorporated into encapsulating material, such as liposomes, that protect the contents from the environment until placed into conditions that cause release of the contents into the environment. Encapsulating material contemplated for use herein includes liposomes and other such materials used for encapsulating chemicals, such as drug delivery vehicles.

b. Encapsulating Vehicles—Liposomes

For example, liposomes that dissolve and slowly release the components into the selected beverage, which contains dissolved oxygen or $Ca^{2+}$ or even ATP for the luciferase system are contemplated herein. They can be formulated in compositions, such as solutions, suspensions, gels, lotions, creams, and ointments. Liposomes and other slow release encapsulating compositions are well known and can be adapted for use in for slow release delivery of bioluminescence generating components. Typically the luciferin and luciferase will be encapsulated in the absence of oxygen or $Ca^{2+}$ or ATP or other activating component. Upon release into the environment or medium containing this component at a suitable concentration, the reaction will proceed and a glow will be produced. Generally the concentrations of encapsulated components should be relatively high, perhaps 0.1–1 mg/ml or more, to ensure high enough local concentrations upon release to be visible.

Liposomes or other sustained release delivery system that are formulated in an ointment or sustained release topical vehicle, for example, would be suitable for use in a body paint, lotion. Those formulated as a suspension would be useful as a spray. Numerous ointments and suitable liposome formulations are known [see, e.g., Liposome Technology, Targeted Drug Delivery and Biological Interaction, vol. III, G. Gregoriadis ed., CRC Press, Inc., 1984; U.S. Pat. Nos. 5,470,881; 5,366,881; 5,296,231; 5,272,079; 5,225,212; 5,190,762; 5,188,837; 5,188,837; 4,921,757; 4,522,811]. For example, an appropriate ointment vehicle would contain petrolatum, mineral oil and/or anhydrous liquid lanolin. Sustained release vehicles such as liposomes, membrane or contact lens delivery systems, or gel-forming plastic polymers would also be suitable delivery vehicles. Liposomes for topical delivery are well known [see, e.g., U.S. Pat. No. 5,296,231; Mezei et al. (1980) "Liposomes—A selective drug delivery system for the topical route of administration, I. lotion dosage form" *Life Sciences* 26:1473–1477; Mezei et al. (1981) "Liposomes—A selective drug delivery system for the topical route of administration: gel dosage form" *Journal of Pharmacy and Pharmacology* 34:473–474; Gesztes et al. (1988) "Topical anaesthesia of the skin by liposome-encapsulated tetracaine" *Anesthesia and Analgesia* 67:1079–1081; Patel (1985) "Liposomes as a controlled-release system", *Biochemical Soc. Trans.* 13:513–516; Wohirab et al. (1987) "Penetration kinetics of liposomal hydrocortisone in human skin" *Dermatologica* 174:18–22].

Liposomes are microcapsules [diameters typically on the order of less than 0.1 to 20 μm] that contain selected mixtures and can slowly release their contents in a sustained release fashion. Liposomes or other capsule, particularly a time release coating, that dissolve upon exposure to oxygen, air, moisture, visible or ultraviolet [UV] light or a particular pH or temperature [see, e., U.S. Pat. No. 4,882,165; Kusumi et al. (1989) *Chem. Lett.* no.3 433–436; Koch Troels et al. (1990) *Bioconjugate Chem.* 4:296–304; U.S. Pat. No. 5,482,719; U.S. Pat. No. 5,411,730; U.S. Pat. No. 4,891,043; Straubinger et al. (1983) *Cell* 32:1069–1079; and Straubinger et al. (1985) *FEBS Lttrs.* 179:148–154; and Duzgunes et al. in Chapter 11 of the book CELL FUSION, edited by A. E. Sowers; Ellens et al. (1984) *Biochemistry* 23:1532–1538; Yatvin et al. (1987) *Methods in Enzymology* 149:77–87] may be used for example in the squirt guns or toy machine guns or fairy dust or toy cigarettes. Liposome formulations for use in baking [see, e.g., U.S. Pat. No. 4,999,2081 are available. They release their contents when eaten or heated. Such liposomes may be suitable for incorporation into food products herein or in embodiments in which release of the components by heating is desired.

Liposomes be prepared by methods known to those of skill in the art [see, e.g., Kim et al. (1983) *Bioch. Bioph. Acta* 728:339–348; Assil et al. (1987) *Arch Ophthalmol.* 105:400; and U.S. Pat. No. 4,522,811, and other citations herein and known to those of skill in the art].

Liposomes that are sensitive to low pH [see, e.g., U.S. Pat. Nos. 5,352,448, 5,296,231; 5,283,122; 5,277,913, 4,789,633] are particularly suitable for addition to bath powders or to bubble compositions, just prior to use. Upon contact with the low pH detergent or soap composition or a high pH composition, the contents of the liposome will be released. Other components, particularly $Ca^+$ or the presence of dissolved $O_2$ in the water will cause the components to glow as they are released. Temperature sensitive liposomes are also suitable for use in bath powders for release into the warm bath water.

c. Encapsulating Vehicles—Gelatin and Polymeric Vehicles

Macro or microcapsules made of gelatin or other such polymer that dissolve or release their contents in a beverage or food or on contact with air or light or changes in temperature may also be used to encapsulate components of the bioluminescence generating systems.

Such microcapsules or macrocapsules may also be incorporated into solid soaps, such that as the soap dissolves the incorporated capsules or pellets release their contents, which glow upon contact with the water in which the soap is placed.

The aequorin system is particularly suitable for this application. It can be encapsulated in suspension or solution or as a paste, or other suitable form, of buffer with sufficient chelating agent, such as EDTA, to prevent discharge of the bioluminescence. Upon exposure of the capsule [microcapsule or macrocapsule] to moisture that contains $Ca^{2+}$, such as in a food or beverage, a two chamber apparatus or single chamber apparatus, such as described herein, or even in a moist environment containing $Ca^{2+}$, the slowly released components will glow.

Thus, encapsulated bioluminescence generating components can be used in combination with foods, beverages, ice and ice cubes (and other geometries of ice), as bullets or pellets, such as "fairy dust" [pellets that dissolve upon exposure to light and thereby release the luciferase/luciferin, such as the Renilla system, which will light upon exposure to air], and other such items.

Other encapsulating containers or vehicles for use with the bioluminescence systems are those that dissolve sufficiently in water to release their contents, or that are readily opened when squeezed in the hand or from which the contents diffuse when mixed with a aqueous mixture. These containers can be made to exclude water, so that the bioluminescence generating system components may be desiccated and placed therein. Upon exposure to water, such as in an aqueous composition or in the atmosphere, the vehicle dissolves or otherwise releases the contents, and the components react and glow. Similarly, some portion including less than all of the bioluminescence generating reagents may be provided in pellet form or as a concentrated paste. For example, the component(s) may be mixed with gelatin or similar hardening agent, poured into a mold, if necessary and dried to produce a water soluble pellet.

The capsules, encapsulating containers or vehicles may be formed from gelatin or similar water soluble material. If the packaging is to be added to food or beverage, then it should be chosen to be non-toxic, non-reactive and flavorless. To be readily opened by hand, the packaging may be constructed of thin plastic or may be configured in two halves which form an airtight seal when joined but which are readily separated when release of the components is desired.

In one aspect, these capsular embodiments of the packaging apparatus is contemplated for use as an additive to beverages, creams, sauces, gelatins or other liquids or semi-solids. In another aspect, it is contemplated that the contents of the packaging apparatus is released into the air whereby it glows upon contact with the moisture of the atmosphere and/or with molecular oxygen.

d. Endosomes and Vacuoles

Vehicles may be produced using endosomes or vacuoles from recombinant host cells in which the luciferase is expressed using method known to those of skill in the art [see, e.g., U.S. Pat. Nos. 5,284,646, 5,342,607, 5,352,432, 5,484,589, 5,192,679, 5,206,161, and 5,360,726]. For example, aequorin that is produced by expression in a host, such as *E. coli*, can be isolated within vesicles, such as endosomes or vacuoles, after protein synthesis. Using routine methods the cells are lysed and the vesicles are released with their contents intact. The vesicles will serve as delivery vehicles. When used they will be charged with a luciferin, such as a coelenterazine, and dissolved oxygen, such as by diffusion, under pressure, or other appropriate means.

e. Micronized Particles

The bioluminescence generating system components that are suitable for lyophilization, such as the aequorin photoprotein, the Renilla system, and the Vargula systems, can be micronized to form fine powder and stored under desiccating conditions, such as with a desiccant. When used the fine powder can be combined with the selected article of manufacture, such as a personal item, a chamber in a gun or fountain, or used as fairy dust. Contact with dissolved oxygen or $Ca^{2+}$ in the air or in a mist that can be supplied or in added will cause the particles to release their contents and glow.

3. Apparatus and Substrates

The combinations herein are produced by combining a selected novelty item and combining it with a system and apparatus for producing bioluminescence. Selection of the system depends upon factors such as the desired color and duration of the bioluminescence desired as well as the particular item. Selection of the apparatus primarily depends upon the item with which it is combined.

Among the simplest embodiments herein, are those in which the apparatus contains a single chamber [vessel] or matrix material and, if needed, ejection means. Components, generally all but at least one necessary component, typically the activator as defined herein, of the bioluminescence reaction are introduced into the housing or vessel or onto the substrate as a mixture in liquid phase or as a powder or other paste or other convenient composition. Prior to use the final component(s) is added or the other components are contacted with the final component(s).

a. Matrix Materials

For preparation of combinations of articles of manufacture such as clothing, paper, items fabricated from a textile, plastic, glass, ceramic or other such material, such as a figurine, and for use in the cartridges, at least one component of the bioluminescence generating system is linked to the matrix substrate. When desired, a mixture or mixtures(s) containing the remaining component(s), typically a liquid mixture is applied, as by pouring or spraying onto the matrix substrate, to produce a glow. For example, the aequorin photoprotein, including coelenterazine and oxygen, is linked to the substrate. When desired a liquid containing $Ca^{2+}$, such as tap water or, preferably, a liquid mixture containing the $Ca^{2+}$ in an appropriate buffer, is contacted, such as by spraying, with the matrix with linked luciferase. Upon contacting the material glows.

In other embodiments, the luciferase, such as a Vargula luciferase, is linked to the substrate material, and contacted with a liquid mixture containing the luciferin in an appropriate buffer. Contacting can be effected by spraying or pouring or other suitable manner. The matrix material is incorporated into, onto or is formed into an article of manufacture, such as clothing or a ceramic, glass, plastic figurine, toy, balloon, flocking agent, such as a Christmas tree flocking agent, or other item. The resulting novelty item can be sold as a kit with a container of the mixture containing the non-linked components, such as in a canister, spray bottle or can, or other suitable format.

The kits may also include containers containing compositions of the linked components which can be provided in a form, such as sprayed on as a liquid and air dried, that can be applied to the substrate so that the item can be made to glow again. Thus, kits containing a substrate, such as clothing or a plastic, ceramic or glass item, and a first composition containing a luciferase or a luciferin or both and luciferin, and a second composition containing the remaining components. The item as provided in the kit can be charged with the first composition, such as having the composition applied and dried, or may require charging prior to the first use. Alternatively, the item may be sprayed with both compositions when desired to produce a glow.

It is understood that the precise components and optimal means for application or storage are a function of the selected bioluminescence system. The concentrations of the components, which can be determined empirically, are not critical, but must be sufficient to produce a visible glow when combined. Typical concentrations are as low as nanomoles/l, preferably on the order of mg/l or higher. The concentration on the substrate is that produced when a composition containing such typical concentration is applied to the material. Again, such ideal concentrations can be readily determined empirically by applying the first composition, letting it dry, spraying the second composition, and observing the result.

The matrix material substrates contemplated herein are generally insoluble materials used to immobilize ligands and other molecules, and are those that used in many chemical syntheses and separations. Such substrates, also called matrices, are used, for example, in affinity chromatography, in the immobilization of biologically active materials, and during chemical syntheses of biomolecules, including proteins, amino acids and other organic molecules and polymers. The preparation of and use of matrices is well known to those of skill in this art; there are many such materials and preparations thereof known. For example, naturally-occurring matrix materials, such as agarose and cellulose, may be isolated from their respective sources, and processed according to known protocols, and synthetic materials may be prepared in accord with known protocols.

The substrate matrices are typically insoluble materials that are solid, porous, deformable, or hard, and have any required structure and geometry, including, but not limited to: beads, pellets, disks, capillaries, hollow fibers, needles, solid fibers, random shapes, thin films and membranes. Thus, the item may be fabricated from the matrix material or combined with it, such by coating all or part of the surface or impregnating particles.

Typically, when the matrix is particulate, the particles are at least about 10–2000 $\mu$M, but may be smaller or larger, depending upon the selected application. Selection of the matrices will be governed, at least in part, by their physical and chemical properties, such as solubility, functional groups, mechanical stability, surface area swelling propensity, hydrophobic or hydrophilic properties and intended use.

If necessary the support matrix material can be treated to contain an appropriate reactive moiety or in some cases the may be obtained commercially already containing the reactive moiety, and may thereby serve as the matrix support upon which molecules are linked. Materials containing reactive surface moieties such as amino silane linkages, hydroxyl linkages or carboxysilane linkages may be produced by well established surface chemistry techniques involving silanization reactions, or the like. Examples of these materials are those having surface silicon oxide moieties, covalently linked to gamma-aminopropylsilane, and other organic moieties; N-[3-(triethyoxysilyl)propyl] phthelamic acid; and bis-(2-hydroxyethyl) aminopropyltriethoxysilane. Exemplary of readily available materials containing amino group reactive functionalities, include, but are not limited to, para-aminophenyltriethyoxysilane. Also derivatized polystyrenes and other such polymers are well known and readily available to those of skill in this art [e.g., the Tentagel® Resins are available with a multitude of functional groups, and are sold by Rapp Polymere, Tubingen, Germany; see, U.S. Pat. No. 4,908,405 and U.S. Pat. No. 5,292,814; see, also Butz et al. (1994) *Peptide Res.* 7:20–23; Kleine et al. (1994) *Immunobiol.* 190:53–66].

These matrix materials include any material that can act as a support matrix for attachment of the molecules of interest. Such materials are known to those of skill in this art, and include those that are used as a support matrix. These materials include, but are not limited to, inorganics, natural polymers, and synthetic polymers, including, but are not limited to: cellulose, cellulose derivatives, acrylic resins, glass, silica gels, polystyrene, gelatin, polyvinyl pyrrolidone, co-polymers of vinyl and acrylamide, polystyrene cross-linked with divinylbenzene or the like [see, Merrifield (1964) Biochemistry 3:1385–1390], polyacrylamides, latex gels, polystyrene, dextran, polyacrylamides, rubber, silicon, plastics, nitrocellulose, celluloses, natural sponges. Of particular interest herein, are highly porous glasses [see, e.g., U.S. Pat. No. 4,244,721] and others prepared by mixing a borosilicate, alcohol and water.

Synthetic matrices include, but are not limited to: acrylamides, dextran-derivatives and dextran co-polymers, agarose-polyacrylamide blends, other polymers and co-polymers with various functional groups, methacrylate derivatives and co-polymers, polystyrene and polystyrene copolymers [see, e.g., Merrifield (1964) Biochemistry 3:1385–1390; Berg et al. (1990) in *Innovation Perspect. Solid Phase Synth. Collect. Pap.*, Int. Symp., 1st, Epton, Roger (Ed), pp. 453–459; Berg et al. (1989) in *Pept., Proc. Eur. Pept. Symp.*, 20th, Jung, G. et al. (Eds), pp. 196–198; Berg et al. (1989) *J. Am. Chem. Soc.* 111 :8024–8026; Kent et al. (1979) *Isr. J. Chem.* 17:243–247; Mitchell et al. (1978) *J. Org. Chem.* 43:2845–2852; Mitchell et al. (1976) *Tetrahedron Lett.* 42:3795–3798; U.S. Pat. No. 4,507,230; U.S. Pat. No. 4,006,117; and U.S. Pat. No. 5,389,449]. Methods for preparation of such matrices are well-known to those of skill in this art.

Synthetic matrices include those made from polymers and co-polymers such as polyvinylalcohols, acrylates and acrylic acids such as polyethylene-co-acrylic acid, polyethylene-co-methacrylic acid, polyethylene-co-ethylacrylate, polyethylene-co-methyl acrylate, polypropylene-co-acrylic acid, polypropylene-co-methyl-acrylic acid, polypropylene-co-ethylacrylate, polypropylene-co-methyl acrylate, polyethylene-co-vinyl acetate, polypropylene-co-vinyl acetate, and those containing acid anhydride groups such as polyethylene-co-maleic anhydride, polypropylene-co-maleic anhydride and the like. Liposomes have also been used as solid supports for affinity purifications [Powers et al. (1989) *Biotechnol. Bioeng.* 33:173].

For example, U.S. Pat. No. 5,403,750, describes the preparation of polyurethane-based polymers. U.S. Pat. No. 4,241,537 describes a plant growth medium containing a hydrophilic polyurethane gel composition prepared from chain-extended polyols; random copolymerization is preferred with up to 50% propylene oxide units so that the prepolymer will be a liquid at room temperature. U.S. Pat. No. 3,939,123 describes lightly crosslinked polyurethane polymers of isocyanate terminated prepolymers containing poly(ethyleneoxy) glycols with up to 35% of a poly(propyleneoxy) glycol or a poly(butyleneoxy) glycol. In producing these polymers, an organic polyamine is used as a crosslinking agent. Other matrices and preparation thereof are described in U.S. Pat. Nos. 4,177,038, 4,175,183, 4,439, 585, 4,485,227, 4,569,981, 5,092,992, 5,334,640, 5,328,603.

U.S. Pat. No. 4,162,355 describes a polymer suitable for use in affinity chromatography, which is a polymer of an aminimide and a vinyl compound having at least one pendant halo-methyl group. An amine ligand, which affords sites for binding in affinity chromatography is coupled to the polymer by reaction with a portion of the pendant halo-methyl groups and the remainder of the pendant halo-methyl groups are reacted with an amine containing a pendant hydrophilic group. A method of coating a substrate with this polymer is also described. An exemplary aminimide is 1,1-dimethyl-1-(2-hydroxyoctyl)amine methacrylimide and vinyl compound is a chloromethyl styrene.

U.S. Pat. No. 4,171,412 describes specific matrices based on hydrophilic polymeric gels, preferably of a macroporous character, which carry covalently bonded D-amino acids or peptides that contain D-amino acid units. The basic support is prepared by copolymerization of hydroxyalkyl esters or hydroxyalkylamides of acrylic and methacrylic acid with crosslinking acrylate or methacrylate comonomers are modified by the reaction with diamines, aminoacids or dicarboxylic acids and the resulting carboxyterminal or aminoterminal groups are condensed with D-analogs of aminoacids or peptides. The peptide containing D-aminoacids also can be synthesized stepwise on the surface of the carrier.

U.S. Pat. No. 4,178,439 describes a cationic ion exchanger and a method for preparation thereof. U.S. Pat. No. 4,180,524 describes chemical syntheses on a silica support.

Immobilized Artificial Membranes [IAMs; see, e.g., U.S. Pat. Nos. 4,931,498 and 4,927,879] may also be used. IAMs mimic cell membrane environments and may be used to bind molecules that preferentially associate with cell membranes [see, e.g., Pidgeon et al. (1990) *Enzyme Microb. Technol.* 12:149].

These materials are also used for preparing articles of manufacture, such as toys, balloons, figurines, sponges, knick-knacks, key chains, clothing, translucent or transparent soaps, preferably mild soaps, and other items, and thus are amenable to linkage of molecules, either the luciferase, luciferin, mixtures thereof.

For example, matrix particles may be impregnated into items that will then be contacted with an activator. For example, matrix particles with linked luciferin, preferably a luciferin/luciferase complex, such as the aequorin photoprotein is incorporated into a transparent or translucent soaps [see, e.g., U.S. Pat. Nos. 4,081,394, 5,183,429, and 5,141, 664, and United Kingdom Patent No. GB 2,235,931A], preferably a mild soap. Upon contacting the soap with water matrix particles near the surface will glow.

Kits containing the item including the matrix material with or without the coating of the bioluminescence generating components, and compositions containing the remaining components are provided.

b. Immobilization and Activation

Numerous methods have been developed for the immobilization of proteins and other biomolecules onto solid or liquid supports [see, e.g., Mosbach (1976) *Methods in Enzymology* 44; Weetall (1975) *Immobilized Enzymes, Antigens, Antibodies, and Peptides;* and Kennedy et al. (1983) *Solid Phase Biochemistry, Analytical and Synthetic Aspects,* Scouten, ed., pp. 253–391; see, generally, *Affinity Techniques. Enzyme Purification: Part B. Methods in Enzymology,* Vol. 34, ed. W. B. Jakoby, M. Wilchek, Acad. Press, N.Y. (1974); *Immobilized Biochemicals and Affinity Chromatography, Advances in Experimental Medicine and Biology,* vol. 42, ed. R. Dunlap, Plenum Press, N.Y. (1974)].

Among the most commonly used methods are absorption and adsorption or covalent binding to the support, either directly or via a linker, such as the numerous disulfide linkages, thioether bonds, hindered disulfide bonds, and covalent bonds between free reactive groups, such as amine and thiol groups, known to those of skill in art [see, e.g., the PIERCE CATALOG, ImmunoTechnology Catalog & Handbook, 1992–1993, which describes the preparation of and use of such reagents and provides a commercial source for such reagents; and Wong (1993) *Chemistry of Protein Conjugation and Cross Linking,* CRC Press; see, also DeWitt et al. (1993) *Proc. Natl. Acad. Sci. U.S.A.* 90:6909; Zuckermann et al. (1992) *J. Am. Chem. Soc.* 114:10646; Chem et al. (1994) *J. Am. Chem. Soc.* 116:2661; Bunnin et al. (1994) *Proc. Natl. Acad. Sci. U.S.A.* 91:4708; Sucholeiki (1994) *Tetrahedron Lttrs.* 35:7307; and Su-Sun Wang (1976) *J. Org. Chem.* 41:3258; Padwa et al. (1971) *J. Org. Chem.* 41:3550 and Vedejs et al. (1984) *J. Org. Chem.* 49:575, which describe photosensitive linkers].

To effect immobilization, a composition containing the protein or other biomolecule is contacted with a support material such as alumina, carbon, an ion-exchange resin, cellulose, glass or a ceramic. Fluorocarbon polymers have been used as supports to which biomolecules have been attached by adsorption [see, U.S. Pat. No. 3,843,443; Published International PCT Application WO/86 03840].

A large variety of methods are known for attaching biological molecules, including proteins and nucleic acids, molecules to solid supports [see. e.g., U.S. Pat. No. 5451683]. For example, U.S. Pat. No. 4,681,870 describes a method for introducing free amino or carboxyl groups onto a silica matrix. These groups may subsequently be covalently linked to other groups, such as a protein or other anti-ligand, in the presence of a carbodiimide. Alternatively, a silica matrix may be activated by treatment with a cyanogen halide under alkaline conditions. The anti-ligand is covalently attached to the surface upon addition to the activated surface. Another method involves modification of a polymer surface through the successive application of multiple layers of biotin, avidin and extenders [see, e.g., U.S. Pat. No. 4,282,287]; other methods involve photoactivation in which a polypeptide chain is attached to a solid substrate by incorporating a light-sensitive unnatural amino acid group into the polypeptide chain and exposing the product to low-energy ultraviolet light [see, e.g., U.S. Pat. No. 4,762,881]. Oligonucleotides have also been attached using a photochemically active reagents, such as a psoralen compound, and a coupling agent, which attaches the photoreagent to the substrate [see, e.g., U.S. Pat. No. 4,542,102 and U.S. Pat. No. 4,562,157]. Photoactivation of the photoreagent binds a nucleic acid molecule to the substrate to give a surface-bound probe.

Covalent binding of the protein or other biomolecule or organic molecule or biological particle to chemically activated solid matrix supports such as glass, synthetic polymers, and cross-linked polysaccharides is a more frequently used immobilization technique. The molecule or biological particle may be directly linked to the matrix support or linked via linker, such as a metal [see, e.g., U.S. Pat. No. 4,179,402; and Smith et al. (1992) *Methods: A Companion to Methods in Enz.* 4:73–78]. An example of this method is the cyanogen bromide activation of polysaccharide supports, such as agarose. The use of perfluorocarbon polymer-based supports for enzyme immobilization and affinity chromatography is described in U.S. Pat. No. 4,885, 250]. In this method the biomolecule is first modified by reaction with a perfluoroalkylating agent such as perfluorooctylpropylisocyanate described in U.S. Pat. No. 4,954, 444. Then, the modified protein is adsorbed onto the fluorocarbon support to effect immobilization.

The activation and use of matrices are well known and may be effected by any such known methods [see, eg., Hermanson et al. (1992) *Immobilized Affinity Ligand Techniques,* Academic Press, Inc., San Diego]. For example, the coupling of the amino acids may be accomplished by techniques familiar to those in the art and provided, for example, in Stewart and Young, 1984, *Solid Phase Synthesis,* Second Edition, Pierce Chemical Co., Rockford.

Other suitable methods for linking molecules to solid supports are well known to those of skill in this art [see, e.g., U.S. Pat. No. 5,416,193]. These include linkers that are suitable for chemically linking molecules, such as proteins, to supports and include, but are not limited to, disulfide bonds, thioether bonds, hindered disulfide bonds, and covalent bonds between free reactive groups, such as amine and thiol groups. These bonds can be produced using heterobifunctional reagents to produce reactive thiol groups on one or both of the moieties and then reacting the thiol groups on one moiety with reactive thiol groups or amine groups to which reactive maleimido groups or thiol groups can be attached on the other. Other linkers include, acid cleavable linkers, such as bismaleimideothoxy propane, acid labile-transferrin conjugates and adipic acid diihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (see, Batra et al. (1993) *Molecular Immunol.* 30:379–386). Presently preferred linkages are direct linkages effected by adsorbing the molecule to the surface of the matrix. Other linkages are photocleavable linkages that can be activated by exposure to light [see, e.g., Goldmacher et al. (1992) *Bioconj. Chem.* 3:104–107, which linkers are herein incorporated by reference]. The photocleavable linker is selected such that the cleaving wavelength that does not damage linked moieties. Photocleavable linkers are linkers that are cleaved upon exposure to light [see, e.g., Hazum et al. (1981) in *Pept., Proc. Eur. Pept. Symp.,* 16th, Brunfeldt, K (Ed), pp. 105–110, which describes the use of a nitrobenzyl group as a photocleavable protective group for cysteine; Yen et al. (1989) *Makromol. Chem* 190:69–82, which describes water soluble photocleavable copolymers, including hydroxypropylmethacrylamide copolymer, glycine copolymer, fluorescein copolymer and methylrhodamine copolymer; Goldmacher et al. (1992) *Bioconj. Chem.* 3:104–107, which describes a cross-linker and reagent that undergoes photolytic degradation upon exposure to near UV light (350 nm); and Senter et al. (1985) *Photochem. Photobiol* 42:231–237, which describes nitrobenzyloxycarbonyl chloride cross linking reagents that produce photocleavable linkages]. The selected linker will depend upon the particular application and, if needed, may be empirically selected.

Aequorin that is designed for conjugation and conjugates containing such aequorin have been produced [see, e.g., International PCT application No. WO 94/18342; see, also Smith et al. (1995) in *American Biotechnology Laboratory*]. Vargula luciferase has also been linked to other molecules [see, e.g., Japanese application No. JP 5064583, Mar. 19, 1993]. Such methods may be adapted for use herein to produce aequorin coupled to protein or other such molecules, which are linked to the selected matrix. Finally, as an alternative, a component of the bioluminescence generating system may be modified for linkage, such as by addition of amino acid residues that are particularly suitable for linkage to the selected substrate. This can be readily effected by modifying the DNA and expressing such modified DNA to produce luciferase with additional residues at the N- or C-terminus.

4. Apparatus Containing a Single Chamber, Housing or a Vessel

Examples of vessels include beverage containers, plates or other dishes, vases, jars, balloons, bottles and other containers.

Single chamber housings or vessels will include single chamber water guns, inks, paints and other such items, in which one or more components of the bioluminescence system up to all of the components except for one of the components required for bioluminescence is included in the vessel as a mixture, powder or suspension of particles. The remaining component(s) is(are) introduced just prior to use. Thus, for example, for a squirt gun or a balloon or other such item, the items can be packaged with a powder in the chamber or inside the item, or a powder or other composition can be added, and then water is added. Alternatively, the luciferase, such as Renilla, Vargula, and firefly luciferase, can be linked to the surface of the item and water added. Depending upon the bioluminescence generating system selected the water can be tap water or water that contains the additional component, such as dissolved oxygen, or $Ca^{2+}$ or ATP, or other suitable composition, and/or appropriate luciferin/bioluminescence substrate. Similarly, the luciferase/ luciferase can be linked to the surface of the item in association with the appropriate luciferin/ bioluminescence substrate, such that addition of activator alone generates luminescence.

For inks or paints the components are suspended in the ink or paint, and then the final component(s) is(are) added. Alternatively, pellets containing components of the bioluminescence generating system, such as the Renilla or Aequorin system can be added to an ink or paint or other such liquid item, and as the pellet dissolves or the contents diffuse out, the item will glow.

Kits containing the item and the bioluminescence generating systems are also provided herein. The kits typically contain a beverage container, balloon or bottle and, may also contain, the buffer compositions and other ingredients required for the bioluminescence reaction, as well as instructions for use. The kits may also include the cartridges for recharging or reloading the item.

5. Dual and Multiple Chamber Fluid Dispensing Apparatus

An example of a dispensing apparatus contemplated for use herein is a dual chamber fluid dispensing apparatus. In general, this apparatus has two chambers thereby maintaining at least one of the bioluminescence generating system components separate from the remaining components until illumination is desired. This apparatus may include a mixing chamber to permit mixing of the components prior to dispensing from the apparatus. Further, the apparatus may be used with fluid or semi-fluid bioluminescence systems; for example, water based compositions or cream/lotion systems.

a. Mechanical Pump Dispensing Apparatus

Another embodiment of a dual chamber fluid dispensing apparatus employs a mechanical pump mechanism in its operation. In this embodiment, the dispensing apparatus maintains at least one of the components of the bioluminescence reaction, such as the substrate, luciferase or activator, in separate chambers. A pump mechanism operates to withdraw the contents from each chamber and into a mixing chamber. Within the mixing chamber and upon ejection, the mixed composition is activated, for example by the oxygen in the air or by reaction of the components that were in one chamber, and glows. The pump mechanism may be manually operated, for example by pulling the trigger of a toy squirt gun, or it may be mechanically operated, for example by a motor which operates the pumping mechanism.

b. Gas-Charged Dispensing Apparatus

Another example of a dual chamber fluid dispensing apparatus is one that uses $CO_2$ or, preferably a mixture gases containing $O_2$, or other gas, to propel the components of the bioluminescence system, such as the bioluminescence substrate and luciferase into a mixing chamber where they combine before being ejected through a dispensing nozzle. In such a dispensing apparatus, upon mixing of the contents in the mixing chamber the contents will glow.

These apparatus may be configured as, for example, a toy gun, toy cannon or other toy weapon, a can for shaving cream or other glowing foam, a decorative fountain or volcano or almost any fluid squirting or spouting device. A volcano shaped dispensing apparatus may be used, for example, as a substitute for conventional, similarly shaped fireworks displays.

Almost any bioluminescence generating system may be selected for use with the dual chamber fluid dispensing apparatus. If air is the bioluminescence activator, then the contents glow after mixing and upon ejection from the dispensing apparatus. Alternatively, the bioluminescent activator may be contained in one of the two chambers along with either the luciferase or bioluminescence substrate, or it may be located in a third chamber that is also connected to the mixing chamber. Thus, as with all the combinations described herein, the critical aspect of these dispensing apparatus is that at least one of the bioluminescence generating system components be maintained separate from the other components until reaction is desired.

c. Compressible Dispensing apparatus

Another embodiment of a dual chamber fluid dispensing apparatus contemplated for use herein takes the form of a compressible bottle or tube. The bottle has two compartments within it that keep at least two of the bioluminescence generating system components separated. The cap of the bottle can serve as a mixing chamber or a mixing chamber may be positioned between the two chambers and the cap. The bioluminescence generating system components are forced by compression from the bottle into the mixing chamber. They are then dispensed from the mixing chamber. For example, the mixed contents may be removed from the bottle by attaching a plunger/syringe apparatus to the dispensing end and withdrawing the contents therethrough.

Such compressible bottle or tube is particularly useful for dispensing bioluminescent body creams, gels or lotions, finger paints, dentifrices, shampoos, hair gels, cosmetics and other viscous fluids and semi-solids. The bottle or tube is preferably constructed of plastic, plastic/metal laminate or similar collapsible composite to avoid formation of a vacuum within the container as its contents are expelled. See, for example, U.S. Pat. No. 4,687,663, which describes a dual chambered tube for use with dentifrices and which, as all cited patents and publications herein, is incorporated herein in its entirety. This tube may be adapted for use in combination with the bioluminescence generating systems provided herein. Other tubes and vessels that have dual chambers, such as those used to keep components of the final product separate until use, may be used herein [see, e.q., U.S. Pat. Nos. 5,405,056, 4,676,406, 4,438,869, 5,059,417, 4,528,180, 4,849,213, 4,895,721, 5,085,853, see, esp. 5,038,963]

6. Other fluid dispensing and packaging apparatus particularly designed for single use Additional embodiments of the dispensing and packaging apparatus contemplated for use herein include fluid packaging apparatus, designed for use with bioluminescent fluids. These apparatus maintain at least one of the bioluminescence generating system components separate from the remaining components until illumination is desired. Unlike the dual chamber fluid dispensing apparatus, however, these apparatus result in illumination of the entire contents of the package and therefore are typically intended for a single use applications. They can, however, be recharged by adding additional substrate, luciferase or other exhausted component.

a. Bottle-type single chamber container/bladder apparatus

One example of a fluid packaging apparatus, contemplated for use herein, is a bottle shaped device having a bladder within it that contains at least one of the bioluminescence generating system components. A piercing pin or other means for rupturing the bladder is also located within the bottle. When the bladder is ruptured, within the bottle, its contents mix with the contents of the bottle and the resulting mixture becomes illuminated or glows upon contact with an activator, such as air.

Because the bioluminescence generating system components are mixed within the entire bottle, those contents must be used shortly after mixing. Thus, this type of packaging is particularly suitable for use with bioluminescence systems that are consumed in a single use or activity such as bubble-blowing.

b. Dual chambered bottle type container/bladder apparatus for use with foods and beverages Another example of a fluid packaging apparatus provided herein is a single use, dual chambered bottle. This apparatus is configured with a membrane between the two chambers. One chamber is designed to readily collapse against the other chamber thereby rupturing the membrane which divides the chambers. The contents of the two chambers then mix, resulting in illumination of the fluids. Alternatively, instead of a membrane separation means, a one-way valve may be situated between the two chambers. Such a single use, dual chamber apparatus is particularly suitable for use with bubble-making compositions, beverages, single use amounts of shampoos, soaps, creams or lotions, or similar substances.

c. Can type container/bladder apparatus for use with foods and beverages

Another example of a fluid packaging apparatus, which is amenable to use with bioluminescent food or beverage, is a container/bladder combination. In one embodiment, the container is configured like a pop-top can, such as a soda can. A bladder, containing at least one of the bioluminescence generating system components, is positioned under the top of the can. Within the can is a beverage that contains the remaining bioluminescence generating system components. Upon opening the can, the bladder is punctured and its contents mixed with the rest of the contents of the can; thereby illuminating the beverage. Preferably, the container is clear, so that the illumination will be almost immediately visible. Other pop top cans that can be modified for use herein are known [see, e.g., U.S. Pat. No. 5,397,014].

Alternative configurations of the container/bladder apparatus are likewise contemplated. For example, the container may be in any shape and configured with a removable cap to which the bladder is attached. To cause the beverage to glow, the bladder is punctured or otherwise compromised and its contents added to the container; thereby causing illumination of the food or beverage. The contents of the container need not be a food or beverage, any fluid or semi-solid may be used and is herein contemplated.

d. Spray containers that produce a glowing spray

Spray containers or cans that are adapted to produce a glowing spray are provided herein. These containers are also intended for use in any application in which two components, particularly solutions or liquid components, are intended to be mixed just prior to use. These containers include a housing portion for the first component and a second portion designed to inject or introduce the second component.

Figure 20:
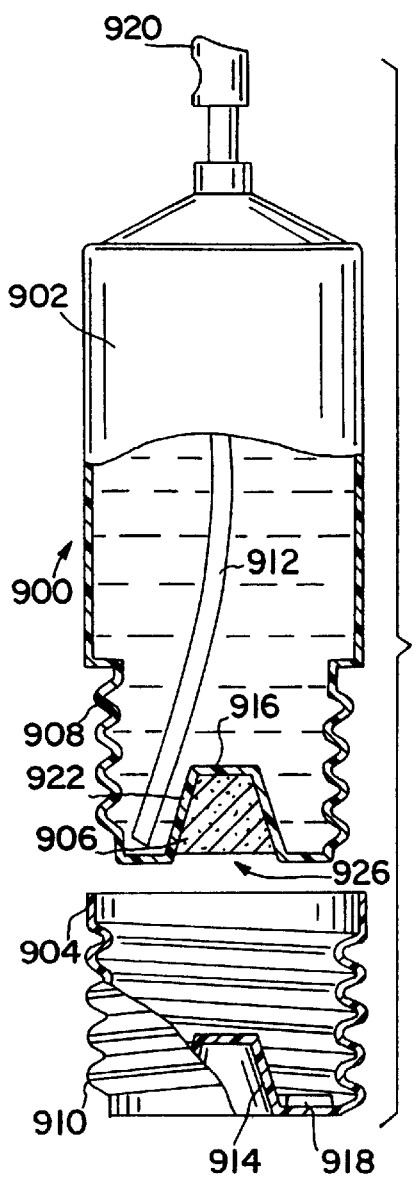
FIG. 20 is a side elevation view, with portions cut away, of a spray container or can in which the bottom portion of the apparatus is not engaged.
Figure 21:
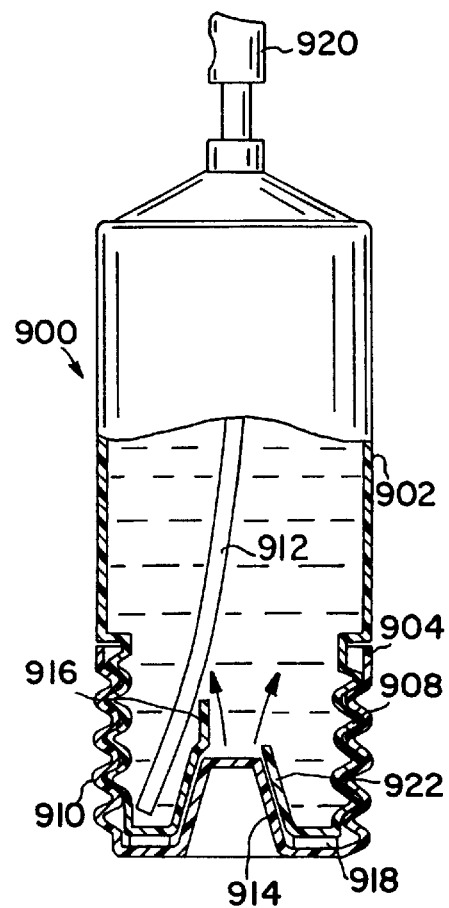
FIG. 21 is a side elevation view, with portions cut away, of the spray container in which the bottom portion of the container is engaged.
Figure 22:
FIG. 22 is a side elevation view of an exemplary pellet that contains bioluminescence-generating reagents and that is adapted for use with the spray container.

A preferred embodiment of these containers, which is illustrated in FIGS. 20–22 [see, also EXAMPLE 10], includes two portions, a top housing portion and a bottom plunger portion. For use in generating bioluminescence, the top housing portion includes all, except one or more, of the components of a bioluminescence generating system. The remaining components of the bioluminescence generating system are contained in a pellet or are encapsulated, as described above.

The top housing portion is adapted at its bottom end with an indentation within which the pellet fits. At least one wall of the indentation includes a rupturable membrane or material. The top housing portion is further adapted to attach securely to and within the bottom plunger portion. A plunger is situated within the bottom plunger portion such that the plunger rests in the indentation of the top housing portion when the bottom plunger portion is tightly secured thereto. In operation, the pellet or encapsulated vehicle is placed within the indentation of the top housing portion and the bottom plunger portion secured tightly thereto. The plunger within the bottom plunger portion presses against the pellet forcing it through the rupturable membrane or material, thereby permitting the pellet to dissolve in and mix with the contents of the top housing portion. Alternatively the pellet will include a sharpened portion that will puncture the rupturable wall of the housing. An angular seal may be used, situated within the bottom plunger portion, to set against the bottom of the top housing portion forming a seal to prevent leakage of the mixed contents of the spray can apparatus. The top housing portion additionally contains a conduit or other suitable means for ejecting the contents.

The top housing portion of the spray container may be adapted to receive the bottom plunger portion by threading the two spray can portions so that they may be screwed together. [See, e.g., FIG. 21, illustrating the spray container apparatus with the bottom plunger portion fully screwed into place]. Alternatively, the two portions may be adapted to snap together, such as by insertion of a tongue from one portion into a groove of the other portion.

As stated, the indentation or pocket located in the bottom end of the top housing portion includes at least one wall formed by a rupturable membrane. Preferably that wall is the top wall and is readily ruptured by pressure, for example, from the pellet or plunger or plunger forcing the pellet, against it. The pellet is fabricated from material that will release the contents into aqueous medium. The pellet may also include a sharp tip designed to puncture the spray container.

The spray container is fabricated from suitable materials, such as plastic, aluminum, metal alloys, tin, and other materials from which spray cans and containers, such as hair spray cans and other containers designed for delivery of aerosols and sprays, are fabricated. The size of the spray can apparatus may vary depending upon the intended use and demands of the market place, but will typically have a usable volume of from about 100 mls to about a liter.

The bottom plunger portion is typically fabricated from a metal, such as aluminum, and the plunger is shaped and situated such that it fits into the pocket of the top housing portion when the bottom plunger portion is screwed tightly in place. It can also be made from compressible plastic or other such material and designed to compress and deliver the inserted pellet, which is designed to fit into the indentation, slot or pocket and be retained by virtue of the tight fit.

7. Cap Apparatus for use a single chamber vessel

Another example of a packaging apparatus contemplated herein is a cap apparatus for use with a vessel. In this embodiment, one or more of the bioluminescence generating system components, up to all but one component, is [are] within the cap of the vessel and the remaining components are contained in the vessel. Upon operation of the cap apparatus, the bioluminescence generating system components are added to the composition in the vessel and the composition glows. Preferably the vessel is translucent to the bioluminescence; however, the glowing composition may be dispensed from the vessel.

Generally, the cap is configured with a pocket within it which opens to the bottom of the cap. For example, the bottom of the cap can be U-shaped, curving into the cap and thereby forming the pocket. The cap apparatus contains a capsule or similar package, containing one or more, up to all but one, of the bioluminescence generating system components, within the pocket in the cap. Means for deploying the bioluminescence generating system components into the vessel are attached to the cap. Such deployment means can be, for example, a plunger assembly. The cap apparatus is operated by depressing the plunger, thereby forcing the packaged components into the composition within the vessel or breaking the packaging, releasing its contents into the composition within the vessel. The package should be dissolvable in the composition or amenable to diffusion of the components contained therein or readily rupturable upon contact with the plunger assembly.

Alternatively, the packaging within the cap apparatus can be a membrane or series of membranes separating the bioluminescence generating system components from the composition within the vessel or from the composition within the vessel and from each other. In this alternative, the plunger can rupture the membrane(s) thereby permitting the bioluminescence generating system components contained therein to be released into the composition contained in the vessel. Again, upon mixture of the components with the composition, illumination ensues.

The bioluminescence generating system components contained within the cap apparatus may be in a composition, such as a solution, a powder or a suspension of particles or other form amenable to packaging within the cap apparatus that can be mixed with the composition contained within the vessel. The cap apparatus also may be adapted with a screen or filter attached to the bottom of the cap to prevent membrane fragments from entering the vessel.

The cap apparatus, as all the apparatus described herein that are in contact with a bioluminescence generating system component, should be non-reactive with the components and is preferably non-toxic, particularly if used with a composition intended for human consumption. The cap can be constructed of cork, for example, and situated in a wine or champagne bottle. Alternatively, the cap can be a screw-top type cap, having a plunger integral thereto, such that tightening of the screw-cap onto the top of the vessel forces the plunger against the packaged bioluminescence generating system components either rupturing the packaging or pushing it into the vessel.

E. Combinations of articles of manufacture and bioluminescence

Combinations of articles of manufacture and bioluminescence are provided herein. By virtue of the bioluminescence the combinations are novelty items because the bioluminescence provides entertainment, amusement or recreation. Any such combination of an article of manufacture with bioluminescence that produces a novelty item [i.e., provides entertainment, amusement, or recreation] is intended herein. The combination is formed by contacting the article of manufacture or materials in the manufacture with a bioluminescence generating system or an apparatus therefore. The components of the bioluminescence generating system are manufactured as part of the item, coated thereon, impregnated therein, or added after manufacture. Alternatively, the article of manufacture is combined with an apparatus that contains or to which components of the bioluminescence generating system are added, and that produces the bioluminescence.

The bioluminescence generating systems provided herein are contemplated for use with various substances to glow the substance. For example, as discussed below, the bioluminescence generating system components may be used to produce glowing aqueous mixtures housed in transparent portions of articles of manufacture, thereby illuminating that portion of the article of manufacture. Additionally, the bioluminescence generating system components may be used to produce glowing food or beverage products, textiles, creams, lotions, gels, soaps, bubbles, papers, powders or water. Following are brief examples of combinations of bioluminescence systems with articles of manufacture and the resulting novelty items contemplated herein.

1. Personal care products, including bath powders, bubble baths, products for use on the nails, hair, skin, lips and elsewhere Personal care products can be in the form of powders, pressed powders, sprays, foams, aerosols, lotions, gels, ointments and other suitable formulations. The common element will be the combination of such items with bioluminescence generating reagents or fluorescent proteins, so that before use or upon application to the body or when used the product will glow. These items include, body powders, lotions, gels, aqueous compositions and solutions, nail polishes, make-up, body paints, shaving cream and dentifrices. As described herein, the items are combined with one or more components of a bioluminescence generating system, and, when a glow is desired, the remaining components are added or combined with the other components.

a. Bath powders

Numerous bath powders exemplified herein, are suitable for use in combination with the bioluminescence generating systems herein. Such bath powders are preferably non-detergent with a pH close to neutral. The selected bioluminescence generating system must be selected to be active at the resulting pH. In addition, capsular delivery vehicles, such as liposomes or time release delivery vehicles, preferably microcapsules, that contain a luciferase and luciferin, such as the Renilla, Vargula, or Aequorin system, and that are pH, temperature sensitive, or that dissolve in water or that are otherwise released are preferred for use herein. In certain embodiments, there will be two types of capsules, one type containing up to all but one of the components required for the bioluminescence reaction, and the other containing the remaining components [except, if desired, for those components that will be present in the bath water, such as $Ca^{2+}$]. Such capsules may be components of the bath powder or may be added to a bath to give it a glow. Upon contact with the warm water or with water of a particular pH the contents of the capsule or pellet will be released, preferably over time, and will glow.

In other embodiments, there will be one type of capsule that contains the luciferase and other components. The luciferin may be included in the bath powder or added separately. Other ways in which the components may be combined will, in light of the disclosure herein, be apparent to those of skill in the art. The bath powders and bioluminescence generating reactions will be provided as a combination or in a kit.

Suitable bath powders and bubble baths and other bubble compositions for use in these combinations are well known to those of skill in the art [see, e.g., U.S. Pat. Nos.: 5,478,501 4,565,647; 5,478,490; 5,412,118; 5,401,773; and many other examples]. These may be modified by adding the bioluminescence generating system components.

b. Glowing dust or powder

Another embodiment of the combination described herein is as a glowing dust or powder substance, or a vapor, such as for use in the theatrical productions. In this embodiment, lyophilized or desiccated forms, micronized powdered forms, or, a suitable composition, of up to all but one of the bioluminescence generating system components are encapsulated in readily rupturable or time release or temperature or pH or light sensitive microspheres or capsules, as described above. Preferable encapsulating agents are light or temperature sensitive so that upon exposure to the environment, the contents are released from the capsules. Moisture or oxygen in the air or a spray of water on the skin with dissolved oxygen in the vicinity of the "dust" will produce a glow.

The dust can be added to another powder, such as body powder, provided it is stored in an airtight container. Once the powder contacts the moisture in the air and on the wearer's skin, it glows.

Alternatively, micronized particles of lyophilized powders are packaged such in manner so that the powder remains dry. Upon exposure to moist air or to air with water droplets [such as a fog], the micronized powders will glow.

c. Lotions, gels and other topical application formulations

For application to the skin, the macro or microparticles or the luciferase, luciferin or mixture thereof, may be added to cosmetic compositions. The compositions may be provided in the form of gels, creams, lotions, solids, and other compositions, such as solutions and suspensions, aerosols or solid base or vehicle known in the art to be non-toxic and dermatologically acceptable to which sufficient number of such particles are added under conditions in which the contents are released into the gels, creams, lotions, solids, solutions or suspensions, or aerosols, which contain either molecular oxygen and/or $Ca^{2+}$ to react with the contents of particles. Upon application to the skin the gels, creams, lotions, solids, solutions or suspensions, or aerosols glow.

(1) Lotions

The lotions contain an effective concentration of less than all reagents for one or more bioluminescence generating systems. Preferably, the reagents are encapsulated in a vehicle that releases its contents upon exposure to light or temperature, such that as the contents of the vehicle are released they react with oxygen or $Ca^{2+}$ in the lotion and/or on the skin. Prior to use the skin can be sprayed with a mist of water, buffer or other composition containing the requisite ions. The effective concentration is that sufficient to produce a visible glow when contacting the skin. Any emollients, as long as they do not inactivate the bioluminescent reaction, known to those of skill in the art as suitable for application to human skin may be used. These include, but are not limited to, the following:

(a) Hydrocarbon oils and waxes, including mineral oil, petrolatum, paraffin, ceresin, ozokerite, microcrystalline wax, polyethylene, and perhydrosqualene.

(b) Silicone oils, including dimethylpolysiloxanes, methylphenylpolysiloxanes, water-soluble and alcohol-soluble silicone-glycol copolymers.

(c) Triglyceride fats and oils, including those derived from vegetable, animal and marine sources. Examples include. but are not limited to, castor oil, safflower oil, cotton seed oil, corn oil, olive oil, cod liver oil, almond oil, avocado oil, palm oil, sesame oil, and soybean oil.

(d) Acetoglyceride esters, such as acetylated monoglycerides.

(e) Ethoxylated glycerides, such as ethoxylated glyceryl monstearate.

(f) Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, isopropyl myristate, decyl oleate, isodecyl oleate, hexadecyl stearate, decyl stearate, isopropyl isostearate, diisopropyl adipate, diisohexyl adipate, dihexyidecyl adipate, diisopropyl sebacate, lauryl lactate, myristyl lactate, and cetyl lactate.

(g) Alkenyl esters of fatty acids having 10 to 20 carbon atoms. Examples thereof include, but are not limited to, oleyl myristate, oleyl stearate, and oleyl oleate.

(h) Fatty acids having 9 to 22 carbon atoms. Suitable examples include, but are not limited to, pelargonic, lauric, myristic, palmitic, stearic, isostearic, hydroxystearic, oleic, linoleic, ricinoleic, arachidonic, behenic, and erucic acids.

(i) Fatty alcohols having 10 to 22 carbon atoms, such as, but not limited to, lauryl, myristyl, cetyl, hexadecyl, stearyl, isostearyl, hydroxystearyl, oleyl, ricinoleyl, behenyl, erucyl, and 2-octyl dodecyl alcohols.

(j) Fatty alcohol ethers, including, but not limited to ethoxylated fatty alcohols of 10 to 20 carbon atoms, such as, but are not limited to, the lauryl, cetyl, stearyl, isostearyl, oleyl, and cholesterol alcohols having attached thereto from 1 to 50 ethylene oxide groups or 1 to 50 propylene oxide groups or mixtures thereof.

(k) Ether-esters, such as fatty acid esters of ethoxylated fatty alcohols.

(l) Lanolin and derivatives, including, but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases.

(m) Polyhydric alcohols and polyether derivatives, including, but not limited to, propylene glycol, dipropylene glycol, polypropylene glycol [M.W. 2000–4000], polyoxyethylene polyoxy-propylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol [M.W. 200–6000], methoxy polyethylene glycols 350, 550, 750, 2000, 5000, poly(ethylene oxide) homopolymers [M.W. 100,000–5,000,000], polyalkylene glycols and derivatives, hexylene glycol (2-methyl-2,4-pentanediol), 1,3-butylene glycol, 1,2,6,-hexanetriol, ethohexadiol USP (2-ethyl-1,3-hexanediol), $C_{15}-C_{18}$ vicinal glycol and polyoxypropylene derivatives of trimethylolpropane.

(n) Polyhydric alcohol esters, including, but not limited to, ethylene glycol mono- and di-fatty acid esters, diethylene glycol mono- and di-fatty acid esters, polyethylene glycol [M.W. 200–6000], mono- and di-fatty esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

(o) Wax esters, including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters.

(p) Vegetable waxes, including, but not limited to, carnauba and candelilla waxes.

(q) Phospholipids, such as lecithin and derivatives.

(r) Sterols, including, but not limited to, cholesterol and cholesterol fatty acid esters.

(s) Amides, such as fatty acid amides, ceramides, ethoxylated fatty acid amides, and solid fatty acid alkanolamides.

The lotions further preferably contain [by weight] from 1% to 10%, more preferably from 2% to 5%, of an emulsifier. The emulsifiers can be nonionic, anionic or cationic. Examples of satisfactory nonionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol where the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, the fatty acid soaps, e.g. sodium, potassium and triethanolamine soaps, where the fatty acid moiety contains from 10 to 20 carbon atoms. Other suitable anionic emulsifiers include, but are not limited to, the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

Other conventional components of such lotions may be included. One such additive is a thickening agent at a level from 1% to 10% by weight of the composition. Examples of suitable thickening agents include, but are not limited to: cross-linked carboxypolymethylene polymers, ethyl cellulose, polyethylene glycols, gum tragacanth, gum kharaya, xanthan gums and bentonite, hydroxyethyl cellulose, and hydroxypropyl cellulose.

The balance of the lotion is water or a $C_2$ or $C_3$ alcohol, or a mixture of water and the alcohol. The lotions are formulated by admixing all of the components together. Preferably bioluminescence generating system reagents are suspended or otherwise uniformly dispersed in the mixture.

In certain embodiments the components may be mixed just prior to use. Devices for effecting such mixture are known to those of skill in the art or are exemplified herein.

Kits containing the lotion and powders, capsular vehicles and, optionally, buffer compositions containing ATP, $Ca^{2+}$ and other ingredients required for the bioluminescence reaction are also provided.

(2) Creams

The creams are similarly formulated to contain an effective concentration typically at between about 0.1%, preferably at greater than 1% up to and greater than 50%, preferably between about 3% and 50%, more preferably between about 5% and 15% [by weight] of one ore more the bioluminescence generating systems provided herein. The creams also contain from 5% to 50%, preferably from 10% to 25%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included is in the composition at a level from 3% to 50%, preferably from 5% to 20%.

(3) Solutions and suspensions for topical application

These compositions are formulated to contain an amount sufficient to produce a visible glow, typically at a concentration of between about 0.1–10 mg/l preferably between 1 and 5 mg/l of the luciferase. The amount of luciferin is similarly between about 0.1 and 10 mg/l, although the amount can be selected based on the desired duration of the glow. The balance is water, a suitable organic solvent or other suitable solvent or buffer. Suitable organic materials useful as the solvent or a part of a solvent system are as follows: propylene glycol, polyethylene glycol [M.W. 200–600], polypropylene glycol [M.W. 425–2025], glycerine, sorbitol esters, 1,2,6-hexanetriol, ethanol, isopropanol, diethyl tartrate, butanediol, and mixtures thereof. Such solvent systems can also contain water.

Solutions or suspensions used for topical application can include any of the following components: a diluent, such as water saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as EDTA; buffers, such as acetates, citrates and phosphates; and agents for the adjustment of tonicity such as sodium chloride or dextrose. Liquid preparations can be enclosed in ampules, disposable syringes or multiple dose vials made of glass, plastic or other suitable material. Suitable carriers may include physiological saline or phosphate buffered saline [PBS], and the suspensions and solutions may contain thickening and solubilizing agents, such as glucose, polyethylene glycol, and polypropylene glycol and mixtures thereof. Liposomal suspensions, may also be suitable as pharmaceutically acceptable carriers. These may be prepared according to methods known to those skilled in the art.

These compositions that are formulated as solutions or suspensions may be applied to the skin, or, may be formulated as an aerosol or foam and applied to the skin as a spray-on. The aerosol compositions typically contain [by weight] from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as understood in the art in a quantity and under a pressure suitable to expel the contents of the container.

Solutions, may be formulated as 0.01%–10% isotonic solutions, pH about 5–8, with appropriate salts, and preferably containing one or more of the compounds herein at a concentration of about 0.1%, preferably greater than 1%, up to 50% or more. Suitable mild solutions are known [see, e.g., U.S. Pat. No. 5,116,868, which describes typical compositions of ophthalmic irrigation solutions and solutions for topical application]. Such solutions, which have a pH adjusted to about 7.4, contain, for example, 90–100 mM sodium chloride, 4–6 mM dibasic potassium phosphate, 4–6 mM dibasic sodium phosphate, 8–12 mM sodium citrate, 0.5–1.5 mM magnesium chloride, 1.5–2.5 mM calcium chloride, 15–25 mM sodium acetate, 10–20 mM D.L.-sodium β-hydroxybutyrate and 5–5.5 mM glucose.

The active materials can also be mixed with other active materials, that do not impair the desired action, or with materials that supplement the desired action.

(4) Gels

Gel compositions can be formulated by admixing a suitable thickening agent to the previously described [(3)] solution or suspension compositions. Examples of suitable thickening agents have been previously described with respect to the lotions.

The gelled compositions contain an effective amount of one or more an anti-hyperalgesic amount, typically at a concentration of between about 0.1 mg/l–10 mg/l or more of one or more of systems provided herein, from 0% to 75%, from 0.5% to 20%, preferably from 1% to 10% of the thickening agent; the balance being water or other aqueous carrier.

(5) Solids

Compositions of solid forms may be formulated as stick-type compositions intended for application to the lips or other parts of the body. Such compositions contain an effective amount of one or more of the compounds provided herein. The amount is typically an amount effective to glow when contacted with moist skin, such as lips, typically at a concentration of between about 0.1 mg/l–10 mg/l or more of one or more of the systems provided herein. The solids also contain from about 40% to 98%, preferably from about 50% to 90%, of the previously described emollients. This composition can further contain from 1% to 20%, preferably from 5% to 15%, of a suitable thickening agent, and, if desired or needed, emulsifiers and water or buffers. Thickening agents previously described with respect to lotions are suitably employed in the compositions in solid form.

Other ingredients, such as preservatives, including methyl-paraben or ethyl-paraben, perfumes, dyes or the like, that are known in the art to provide desirable stability, fragrance or color, or other desirable properties, such as shielding from actinic rays from the sun, to compositions for application to the skin may also be employed in a composition for such topical application.

2. Glowing toys and other items

Examples of uses of the bioluminescence generating systems in toys include illumination of dolls, toy vehicles, hoolahoops, yo-yos, balloons, immersible bubble generating toys, such as a toy submarine that blows glowing bubbles, and any other toy amenable to having a generally translucent covering defining a space for containment of the bioluminescence generating system and addition of the final ingredients necessary for the illumination reaction. Also contemplated herein are toys that eject or spew a fluid. For example, toy or game projectiles are contemplated that contain a luciferase and bioluminescence substrate in an oxygen-free environment. The projectiles rupture upon impact with a hard surface thereby exposing the contents to moisture in the air that contains dissolved oxygen, the bioluminescence activator, and causing reaction.

Dolls and dummies containing one or two of the bioluminescence generating system components within a transparent or translucent portion of their bodies are also contemplated herein. Addition of the remaining bioluminescence generating system component(s) results in illumination of that body part or area. For example, a doll can have a visible, translucent digestive system containing a luciferase and substrate in a water-free environment. Upon "ingestion" of water by the doll, that is addition of water through its mouth, for example, the digestive system glows or is illuminated.

Other examples of uses of the bioluminescence generating systems in toys include, but are not limited to illuminated hoolahoops, yo-yos, slimy play materials, such as those based on sodium alginate and glycerine [U.S. Pat. No. 5,310,421], such as those sold by MATTEL® as FLOAM®, GAK®, and SMUD® and moldable play materials, such as those described in U.S. Pat. Nos. 2,541,851, 3,384,498, 3,565,815, 3,634,280, 3,661,790, 3,804,654, 3,873,485, 4,076,547, 4,172,054, 4,229,790, 4,624,976 and 4,735,660, all of which are incorporated herein in their entirety. With respect to the slimy and moldable play materials, the bioluminescence generating components can be incorporated into the play material during manufacture, as liposomes, or linked to the material.

In one embodiment, the slimy play materials are fabricated from self cross-linking sodium alginate, a glycerin solution [concentration over 90%], water and preservatives.

Figure 27:
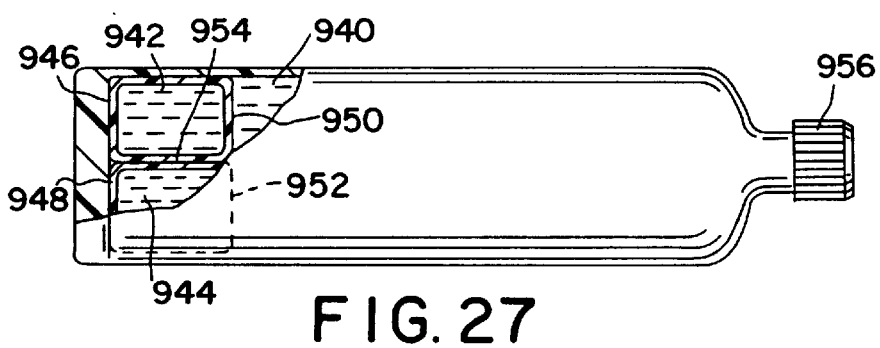
FIG. 27 is a side elevation view of a compressible tube configuration with a portion cut away.
Figure 28:
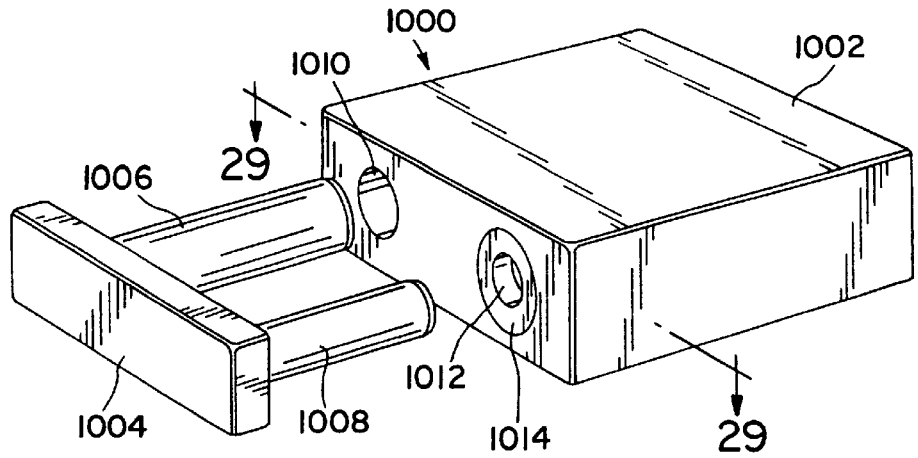
FIG. 28 is a pictorial view of a charging, or recharging, cartridge.

In an alternative embodiment, the slimy play materials are fabricated from polyvinyl alcohol and tetraborate. In another embodiment, discussed further below and in the Examples, the slimy play material is packaged in a compressible dispensing apparatus, for example, as illustrated in FIG. 27. In such an apparatus, all but one of the bioluminescence generating reagents may be provided in a compartment situated within the dispensing apparatus. A second compartment within the apparatus may contain less than all the components required to complete the slimy play material composition, and the main body of the apparatus may contain the remaining bioluminescence generating reagents and/or remaining slimy play material components.

Alternatively, three compartments within the compressible dispensing apparatus may be provided where, the third compartment contains either or both of the remaining bioluminescence generating reagents or the remaining slimy play material components. The main body of the apparatus would then contain an aqueous composition within which to mix the contents of the three compartments or the bioluminescence generating reagents or slimy play material components not contained within the third compartment.

In still other embodiments, the slime material is provided without bioluminescence generating reagents and the bioluminescence generating reagents are provided as separate compositions, in time release vehicles or other delivery vehicles, and are mixed into the material prior to use.

Another slimy material provided herein is prepared from 2–4% sodium tetraborate 2–3 ml and 2–8% polyvinyl alcohol mixed with 10 ml add 100 μgs charged aequorin or other suitable luciferase. When used with aequorin, addition of a little water [tap water or other calcium-containing aqueous medium] results in slime material that lights up. As mentioned above, one embodiment of an apparatus designed for containing and delivering the slimy play material is shown in FIG. 27. The apparatus is a compressible apparatus, for example, like a toothpaste tube, having one, two or three, preferably two, compartments inside the compressible apparatus. The compartments are formed, at least in part, of a readily rupturable material, such as plastic, such that upon squeezing the compressible apparatus, the contents of the compartments are released into the main body of the apparatus and are thereby mixed.

One compartment of the compressible apparatus may contain slime material with a luciferase and the other compartment contain the remaining bioluminescence generating components or the remaining components in slime. Alternatively, one compartment contains sodium tetraborate and luciferase and the other compartment contains the polyvinyl alcohol. In a three compartment system, one compartment may contain luciferin and luciferase packaged in the absence of oxygen. The second compartment may contain the polyvinyl alcohol and the third compartment contain the sodium tetraborate. The main body of the compressible apparatus would then contain the remaining slime material ingredients and the remaining bioluminescence generating reagents, such as calcium ion. If oxygen is the final bioluminescence generating reagent required, it may be present in the aqueous slime material composition present in the main body of the apparatus, or it may be provided by the atmosphere when the slime material is expelled. Other variations in which the components are separated are also contemplated herein.

Other alternative embodiments of the moldable play materials include those fabricated from dimethyl silicone treated with a compound of boron preferably followed by further treatment using heat and/or a catalyst, as described in U.S. Pat. No. 2,541,851; those fabricated from manogalactan gum, alkali metal borate, boric acid, high molecular weight polysaccharide, bacteriostat, fungistat, filler, colorant and perfume, as described in U.S. Pat. No. 3,384,498; those fabricated from material fillers, such as clay and talc, together with hydrocarbon petroleum distillate oil, waxy paraffinic hydrocarbon oil, a liquid silicone compound, an astringent, a humectant, glue and water, such as described in U.S. Pat. No. 3,804,654; those fabricated from synthetic resin and a wooden powder together with an oil formulation, where the synthetic resin is a rubber reinforced styrene resin and the oil used is a hydrocarbon oil utilizing an aromatic ring forming carbon, such as described in U.S. Pat. No. 4,624,976; or those fabricated from wood flower combined with a water-based gel using cross-linkable guar gum as a gellant, such as described in U.S. Pat. No. 4,735,660.

The glycerin based slimy play materials, such as those described in U.S. Pat. No. 5,310,421] contains 2.5–4.0 by weight 3.33 weight %, of a self-crosslinking sodium alginate; 1.0–3.5 weight % of a glycerin and water composition in excess of 90% glycerin; a preservative; 4.0 weight % NaCl; and water, and can include 0.04–0.08 weight % of a colorant. As modified herein, it will also include up to all but one component of a bioluminescence generating system, such as a luciferase, such as Renilla or Vargula or a firefly luciferase, or a luciferin and luciferase, such as the Aequorin photoprotein and EDTA. A second mixture of the slime material will contain the remaining components.

A preferred slimy material contains 2.5–4.0% by weight, preferably 3.33% by weight, of a self-crosslinking sodium alginate; 1.0–3.5% by weight of a glycerin and water solution in excess of 90% glycerin; one or more preservatives; 2.0–7.0%, preferably about 4%, by weight NaCl; and water, and can include 0.04–0.08% by weight of one or more colorants. The material will also include up to all but one component of a bioluminescence generating system, such as a luciferase, such as Renilla or Vargula or a firefly luciferase, or a luciferin and luciferase, such as the Aequorin photoprotein and EDTA.

The slimy play material may be made to glow by contacting it with a second mixture of the slime material containing the remaining components of the bioluminescence generating system or by contacting it with the air or an aqueous composition, where molecular oxygen or calcium ion is required to complete the reaction. The second mixture can also contain a different colorant, so that upon mixing not only will the material glow, it will change color.

The concentrations of bioluminescence system components, such as luciferase, will be those sufficient to generate a visible glow. The concentrations of luciferase can be empirically determined, but generally will be between about 0.1 and 1 mg per liter of material. The amount of luciferin generally will be in excess. The luciferases and luciferin and other components can also be provided as time release vehicles in the material or provided separately for subsequent addition.

This slime material can be packaged as a kit or article of manufacture containing a first slime composition containing all but at least one bioluminescence generating reagent, and a second slime composition containing the remaining components. The kit will include instructions for mixing the two compositions to produce a glowing composition. The kit can also contain additional compositions or vehicles or dried powders of bioluminescence generating reagents so that they can be added prior to use so that the material can be reused.

In another embodiment, discussed further below and in the Examples, the slimy play material is packaged in a compressible dispensing apparatus, for example, as illustrated in FIG. 27. In such an apparatus, up to all except for one of the bioluminescence generating reagents may be provided in a compartment situated within the dispensing apparatus. A second compartment within the apparatus may contain less than all the components required to complete the slimy play material composition, and the main body of the apparatus may contain the remaining bioluminescence generating reagents and/or remaining slimy play material components.

Alternatively, for example, three compartments within the compressible dispensing apparatus may be provided such that the third compartment contains one or all of the remaining bioluminescence generating reagents or the remaining slimy play material components. The main body of the apparatus would then contain a composition, typically an aqueous solution within, which to mix the contents of the three compartments or the bioluminescence generating reagents or slimy play material components not contained within the third compartment.

In still other embodiments, the slime material is provided without bioluminescence generating reagents and the bioluminescence generating reagents are provided as separate compositions, in time release vehicles or other delivery vehicles, and are mixed into the material prior to use.

Another slimy material provided herein is prepared from 2–4% sodium tetraborate 2–3 ml and 2–8% polyvinyl alcohol mixed with 10 ml add 100 μgs charged aequorin or other suitable luciferase. When used with aequorin, addition of a little water [tap water or other calcium-containing composition] results in slime material that lights up. As mentioned above, one embodiment of an apparatus designed for containing and delivering the slimy play material is shown in FIG. 27. The apparatus is a compressible apparatus, for example, like a toothpaste tube, having one, two or three, preferably two, compartments inside the compressible apparatus. The compartments are formed, at least in part, of a readily rupturable material, such as plastic, such that upon squeezing the compressible apparatus, the contents of the compartments are released into the main body of the apparatus and are thereby mixed.

One compartment of the compressible apparatus may contain slime material with a luciferase and the other compartment contain the remaining bioluminescence generating components or the remaining components in slime. Alternatively, one compartment contains sodium tetraborate and luciferase and the other compartment contains the polyvinyl alcohol. In a three compartment system, one compartment may contain luciferin and luciferase packaged in the absence of oxygen. The second compartment may contain the polyvinyl alcohol and the third compartment contain the sodium tetraborate. The main body of the compressible apparatus would then contain the remaining slime material ingredients and the remaining bioluminescence generating reagents, such as calcium ion. If oxygen is the final bioluminescence generating reagent required, it may be present in the aqueous slime material composition present in the main body of the apparatus, or it may be provided by the atmosphere when the slime material is expelled. Other variations in which the components are separated are also contemplated herein.

Other toys, games, novelty items, clothes, accessories, foods, beverages, fountains, water dispensing apparatus, soaps, creams, cosmetics and sporting equipment amenable to bioluminescence are further embodiments of the presently disclosed combination. Thus, any article of manufacture or substance capable of modification to allow bioluminescence thereof is contemplated herein.

Articles of manufacture that are amenable to use with the bioluminescence generating systems provided herein are well known [see, e.g., U.S. Pat. Nos.: 5,415,151, 5,018,449, 3,539,794, 5,171,081, 4,687,663, 5,038,963, 4,765,510, 4,282,678, 5,366,108, 5,398,827, 5,397,014, 5,219,096, 5,305,919, 5,184,755, 5,029,732, 4,214,674,4,750,641, 4,676,406], which describe devices useful as toy water guns or vessels for beverages or creams and lotions. To be amenable to use in the embodiments described herein, each may require some modification, such as, for example, addition of a mixing chamber.

In light of the disclosure herein, such modification will be apparent. Some of the patents describe other toy devices, training mock weapon devices, dolls, and beverage containers and dentifrice containers [i.e., toothpaste tubes]. In the simplest modification, powdered or capsular vehicles containing bioluminescence generating systems may be added to the water-holding chambers of the toy gun or other water spewing toy. As the powder dissolves or the vehicle releases its contents, typically luciferin and luciferase, contact with the water in the gun will cause the bioluminescence reaction to occur.

As is apparent from the above, toy guns are well known items and materials and specifications for manufacture thereof are also well known [see, the above list and see, also, U.S. Pat. Nos. 5,029,732, and 5,415,151]. Any single chamber squirt gun may used in combination with biolumines-cence generating systems herein by mixing the components in the gun chamber. Of course the selected system should be one that has sustained illumination. Alternatively, pellets of encapsulated bioluminescent components, such as the aequorin photoprotein or the Renilla luciferase and luciferin, may be added to water in the gun chamber. In the case of the aequorin photoprotein and Renilla luciferase, added tap water may be sufficient. For the Renilla system the pellets may contain the luciferase and luciferin or either. The remaining component will be added to the gun chamber. If pellets are used, the pellets will slowly release their contents thereby providing for a continuous glow.

Similar apparatus and designs are also used for any fountain or water propelling device. Any such device [see, e.g., U.S. Pat. No. 5,360,142] may be modified to include a bioluminescence system to produce a glowing stream.

In all of these devices, the water, for example, can be tap water or a selected buffer, particularly phosphate buffered saline. The items may packaged as kits with the packaged luciferin, luciferase, and including the water.

a. Single chamber toy guns and other toy weapons that shoot pellets or liquid

Numerous toy guns and other toy weapons that shoot pellets or liquid, in addition to those exemplified herein, are suitable for use in combination with the bioluminescence generating systems herein. The toy weapons may be loaded with a composition containing microspheres of luciferin and/or luciferase, or with lyophilized luciferin/luciferin, or other mixtures as described herein. Suitable toy weapons and devices that shoot jets or sprays of water are described in the following sampling of U.S. Pat. No. 5,462,469 [toy gun that shoots bubbles]; U.S. Pat. No. 5,448,984 [toy gun that shoots balls and water and can be modified to shoot light or temperature sensitive pellets, which should be stored under appropriate conditions or appropriately packaged, that release luciferin/luciferase when exposed to light]; U.S. Pat. Nos. 5,439,139; 5,427,320; 5,419,458; 5,381,928; 5,377,656; 5,373,975; 5,373,833 and 5,373,832 [which describe toy guns that rely upon a pressurizable bladder for release of air pressure to shoot a projectile, which can be modified to shoot projectiles of encapsulated luciferin/luciferase]; U.S. Pat. No. 5,370,278 [which describes liquid from a port mounted to a headband]; U.S. Pat. Nos. 5,366,108; 5,360,142 [which describes a supply and delivery assembly for use in combination with a pump type water gun or other water propelling device]; U.S. Pat. Nos. 5,346,41 8; 5,343,850 [which describes a projectile launcher for use in combination with the pellets provided herein]; U.S. Pat. Nos. 5,343,849; 5,339,987 [which describes water guns that have at least one pressurizable air/ water storage tank, a pressurizing mechanism, a channel of release for shooting water and a release mechanism]; U.S. Pat. Nos. 5,326,303; 5,322,191; 5,305,919; 5,303,847 [which describes a device worn on a user's hand with sheaths for the tips of the fingers that includes a housing for a water reservoir, a water pump and electrical motor and a battery pack to be secured to the user's body]; U.S. Pat. Nos. 5,292,032; 5,284,274 [which describes an action to system including a capsule for containing water, which will herein contain components of a bioluminescence generating system, having an orifice and a plunger and a spring loaded mechanism for driving the water from the orifice. The action toy may be configured as a shotgun accepting a plurality of prefilled shell capsules into its breechblock for firing through its barrel, as a missile launcher in which the capsules are mounted to the front of the launcher and the water is ejected directly from the capsule against the target, or as a crossbow with the bow loading the spring-loaded mechanism and a water stream obtained on release of the bow]; U.S. Pat. No. 5,284,272 [which describes a bottle and cap combination for spewing liquid]; U.S. Pat. Nos. 5,256,099; 5,244,153; 5,241,944; 5,238,149; 5,234,129; 5,224,625; 5,213,335; 4,854,480; 5,213,089; 5,184,755; 5,174,477; 5,150,819; 5,141,467; 5,141,462; 5,088,950; 5,071,387 [which describes a figurine-shaped water squirting toy]; U.S. Pat. No. 5,064,095 [which describes a water cannon apparatus]; U.S. Pat. Nos. 5,029,732; 5,004,444; 4,892,228; 4,867,208 [which describes an apparatus for storing and dispensing fluid under pressure]; U.S. Pat. Nos. 4,808,143; 4,784,293, 4,768,681; 4,733,799; 4,615,488 and many others. U.S. Patent No. 5,415,151 describes a toy gun that launches projectiles that can be adapted for shooting the pellets, such as light sensitive pellets that are degraded upon exposure to light, provided herein.

b. Bubble-making toys

Soap bubbles are blown from water solutions or other aqueous composition containing soap or another surfactant. A great variety of bubble formulations are available, including those that feature special effects in bubble making. There are solutions for making large bubbles, "long lasting" bubbles, split bubbles, self-healing bubbles, multiple bubbles, vanishing bubbles, flaking bubbles, bursting bubbles, high and/or far-flying bubbles, sinking bubbles etc. In general, many anionic, non-ionic or amphoteric aqueous solutions with low surface tension are suitable for bubble or foam-making when air or other gases are blown into such compositions.

Such compositions, preferably those that have near neutral pH, can be combined with the components of the bioluminescence generating systems provided herein. In particular, a mixture of luciferase and luciferin, such as the Renilla system or firefly system or Cypridina system, preferably in the form of pellets or microspheres, such as liposomes or other time release capsule, can be added to the bubble mixture. When used, the air added to the mixture will cause a glow, or a glow will be produced as the contents of the pellets are released into the composition. Alternatively, one or more component of the bioluminescence generating system may be added to the bubble making composition, such as, for example, a luciferase and any necessary activators, and the remaining component(s), e.g., a luciferin, may be directly applied to bubbles using a fine spray from an atomizer or other suitable spray or misting means.

In addition, a fluorescent protein, such as GFP, BFP or a phycobiliprotein, may be added to the bubble-making composition and then illuminated using an external light source. For example, bubbles containing a fluorescent protein may be produced in a room illuminated with light of an appropriate wavelength to cause the fluorescent protein to fluoresce.

Alternatively, the fluorescent protein may be added to the bubble-making composition containing all the components of the bioluminescence generating system to effect a change of the color of the bubbles. For example, the fluorescent proteins may be added to the bubble-making composition directly or may be added in time-released or slowly-dissolving microspheres or liposomes, such that release of a fluorescent protein in the bubble composition, such as, for example, GFP or a phycobiliprotein, introduces a change in the color of the bubbles. It is particularly advantageous to have the fluorescent protein released into the composition after the container has been opened and used. A single bottle of bubble-making solution will be amenable to the production of more than one color of bubbles. For example, microparticles or liposomes susceptible to breakdown by exposure to air or by agitation by the wand or stick used for blowing bubbles are of particular interest.

Kits containing such soap compositions, with preferably a moderate pH [between 5 and 8] and bioluminescence generating reagents, including luciferase and luciferin and the fluorescent protein are provided herein. These kits, for example, can be used with a bubble-blowing or producing toy. These kits can also include a reloading or charging cartridge, such as the cartridges provided herein.

Toys that produce bubbles include bubbles with wand for blowing, bicycles, flying toys, dolls, swords, toy musical instruments, bubble beards, and numerous other toys are well known [see, e.g., U.S. Pat. No.: RE 32,973, which describes a toy bubble-blowing lawn mower; U.S. Pat. No. 4,511,497, which describes a non-toxic non-irritating bubble composition for toys, U.S. Pat. Nos. 2,579,714; 5,480,334; 5,041,042; 5,478,267; 5,462,469; 5,419,728; 5,393,256; 5,366,402; 5,348,507; 5,322,464; 5,304,085; 5,269,715; 5,224,893; 5,183,428; 5,181,875; 5,156,564; 5,135,422; 5,080,623; 5,078,636; 4,957,464; 4,955,840; 4,943,255; 4,923,426, 4,867,724; 4,861,303; 4,840,597; 4,808,138; 4,804,346; 4,764,141; 4,700,965; 4,556,392 4,334,383; 4,292,754; 4,246,717; and many others].

c. Board/Card Games

Board games, card games and similar entertainment items may be used in combination with the bioluminescence generating systems described herein. The boards or cards may be constructed of paper or fabric, as described herein, or may be constructed of plastic or other polymer amenable to covalent or non-covalent attachment of bioluminescence generating compontents.

A particular portion of the game board or a card piece is covered or impregnated one or more up to all but one of the bioluminescence components. A developing wand or sponge or similar apparatus is impregnated or coated or dispenses the remaining bioluminescence component(s) [developing reagents]. Contacting, such as by wiping, the card piece or game board with the developing wand or sponge or contents of the dispensing apparatus will produce a glow.

The developing reagents can be applied to the developing wand or sponge in various forms. For example, the developing reagents may be in solution or suspension and the sponge or wand soaked in the solution then sealed in an air-tight packaging to be opened immediately before use. Alternatively, the developing reagents may be lyophilized or dessicated and applied in powder form to the wand or sponge. immediately before use, water is added to the wand or sponge and then wiped on the game board or card piece.

Alternatively, the board and pieces may include adsorbed or absorbed lyophillized bioluminescence-generating reagents. Contacting these items with water, containing the appropriate salts and buffers, such as calcium, if for example, the aqueorin system is used, or ATP if the firefly system is used.

The bioluminescence components applied to the game board or card piece can be applied in a particular pattern, for example to spell a word or illustrate an instruction. Preferably, the bioluminescence system chosen will be capable of repeated use. For example, the Renilla system, is among the preferred systems. The luciferase can be linked to the pieces, and the luciferin can be applied to the board or card and a new developing wand or sponge used each time the game is played.

Alternative embodiments will be appreciated, for example, the game can be an educational one in which the player uses the developing wand or sponge to reveal the correct answer to a question. Similarly, the game board may be a puzzle where a "hidden" illustration or message is revealed by wiping the completed puzzle with the developing wand or sponge.

d. Toy "Eggs" or other encapsulated items

Egg-shaped (or any other desired shape) toys containing a liquid or paste that glows upon exposure to ambient air are a further example of a combination contemplated herein. The ingredients of the egg composition include a luciferin and luciferase, such as the Cypridina or Vargula luciferin and luciferase, which requires oxygen for activation. The liquid or paste is introduced into the "eggs" the eggs are sealed under nitrogen or other suitable gas, other than oxygen or air. Upon exposure to air, by opening or cracking the egg, the egg composition glows. This principle can be adapted to other uses, such as sphere shaped macrocapsules that may be shot from a toy gun and burst upon impact, in a manner similar to paint ball guns currently used to shoot paint balls at targets for marking. In practice, water is de-oxygenated, for example by bubbling argon or nitrogen gas through it. The de-oxygenated water is then used to mix the bioluminescence generating components, other than molecular oxygen. The mixing should take place under strictly conditions in which air or oxygen is excluded, such as in a hood under nitrogen, in order to prevent exhaustion of the bioluminescence-generating components.

In one embodiment, to produce a realistic egg-like mixture, approximately 1 to 2 mg of a luciferin/luciferase composition per 30 ml of egg volume is combined with a suitable thickener, such as hydroxymethyl cellulose, to provide the consistency of a real egg. The "shell" of the egg is formed of a suitable material which excludes oxygen (air) and is readily opened by the consumer before use. For example, the egg mixture can be packed into paper mache and covered with wax to provide an airtight seal. Similarly, the "shell" may be formed from a polymer, such as a plastic, that is airtight but readily broken when desired.

e. Footbags, Bean Bags and Balls

Glowing footbags, bean bags and balls are also provided herein. Footbags, such as the HACKY SACK, which is a registered Trademark of Wham-O Corporation, described in U.S. Pat. No. 4,151,994, are generally constructed of an outer leather casing having a diameter of about three inches, which is filled with small granules, such as beans or other granular material [see, also U.S. Pat. Nos. 5,429,351, 4,963, 117, 4,717,158, and 4,002,839]. The sack is used to play a game in which players kick the sack between one another, trying to keep the sack in motion and off the ground, without using their hands.

Contemplated herein are footbags and balls that glow as they are kicked about by the players. The bags are fabricated from an inflatable translucent material, such as a plastic, Similar to the egg mixture described above, the granules in the footbag are made in an oxygen free environment and packaged such that air/oxygen is excluded until the sack is in use. For example, the granules are made of a gelatinized mixture of bioluminescence generating system components excluding molecular oxygen and are packaged in an oxygen free package, such as dry nitrogen packaging, commonly used in marine electronics, or in rupturable liposomal pellets.

The granules can be covered in a flexible plastic of varying thicknesses to allow for the timed ingress of oxygen across the plastic membrane. As the footbag is repeatedly kicked by the players, the mechanical stress on the granules allows more oxygen to react with the bioluminescence generating components contained therein, creating more light.

An alternative embodiment contemplated herein involves partitioning the granules within the footbag using, for example, a semi-permeable membrane material that permits slow permeation of the compositions contained in the two compartments thereby formed. One compartment is then filled with all but one or more bioluminescence components and the other compartment is filled with the remaining components. As the footbag is kicked about, the mechanical stresses on the separating membraned force the contents of the two compartments to mix, thereby providing flashes of light or periods of illumination followed by non-illumination. For example, in one compartment, a calcium containing composition can be added to the beads, and in the other compartment, a coelenterazine-charged aequorin is added. When the footbag is kicked, flashes of light are produced.

The covering of the footbag must be translucent, transparent or some combination thereof to allow the light generated to be visible. Thus, the "sack" can be formed from clear nylon webbing, translucent or transparent pliable plastic, translucent or transparent cloth or similar material.

f. Figurines

Glowing figurines are also provided herein. Figurines may be of any size or shape and preferably contain at least one chamber that holds liquid. The figurine may be cast, molded or manufactured from any suitable material. Preferably a portion of or the entire figurine is translucent to the wavelength of light produced in the bioluminescence generating reacton. The figurine may be in any design or theme, such as characterizations of entertainment and sport celebrities, memorabilia, slogans and logos, trademarks or other promotional items, animals, Christmas ornaments or other inanimate objects. For example, small figurines may be placed in areas of dim lighting, e.g., on tables in restaurants, that contain one or more component of the bioluminescence generating system, such as a luciferase. The remaining components of the bioluminescent reaction, i.e., a luciferin and any necessary activators, are added at the desired time and the figurine glows.

In another embodiment, one or more component(s) of the bioluminescence generating system may incorporated into or linked to the material from which the figurine is fabricated. The remaining components of the bioluminecsent reaction may be sprayed or applied to the surface of the figurine to initiate the bioluminescent reaction.

3. Glowing textiles and paper products

The bioluminescence generating systems described herein are also contemplated for use with textiles and paper. One or two of the bioluminescence generating system reagents are applied to the textile or paper and the remaining components are added when illumination is desired. For example, the luciferase in association with the bioluminescence substrate may be applied to the textile or paper, through covalent or non-covalent interaction. When water, or other appropriate activator, is applied to the material, illumination ensues. Examples of uses for the textile include the fabric portion of an umbrella, clothing, towels, the fabric portion of artificial plants or flowers, toys having a fabric component or any item susceptible to manufacture from textile material.

With respect to paper, the luciferase may be applied to the paper in association with the bioluminescence substrate. The paper glows upon addition of the bioluminescence activator to the paper. Thus, if the bioluminescence activator is water, addition of water to the paper, for example as an aerosol, produces a glow on the paper. The paper may also be illuminated by "writing" upon it with one or two of the bioluminescence generating system components then "writing" or spraying over those components with the remaining component(s). As with the other systems disclosed herein, the critical aspect to operation is maintaining at least one of the bioluminescence generating system components separate from the other components until illumination is desired. The paper may be in almost any form or of almost any type, such as writing paper, wrapping paper, boxes, poster paper, books, paper jewelry, paper towels, napkins or other paper products.

4. Foods and beverages, including ice cubes

Examples of beverages and foodstuffs amenable to combination with bioluminescence systems include, but are not limited to, alcoholic beverages, as well as sodas and juices, and such foods as applesauce and mashed potatoes. Further, bioluminescence generating systems can be chosen and adapted for use in such foodstuffs as cakes and ice creams or almost any other edible item. Considerations in combining bioluminescence systems with food and/or beverages are primarily the stability of the system throughout processing of the food or beverage, unless the system is added subsequent to any such processing; the ability to contact the system with its finally required ingredients to produce bioluminescence; and taste of the components of the system with the foodstuffs to which they are added.

Bioluminescent food products are also contemplated herein. Such products, amenable to combination with the bioluminescence generating systems described herein, include those that may be stored between about 0° C. and 35° C. Generally, once the luciferase or bioluminescence substrate is added to the food product, it cannot be heated above about 100° C. Thus, food products requiring cooking prior to consumption also can be cooked prior to addition of either the luciferase or bioluminescence substrate.

Examples of food products amenable for use in combination with the bioluminescence generating systems described herein include, but are not limited to, icings and other toppings or sauces, cookies, biscuits, and similar prepared foods. Bioluminescent icings, for example, may be prepared by including the luciferase and bioluminescence substrate in a dehydrated icing mixture. Addition of water, just prior to use causes the mixture to glow. Alternatively, the bioluminescence activator and either the luciferase or bioluminescence substrate may be included in the prepared icing mixture and the absent bioluminescence generating system component stirred into the icing just prior to use.

Alternatively, food products may be produced to include a fluorescent protein, such as a phycobiliprotein or a green or blue fluorescent protein, and then illuminated using an external light source. For example, icing containing fluorescent protein may be served in a room illuminated with light of an appropriate wavelength to cause the fluorescent protein to fluoresce. Similarly, a fluorescent protein may be included in an ice cream mixture, in an ice cream topping sauce, in a salad dressing, in cakes, puddings or similar food product and the food then subjected to an external light source of appropriate wavelength to initiate the fluorescence.

a. Beverages

Beverage products are likewise contemplated for use herein in combination with the bioluminescence generating systems described herein. As with other embodiments, at least one of the bioluminescence generating system components is excluded from the beverage until bioluminescence is desired. For example, a container/bladder apparatus, as described generally above and in detail below, maintains the luciferase and bioluminescence substrate separate from the beverage. Upon opening of the container, the luciferase and substrate are added to the beverage causing it to glow.

Alternatively, the beverage may be produced and packaged already containing one or two of the bioluminescence generating system components, such that addition of the remaining components causes a glow. An example of such a beverage is bioluminescent beer, wine, champagne or a soft drink. In this embodiment, the yeast used to produce the alcohol component of the beer or other beverage, are genetically transformed to contain, for example, a gene encoding a luciferase and the complementary genes necessary to direct the yeast to manufacture and secrete the luciferase. Assuming $O_2$ or air is the bioluminescence activator, then when a glow is desired, the bioluminescence substrate is added to the beer.

Another example of a bioluminescent beverage contemplated herein is a soft drink containing two of the three bioluminescence generating system components. When bioluminescence is desired, a third bioluminescence generating system component is added. If the bioluminescence generating system is, for example, the Aequorin system or the Renilla system, then the Aequorin luciferase with bound luciferin or the Renilla luciferase and the luciferin may be included in the soft drink and the bioluminescence activator, $Ca^{2+}$ [for the aequorin system] or dissolved $O_2$, added to the beverage to cause a glow. Suitable vessels for such beverages are provided herein [see, EXAMPLES] and also are known to those of skill in the art [see, e.g., U.S. Pat. No. 5,398,827].

Similarly, a soft drink beverage can be produced containing all the bioluminescence generating system components except, for example, dissolved oxygen where the bioluminescence generating selected requires oxygen to complete the bioluminescent reaction. In lieu of carbon dioxide, the beverage may have another gas or gasses dissolved therein, for example nitrogen, helium, nitrous oxides or helium oxygen (heliox). The soft drink is packaged under oxygen free conditions and, upon opening of the soft drink container and exposure of its contents to the air, the oxygen in the air activates the bioluminescent reaction causing the soft drink to glow.

In each of the above embodiments, it is also contemplated that slowly-dissolving or time releasing microparticles, such as, but not limited to liposome or isolated endosomes, may be included in the beverage that contains additional bioluminescent components. Microparticles may contain, for example, one or more luciferases, a phycobiliprotein, a green or blue fluorescent protein, a luciferin or any mixture or combination thereof. Upon dissolution of the microparticle or release of the contents by other means, the contents of the microparticle are released into the beverage or other liquid, resulting, for example, in a change in the color of the emitted light the beverage, an change in the color of the bioluminescent light and/or an increase in the intensity of the emitted light of the entire beverage or just a portion thereof. By selecting the appropriate microparticle(s), the release of one or more component of the reaction may be effected sequentially or concurrently. Thus, drinks in which several glowing colors are produced are contemplated herein. Multiple color changes are effected by the appropriate selection of bioluminescence generating agents and/or fluorescent proteins.

For example, an appropriate time-released or slowly-dissolving microparticle containing a GFP or a phycobiliprotein may be added to a beverage containing the Renilla or aequorin bioluminescence generating system. Upon dissolution or release of the fluorescent protein into the medium, the initial blue color of the glowing beverage is converted to another color, e.g., converted to a green color by the GFP.

The inclusion of an additional microparticle containing a phycobiliprotein with an absortion maxima in the green spectra, in which the microparticle has been selectively designed to dissolve or release into the beverage after release of the GFP, would result in the beverage once again changing color to, for example, red. The color of the beverage may be changed sequentially and repeated as many times as desired. The number of possible color changes will depend on the type of beverage, the desired colors and the duration of each color. Any beverage is contemplated for the color changes as described herein, such as soft drinks, alcoholic beverages, juices and the like.

Alternatively, the color change may be designed to be effected in only a portion of the beverage. For example, microparticles that contain a fluorescent protein in combination with a composition that has a higher or lower specific density than the beverage [e.g., a saturated sucrose solution or any sutiable non-toxic, highly viscous solution having a higher specific density]. Dissolution or release of the contents of the microparticle results in the formation of a biphasic solution in which, for example, the top portion of the beverage glows blue whereas the bottom portion of the beverage containing the released fluorescent protein [e.g., GFP or a phycobiliprotein] glows green, red or another color. The concentration of the fluorescent proteins and the selection of a higher or lower density liquid and percentages to be used herein may be determined empirically by one of skill in the art.

The color of each layer may be changed sequentially or the color change may be effectively repeated in any order depending on the microparticle or macroparticle employed [e.g., inclusion by direct addition, time releasing particles or thermal or pH sensitive microparticles].

b. Ice

Ice containing bioluminescent components, such as lyophilized components or encapsulated components is contemplated herein. Upon addition to a liquid containing any remaining components or exposure to air, the contents of the ice will be released as they melt to produce a glow. The ice may be in any shape or form. Examples of ice formations, include but are not limited to, geometric shapes, such as spheres and cubes; ice formations made from precast molds, such as figurines, icicles, popsicles; shaved ice, such as snow cones or imitation snow for recreational activity like skiing, sledding or snow-mobiling; ice sculptures, where the ice glows and/or in combination an inanimate object frozen within the ice that glows. In addition, ice used as a surface for recreational ice skating or hockey is also contemplated herein.

The ice may contain one or more of the bioluminescence generating components. For example, the ingredients of ice may include a luciferin and/or luciferase, such as the Cypridina or Vargula luciferin and luciferase, which requires oxygen for activation. Luciferases isolated from different species that result in the production of light other than green or blue, e.g., Aristostomias or Pachystomias which emit red light, or additional components which alter the wavelength of the emitted light, e.g., a green fluorescent protein or a phycobiliprotein, used in conjunction with the luciferase are also contemplated herein.

In practice, water is de-oxygenated, for example, by bubbling argon or nitrogen gas through it. The de-oxygenated water is used to mix all of the bioluminescence generating components besides molecular oxygen. The mixing should take place under strict conditions in which air or oxygen is excluded, such as in a fume hood under nitrogen, in order to prevent exhaustion of the bioluminescence-generating components.

The water is placed in a tray, a vessel, a precast form of a particular shape or design, stored or maintained under an inert atmosphere and snap frozen using liquid nitrogen. The resulting ice is packaged in a sealed container under an inert atmosphere lacking molecular oxygen (e.g., argon or nitrogen). Upon exposure to air or a liquid containing dissolved oxygen, the ice glows.

Alternatively, one or more component of the bioluminescence generating system may be applied to the surface of the ice to initiate or re-generate the bioluminescent reaction. This method is particularly suitable for production of a glowing ice surface, such as an ice skating rink. The components of the reaction may be added to the water contained within the Zamboni ice cleaning machine. The water from the machine is overlayed over the existing ice, which contains (or is first coated on the surface) at least one component of the bioluminescence generating system, as a thin coating of a composition that contains the other one or more component(s) of the bioluminescence generating system. As the two layers meet, the bioluminescence generating system is produced or restored and the ice glows.

Furthermore, microparticles containing additional bioluminescence generating components may be added to water prior to snap freezing. For example, microparticles containing or coupled to a phycobiliprotein or a green/and or blue fluorescent protein (GFP) can be produced. The additional components may also be added to the surface of the ice after freezing. As with the beverages, described above, as the microparticles dissolve in the ice or as the ice melts, the fluorescent protein or other components are released. The presence of the fluorescent protein converts the wavelength of the light emitted from the surface or interior of the ice, which can include the components of a bioluminescence generating system, thereby changing the color of the ice or liquid, for example, from blue to green or red. The addition of GFP also increases the intensity of the green light emitted about 2–5-fold. Thus, a beverage containing such ice would not only change color as time proceeds but also glow more brilliantly. The light insenity of the liquid could also be enhanced by the addition of microparticles containing an appropriate luciferin or activator that upon dissolving would provide additional substrate to promote the bioluminescent reaction.

The components may also be combined with dry ice, which as it sublimes, will release the components that contact with moisture condensing in the air. This will produce a glowing fog for use, for example, in theatrical productions.

c. Other foods

Other foods contemplated herein include a transgenic corn that expresses luciferase. The corn is served with butter containing luciferin, particularly coelentrazine, and as result glows.

Alternatively, the popcorn is engineered to express a fluorescent protein. When exposed to the appropriate light, the corn will glow.

5. Jewelry, Clothing and Other Items of Manufacture

The bioluminescence generating systems and fluorescent proteins can be used in combination with articles of manufacture that include jewelry, clothing, figurines and other such items. In particular, these items may be manufactured from matrix materials or from mixtures of the matrix material and other materials. Alternatively, the matrix material may be coated on or impregnated in such articles. Bioluminescence generating reagents, particularly, luciferases can be linked to the matrix material. When a glow is desired the article can be contacted with composition containing the remaining components.

In addition, articles, such as clothing, particularly, T-shirts and sports gear, and paper items may be sprayed with two compositions, the first containing less than all of the necessary reagents and the second containing the remaining reagents.

In other embodiments, the article may be made of two vessels separated by a removable separating means, so that when desired components contained therein communicate and react resulting in bioluminescence.

6. Fountains

Numerous fountains and other water spraying apparatus and devices for use in such apparatus, in addition to those exemplified herein, are suitable for use in combination with the bioluminescence generating systems herein [see, e.g., U.S. Pat. Nos.: 5,480,094; 5,472,140; 5,439,170; 5,402,836; 5,388,285; 5,381,956; 5,337,956; 5,288,018; 5,167,368; 4,852,801; 3,894,689; 3,889,880; 3,838,816; 3,820,715; 3,773,258; 3,749,311]. For use herein, the fountains will be modified or adapted [see, e.g., EXAMPLES] so that jets of liquid containing bioluminescent will spew.

Fountains can be recharged, for example, by adding additional substrate and other activators. Spent substrate should be removed, such as by passing the water through an affinity matrix specific for the oxidized substrate.

7. Non-Tobacco Cigarettes

Also contemplated herein is a novelty item that is shaped like a cigarette and that includes a bioluminescence generating system, which produces glowing "smoke" upon exhalation by the user. The user contemplated herein is an adult former smoker who derived pleasure from blowing smoke rings. The toy cigarette can be made, for example, by placing, under oxygen free conditions, a lyophilized, micropulverized mixture of the bioluiminescence generating system components into liposomes, as described above, or other packaging material, such as porous plastic microspheres, made from TYGON or other biocompatible non-toxic material. The liposomes (or other packaging) are selected to be of a suitable size to facilitate or permit passage into the bronchioles of the user. The liposomes are preferably on the order of 5–10 $\mu M$ in diameter and are situated in a tubular delivery vehicle [the "cigarette"].

An example of an appropriate delivery vehicle is a thin glass vial surrounded by plastic, similar to vials known to those of skill in the art that are used for storing amyl nitrate, betadine and benzoin solutions. The delivery vehicle is preferably shaped and sized like a standard cigarette. The plastic covering is preferably cylindrical with each end open to allow for the passage of air upon inspiration. The plastic covering is surrounded by a filter material that allows passage of the liposomes from the device, but prevents the accidental inhalation of particulates, such as glass, if the vial is broken. Additional filters, having pore sizes of about 10 $\mu M$, are placed at either end of the "cigarette" as a further barrier to inhalation of any material larger than the liposomes. Solid plastic or similar material caps may be situated over each end of the "cigarette" to prevent the liposomes contained therein from falling out. These caps would be removed just prior to use of the "cigarette", to permit the free flow of air through the device. The liposomes are preferably held within the delivery vehicle by friction.

In operation, the user will inhale the liposomes or similar encapsulating vehicles, which release their contents upon contacting the lungs. The humid environment of the bronchial tree then provides the water and oxygen necessary to complete the bioluminescence reaction. Upon exhalation, the air leaving the users lungs is illuminated, providing glowing "smoke". If the packaging apparatus chosen for the bioluminescence generating components is a porous plastic microsphere, such as TYGON, then the bronchiolar-ciliary transport mechanism of the body will transport the spent microspheres out of the bronchia and into the digestive system. Because plastic is biologically non-reactive, the microspheres will be passed from the body through normal excretory pathways without eliciting an immune or toxic reaction.

8. Fish and Fish Food and Fish Bait

Also contemplated herein are genetically engineered fish that express luciferin or, preferably luciferase, and food therefor. Such fish may be produced may any method known to those of skill in the art for preparation of transgenic fish. For example, to produce the fish, fish eggs are transfected with a gene encoding a particular luciferase and any other genes or regulatory sequences necessary to direct the fish to manufacture and express the luciferase, using methods known to those of skill in the art. Methods for generating transgenic fish are known [see, e.g., U.S. Pat. Nos. 5,512, 421, 5,510,099, 5,489,742, 5,476,779, 5,416,017 and 5,166, 065; see, also, Ozato et al. (1986) *Cell Differ. Devel.* 19:237–244, Inoue et al. (1990)*Cell Differ. Devel.* 29:123–128, Rokkones et al. (1989) *J. Comp. Phviol.B* 158::751–758, and Guyomard et al. (1989) *Biochimie* 71:857–863, which describe preparation of transgenic medaka, medaka, salmon and trout, respectively]. Transgenic fish of numerous species have been prepared, providing the skilled artisan with a variety of procedures for developing transgenic fish. Thus, using a transfection methods known to those of skill in the art and methods for introduction and expression of luciferase, transgenic fish that express a luciferase are prepared. Desirably, the fish express the luciferase on cell surfaces, such as by incorporating the luciferase into DNA encoding a membrane-spanning protein, or express the luciferase so that it is secreted into the digestive systems or mouths of the fish.

The resulting fish are fed food containing an appropriate luciferin or luciferins [or luciferase] and any additional bioluminescence generating reagents required. Typically, the luciferin will be present in the fish food at concentrations ranging from about 1 part per million (ppm) to about 1 part per 10, weight/weight. As the luciferin, bioluminescent activators and other system components come in contact with the luciferase expressed by the transgenic fish, the fish or selected organs or tissues will glow. For example, if the luciferase is expressed on the tissues lining the transgenic fish's mouth, then its mouth will light up as it eats the fish food. Similarly, if the fish transfected with the luciferase gene is translucent, then the digestive organs, particularly the stomach, will glow as the bioluminescence generating components come into contact and complete the bioluminescent reaction. The selected luciferase/luciferin systems should be one that is resistant to conditions, such as the acidic pH of the digestive system, in the fish.

Thus, for purposes herein, fish food that includes luciferin, preferably in lyophillized form, particularly, Renilla coelenterazine and Vargula luciferin, is provided. The transgenic fish that express luciferase or luciferin are also provided.

Also contemplated herein, are glowing fish lures for use as fish bait.

9. Plant food

Plant food, containing a luciferase or luciferin, for use with transgenic plants that express a luciferin or luciferase. For example, transgenic plants that express a luciferase are known [see, e.g., U.S. Pat. Nos. 5,464,758, 5,436,392, 5,432,081, 5,412,085, 5,362,865, 5,268,463, and 5,015, 580]. When treated with [i.e., fed] plant food containing a luciferase and other needed components of the bioluminescence generating system, these plants glow.

Plant food containing one or more components of the bioluminescence generating system, preferably a luciferin, is provided herein for administration to transgenic plants that express a luciferase. The plant food containing a luciferin and any necessary activators may be in the form of any composition that is typically applied to a plant to promote or maintain growth [e.g., see U.S. Pat. Nos. 4,016,880, 4,711,659, 4,804,403, 5,547,486, 5,553,853, RE 35,320, and RE 31,801]. The luciferin and any activators may be added directly to the plant food mixture or housed in a separate compartment and added to the plant food immediately prior to use. The plant food may be applied to the soil, sprayed on the foliage of the plant or any combination thereof.

F. Cartridges for loading or reloading the novelty items

In order to effectively charge, recharge or refill the bioluminescence generating systems that are part of the novelty items, a variety of cartridges are contemplated herein. It is to be appreciated that any charging device discussed herein is capable of either initially charging a novelty item, such as a squirt gun, or recharging such a novelty item once one or more component(s) of the bioluminescence generating system is depleted. Exemplary embodiments are set forth in FIGS. 28–34 and described in EXAMPLE 14 below.

EXAMPLES

The following examples are included for illustrative purposes only and are not intended to limit the scope of the invention.

Example 1
Dual Chamber Fluid Dispensing Apparatus—Toy Water Gun

An exemplary embodiment of the dual chamber fluid dispensing apparatus is a toy water gun as illustrated in FIGS. 1 through 3. The following description of that preferred embodiment is made with reference to those figures. The toy water gun includes two housings [or chambers] 10, 12 that conveniently may be constructed of injection-molded plastic or other suitable material. The two housings 10, 12 are affixed, such as glued, heat sealed or by other such means, along a median seam 46 to form the body of the water gun. See especially FIGS. 2 and 3.

In operation, one housing 10 contains a mixture having less than all the components necessary for generating bioluminescence and the other housing 12 contains a mixture having the remaining components or the remaining components, save the bioluminescent activator. Depression of the trigger 14 pushes the pistons 26, 36 into their respective cylinders 38, 48 compressing the trigger springs 28, 43 and pushing the contents of the cylinder through the second check-valve 34, into the mixing chamber 20 and out the nozzle orifice 22. As the trigger 14 is released, the trigger springs 28, 43 return to their relaxed state pushing the pistons 26, 36 out of the cylinders 38, 48 creating a vacuum therein which pulls the contents of the housings 10, 12 past the first check-valves 33, 32, respectively and into the cylinders 38, 48 respectively. Pumping the trigger, that is repeatedly depressing and releasing it, moves the mixtures contained in the housings through the gun and out the nozzle orifice 22.

As the mixtures leave the cylinders 38, 48, they enter the mixing chamber 20, via the conduit means 44 and second check-valve 34. Luminescence begins either upon mixing of the components or as the mixed composition contacts the air upon expulsion from the toy gun. The mixtures may be powdered, such as those produced by lyophilization, or they may be liquid. If powdered, water can be added prior to use.

The housings 10, 12 may be filled and refilled through the filling caps 17, 19, respectively, located at the top of each housing. A trigger 14 is attached to a trigger guide 13 which serves to guide the trigger 14 towards two piston assemblies 25. Depression of the trigger 14 activates the two piston assemblies 25. This causes a portion of the composition located in each housing 10, 12 to move through the water gun into a mixing chamber 20 and out a nozzle orifice 22. The preferred embodiment illustrated has a trigger guard 15 which helps prevent accidental discharge of the gun and makes the gun appear more realistic. The sighting aids 21, 23 aid in aiming the toy gun and also serve to make the gun appear realistic.

Only one of the two piston assemblies 25 is completely illustrated, and it is visible in FIG. 1. The other piston assembly is adjacent to and, in this preferred embodiment, identical to the one illustrated. These assemblies operate by substantially identical means and are activated by depression of the single trigger 14. The piston assembly 25 includes a piston 26 which passes through a sealing o-ring 30, is connected to a trigger spring 28 and moves within a cylinder 38. The piston assembly also includes a spring retainer 40 that secures one end of the trigger spring 28 to the end wall of the cylinder. The cylinder 38 is in communication with one end of a pick-up tube 18 and lies about perpendicular to the pick-up tube 18. The cylinder 38 also communicates with the mixing chamber 20 via conduit means 44.

In the sectional views of the water gun, illustrated in FIGS. 2 and 3, portions of the second, adjacent piston assembly are visible. Namely, the second trigger spring retainer 42 and trigger spring 43 are visible in FIG. 2, and the second piston 36 is visible in FIG. 3.

Referring to the piston assembly 25 illustrated in FIG. 1, the piston 26 passes into the water gun through the sealing o-ring 30 and into the cylinder 38. The trigger spring 28 is attached by one end to the piston and by its other end to the spring retainer 40 located at the opposite end of the cylinder from the piston. As the trigger 14 is depressed, the piston 26 moves into the cylinder 38 and through the sealing o-ring 30. This compresses the trigger spring 28 within the cylinder 38. As the trigger 14 is released, the trigger spring 28 expands, returning it and the piston 26 to a resting position.

Because the piston 26 is sealed within the cylinder 38 by the sealing o-ring 30, its repeated movement causes the air within the cylinder to be displaced thereby creating a vacuum within the pick-up tube 18 of the water gun. The composition located in the housing 12 is then drawn into the pick-up tube 18, past a first check valve 32, past the trigger spring 28, past a second check valve 34, into the mixing chamber 20 and out the nozzle orifice 22 via an outlet tube 24. The second check valve 34 is illustrated with a spring mechanism 35 which serves to maintain the check valve 34 in a closed position isolating the piston assembly cylinders 28 and conduit means 44 from the mixing chamber 20, allowing a vacuum to form within the gun during operation.

The same mechanism operates to simultaneously withdraw composition from the complementary housing 10 into the mixing chamber 20 via a pick-up tube 16. Thus, referring to FIGS. 2 and 3, the action of the piston 36 within its cylinder compresses the trigger spring 43 against the spring retainer 42 creating a vacuum within the pick-up tube 16 and moving some of the composition located in the housing 10 through the pick-up tube 16 into the mixing chamber 20 and out the nozzle orifice 22.

As illustrated in FIG. 2, the two pick-up tubes 16 and 18 originate in the housings 10 and 12, respectively. Each pick-up tube 16, 18 includes a check valve 32 and 33, respectively. The first check valves 32, 33 serve to prevent fluid flow from the piston assembly cylinders 38, 48 back into the housings 10, 12. The single second check valve 34 prevents the mixed compositions from flowing out of the mixing chamber 20 back into the piston assembly cylinders 38, 48.

Thus, repeated depression of the trigger 14 increases the pressure within the gun, thereby filling the mixing chamber 20 with a combination of the compositions located in the two housings 10, 12, then forcing the mixed compositions through the outlet-tube 24 and out the nozzle orifice 22.

Example 2
Dual Chamber Fluid Dispensing Apparatus—Gas-Charged Toy Water Gun

In contrast to the above-described toy water gun, the gas-charged toy water gun operates using pressurized gas, rather than the piston assembly, to move the bioluminescent mixtures through the system. A preferred embodiment of this device is illustrated in FIGS. 4 and 5. In this embodiment the butt of the water gun 86 houses the two chambers 64, 74 that contain the bioluminescence generating system components. Further, the butt 86 is detachable and thus readily replaced.

To pressurize the gun for operation, a $CO_2$ or air [or other suitable gas or mixtures thereof] canister 50 is inserted into a gas chamber 56 as shown. A screw cap 52, located at the base of the gas chamber, secures the canister 50 into the chamber 56. As the screw cap 52 is tightened, the $CO_2$ or air canister is forced against a piercing pin 54, thereby releasing $CO_2$ or air into the gas chamber 56 and charging the water gun for use.

Depression of a trigger 58 aligns a gas cock 60 with each of two gas conduits 62 and 72 and the gas chamber 56. With the gas cock 60 so-aligned, $CO_2$ gas or air enters the gas conduits 62 and 72 and passes into the two chambers 64 and 74. The pressure of the gas forces some of each mixture out of the chambers 64, 74, via composition pick-up tubes 66, 76. The composition pick-up tubes 66, 76 are connected to outlet conduits 78 and 80 through which the mixtures pass into a mixing chamber 68, and are combined. The continued pressure of the $CO_2$ gas or air forces the combined mixture from the mixing chamber 68 and out a nozzle orifice 70.

The gas conduits 62, 72 and outlet conduits 78, 80 are housed within the main body of the water gun and extend beyond it in the region where the butt 86 of the gun is attached to the main body. The composition pick-up tubes 66, 76 are completely within the butt of the water gun 86. In order to obtain a leak-free assembly of the butt of the gun to the main body, the gas conduits 62, 72 and outlet conduits 78, 80 each pass through a leak seal 88 located within the butt of the gun 86. The leak seals 88 may be constructed of rubber or similar soft sealing material and should be covered, either with a removable cap or with a material susceptible to piercing, to prevent spillage of the compositions contained therein.

In attaching the butt of the gun 86 to the main body, the gas conduits 62, 72 and outlet conduits 78, 80 pass through the leak seals 88 forming a tight seal between the tubes and the butt of the gun. Also, as can be seen in FIG. 4, the delivery tubes 78, 80 set within the composition pick-up tubes 66, 76 at the point where they enter the butt of the gun. This permits fluid communication between the composition pick-up tubes 66, 76 and the outlet conduits 78, 80.

Additional features of the preferred embodiment, as illustrated in FIGS. 4 and 5 include retaining hooks or latches 90, 92 and 94 positioned on the main body of the water gun and used to secure the butt of the gun to the main body. Additionally, the two chambers 64 and 74 can be configured with filler caps 82 and 84, as illustrated, thereby allowing them to be refilled as an alternative to replacement.

It will be appreciated that the gas used to operate the gas-charged fluid dispensing apparatus described herein may be other than carbon dioxide. Any gas or mixture of gases, such as air or mixtures of $O_2$ and $CO_2$, that operates in the same manner may be used.

Example 3
Dual Chamber Fluid Dispensing Apparatus—Gas-Charged

Figure 7:
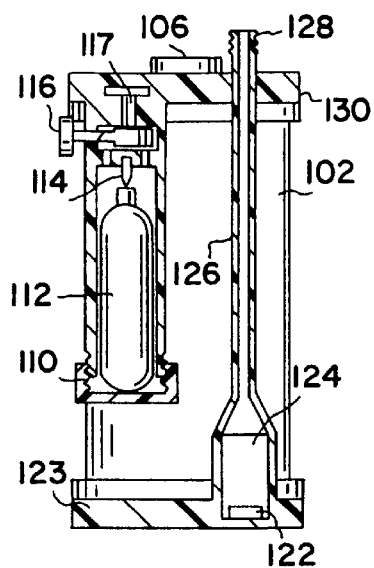
FIG. 7 is a sectional view taken on line 7—7 of FIG. 6.
Figure 8:
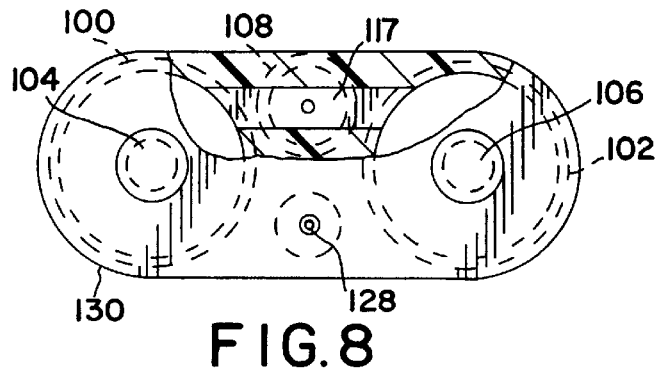
FIG. 8 is a top plan view of the structure of FIG. 6, partially cut away.

FIGS. 6, 7 and 8 illustrate a preferred embodiment of a gas-charged fluid dispensing apparatus as provided herein. This embodiment may be adapted for particular uses; for example, it may be housed within a decorative sculpture, thereby functioning as a decorative water fountain. Alternative embodiments incorporating this embodiment are illustrated in FIGS. 4 and 5 [EXAMPLE 2] and FIGS. 9 and 10 [EXAMPLE 4].

Referring to FIGS. 6 and 7, the gas-charged dual chamber dispensing apparatus has two chambers 100 and 102. In a preferred embodiment as illustrated, the two chambers 100 and 102 are refillable via filler caps 104 and 106 located on the upper end of the chambers. A gas chamber 108 is situated about equidistant from the two chambers and communicates with each of them via gas conduits 117. The gas conduits 117 end at gas inlets 118 that communicate with the two chambers 100, 102. The gas inlets 118 are positioned near the upper end of the chambers 100 and 102. While one gas inlet 118 is depicted, it is understood that each chamber 100, 102 has such an inlet.

A gas canister 112 fits into the gas chamber 108, being secured therein by a screw cap 110. Screwing the screw cap 110 tightly into place forces the top of the gas canister 112 against a piercing needle 114, thereby releasing gas into the gas chamber 108. A gas control valve 116 is used to control the flow of the gas from the gas chamber 108 into the gas conduits 118.

A mixing chamber 124 is also situated about equidistant from the two chambers 100 and 102 and communicates with them via outlet conduit means 122, such as fluid ports. The outlet conduits [fluid ports] 122 are located sufficiently near the bottom of the chambers 100 and 102 to permit the chamber contents to empty. Near the lower end of the two chambers 100, 102 are fluid outlets that connect to the fluid ports 122. Blow-out plugs 120 prevent the compositions contained therein from leaving the chambers and entering the fluid ports before activation of the device. One-way valves or similar devices can be substituted for the blow-out plugs 120. The mixing chamber 124, having bottom inlets and a top outlet, is associated with a nozzle 126, which may be attached or integral to the mixing chamber. Optionally, the nozzle 126 has a closure cap 132 distal to the mixing chamber 124.

In a preferred embodiment, illustrated in FIGS. 6, 7 and 8, an upper support 130 is shown. This upper support 130 spans the upper ends of both chambers 100 and 102 and over the top end of the gas chamber 108. The gas conduits 118 and inlets 117 are within the upper support 130. The nozzle 126 passes through the upper support 130 and is supported thereby.

Also illustrated in this preferred embodiment, is a base support 123 that spans across the lower ends of the chambers 100 and 102 and that is integral to the mixing chamber 124. The fluid ports 122 connecting the chambers 100 and 102 with the mixing chamber 124 are contained within the base support 123 [see, FIGS. 6 and 7].

To operate the basic dual chamber gas-charged fluid dispensing apparatus, a gas canister 112 containing gas under pressure, for example pressurized $CO_2$, is inserted into the gas chamber 108. The screw cap 110 is tightened, forcing the gas canister against the piercing needle 114. As gas escapes from the canister, it fills the gas chamber. The gas control valve 116 is opened, permitting the gas to enter the gas conduits 117 and pass into the chambers 100 and 102 through the gas inlets 118.

The pressure of the gas in the chambers pushes the mixtures therein against the blow-out plugs 120, or through the one-way valves, out the fluid outlets, into the fluid ports 122 or other fluid conduit means, and into the mixing chamber 124 via the bottom inlets. In the mixing chamber 124, the mixtures combine, while the continued pressure from the gas propels the combined mixtures through the nozzle 126 and out the nozzle orifice 128.

Figure 10:
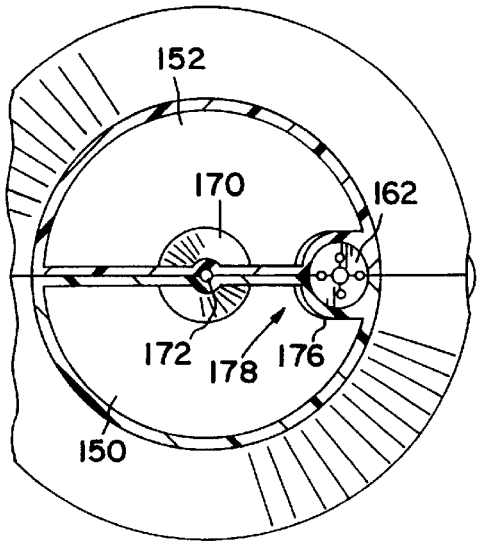
FIG. 10 is a sectional view taken on line 10—10 of FIG. 9.
Figure 9:
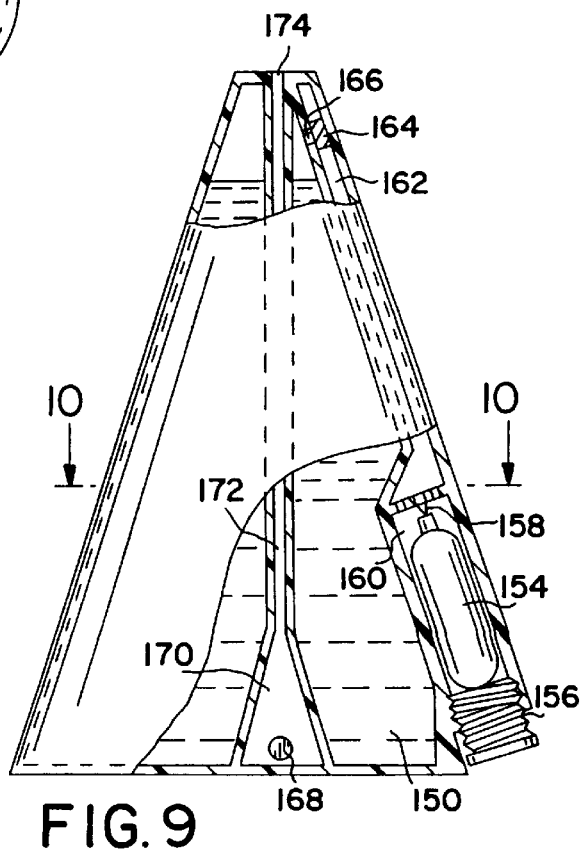
FIG. 9 is a side elevation view of a fountain type configuration of the gas-charged dual chamber fluid dispensing apparatus, with portions cut away.

Example 4
Dual Chamber Fluid Dispensing Apparatus and Volcano-Shaped Gas-Charged Apparatus FIGS. 9 and 10 illustrate a preferred embodiment of the gas-charged fluid dispensing apparatus illustrated in FIGS. 6, 7 and 8 and described above. In this embodiment, each chamber has a generally half-conical shape, or other suitable shape [depending upon the intended use], such that, when attached they form, in this embodiment, a volcano-shaped apparatus. The gas chamber 160 and gas conduit 162 are defined by the inner walls 176, 178 of the chambers 150, 152, respectively. Similarly, the mixing chamber 170 and nozzle 172 are defined by the inner walls 176, 178 of the chambers 150, 152, respectively.

As in the apparatus, FIGS. 6, 7 and 8, a gas canister 154 is housed in the gas chamber 160 and is activated by tightening a gas screw-cap 156 which forces the gas canister 154 against a piercing needle 158 thereby releasing the gas into the gas chamber 160. The gas enters the gas conduits 162, forces out the blow-out plugs 164 and passes into the chambers 150, 152 via the gas inlets 166. Alternatively, a control valve, or other suitable control means, is situated between the gas chamber and gas conduits or within the gas conduit means and used to control the flow of gas into the gas chambers.

Within the two chambers 150, 152, one containing, for example, up to all except one component necessary for the bioluminescence generating reaction and the other the remaining component(s), the gas forces the bioluminescence generating mixtures into the mixing chamber 170. Blow-out plugs 168, situated between the chambers 150, 152 and mixing chamber 170, prevent the bioluminescence mixtures from entering the mixing chamber 170 until the apparatus is activated. The continued pressure of the gas forces the combined mixtures from the mixing chamber 170 through the nozzle 172 and out the nozzle orifice 174.

This apparatus is particularly designed for use as "fireworks" configured in the shape of a volcano. As the combined bioluminescent mixtures are forced from the apparatus into the air, they glow in a similar manner to traditional fireworks.

Alternatives to the specific embodiment described herein are likewise contemplated. For example, blow-out plugs may be replaced by one-way or control valves. Manually operated valves may be replaced by electronically or mechanically controlled valves. The apparatus does not have to be in the shape of a volcano, but may be formed into any shape, such as animals, humans, plants or abstract forms.

In another alternative embodiment, not illustrated, the nozzle 172, through which the mixed bioluminescent composition exits from the apparatus, is shortened, moving the mixing chamber 170 closer to the nozzle orifice 174. This is particularly appropriate where the bioluminescence generating system used in the apparatus produces short bursts of light or is quickly exhausted once activated, such that the bioluminescent components are preferably kept separated until just before expulsion from the apparatus. In such an alternative embodiment, outlet tubes (or conduits) may be provided that maintain the bioluminescence generating components separate until just before expulsion from the apparatus. The outlet tubes illustrated in FIGS. 23, 24 and 26 and described in EXAMPLE 11, could likewise be employed in this alternative embodiment.

Example 5
Compressible Dispensing Apparatus—Lotion/Cream container

Figure 11:
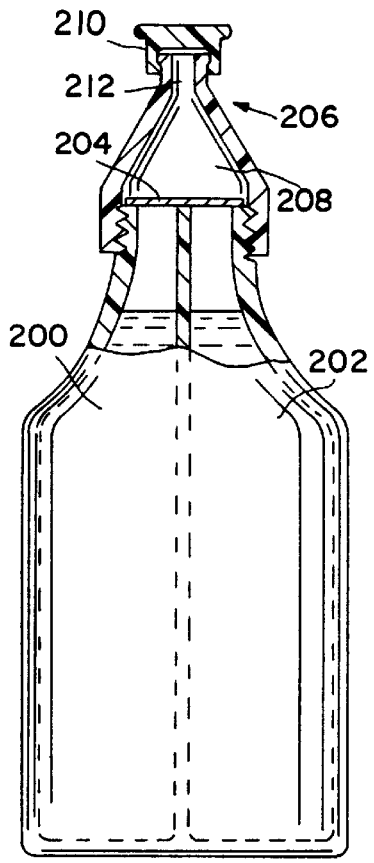
FIG. 11 is a side elevation view, partially cut away, of a dual chamber compressible dispensing container.

FIG. 11 illustrates a preferred embodiment of a compressible dispensing apparatus particularly useful for dispensing waxy, pasty or semi-solid compositions such as body lotions or finger paints. In this embodiment, the container, preferably a tube, has two chambers 200, 202. In certain embodiments, within one chamber are all, except for one or more, components of the bioluminescence generating system, and in the other chamber are the remaining components. The composition, such as body lotion or cream is in one or, preferably, both chambers. The container is preferably constructed of a pliable collapsible or compressible material, such as plastic, plastic/metal laminate or similar collapsible composite, which can be squeezed by hand. Numerous such tubes are known to those of skill in this art are used to dispense products such as finger paints, toothpaste, gels, lotions and other such items.

A membrane seal 204 at the top end [dispensing end] of the container prevents the contents of the chambers from mixing. The cap apparatus 206 of the container has a dispensing cap at the top 210 and is configured such that a space 208 exists between the membrane seal 204 and the dispensing cap 210, which space acts as a mixing chamber 208.

Thus, to operate the lotion/cream container, the membrane seal 204 is punctured, or otherwise opened, and a portion of the contents of the two chambers 200, 202 are simultaneously squeezed into the mixing chamber 208 by applying pressure to the container. The dispensing cap 210 is removed and the contents of the mixing chamber 208 are squeezed out the dispensing orifice 212. The mixed composition may be dispensed by squeezing the container or by squeezing the cap apparatus 206. Alternatively, a plunger/syringe device [not illustrated] may be attached to the dispensing orifice and the mixed cream composition thereby withdrawn from the mixing chamber 208.

The membrane seal, 204 situated between the chambers 200, 202 and the mixing chamber 208, functions to prevent the contents of the mixing chamber 208 from returning into either of the chambers 200, 202. It may be constructed, for example, of a thin layer of rubber, plastic, or other suitable porous material, having a small hole or holes through which the contents pass. As the sides of the container are compressed, portions of the contents of the chambers are forced through the holes in the membrane and into the mixing chamber, with the membrane returning to its "sealed" state once the pressure is relieved. A one-way valve or similar device may be substituted for the membrane seal 204, provided it too prevents the contents of the mixing chamber 208 from flowing back into either of the chambers 200, 202.

Example 6
Bottle/Bladder Apparatus—Bubble Composition Bottle

Figure 13:
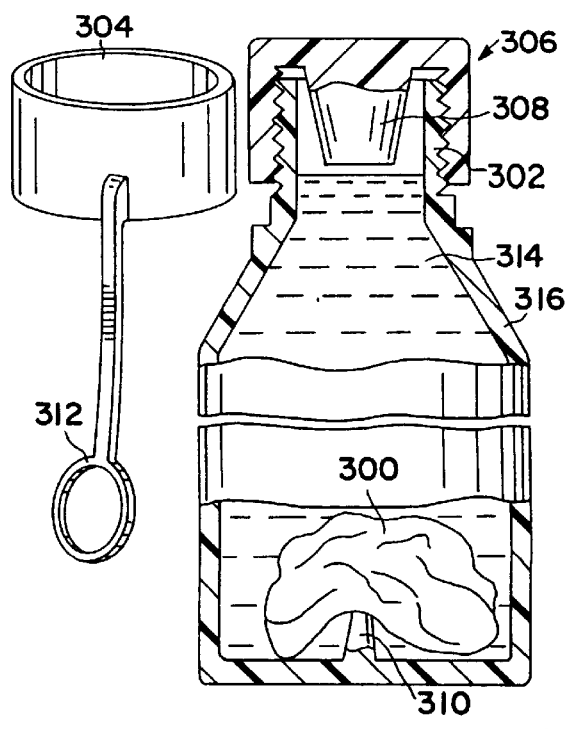
FIG. 13 is a view similar to FIG. 12, with the components mixed and the bubble blowing wand detached for use.

FIGS. 1 2 and 13 illustrate a preferred embodiment of the bottle/bladder apparatus adapted for use with bioluminescent bubble compositions. This bubble composition bottle has a bladder 300 positioned within it and held in place, in the neck 302 of the bottle, by friction. A collar 304 is positioned on the neck of the bottle 302, preventing the cap 306 from being screwed completely onto the top of the bottle. The cap 306 contains a plunger 308 which operates to push the bladder 300 into the body of the bottle when the collar 304 is removed and the cap 306 is screwed down tightly. Upon entering the body of the bottle, the bladder is pierced by a piercing pin 310 located on the bottom of the bottle; thereby releasing the contents of the bladder into the bottle. FIG. 13 shows the bottle with the collar 304 removed, the cap 306 screwed on tightly, and the bladder 300 collapsed within it.

Component(s) [less than all] of the bioluminescence generating reaction are contained in the bladder. The components may be in the form of a solution, suspension, suspended particles, or particles. Prior to use the bottle may be gently agitated. The particles may be time release capsules that release their contents upon exposure to the bubble composition or from which the contents diffuse upon mixing of the contents of the bladder with the bubble composition. The remaining component(s), such as $Ca^{2+}$ or ATP, are contained in the bubble composition 314, which is preferably a mild bubble forming composition. Selection of the bioluminescence generating composition depends upon the selected bubble composition and also the desired action. In other embodiments, remaining components, such as ATP, FMN, a flavin reductase or other component that may be somewhat sensitive to the bubble composition, of the bioluminescence generating system may be added to the bubble composition just prior to use.

Figure 12:
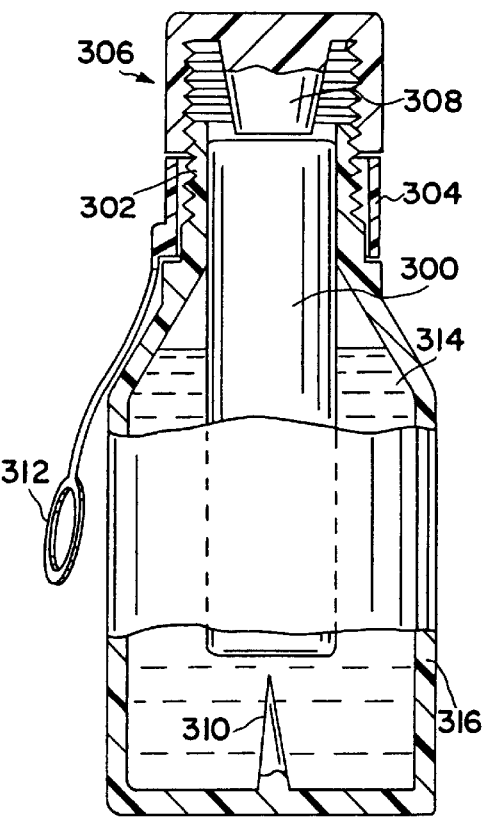
FIG. 12 is a side elevation view, partially cut away of a bottle/bladder apparatus designed for use with bubble-blowing compositions.

The collar 304 of the bottle is adapted with a bubble blowing ring 312, with arm, integral thereto. Thus, the collar 304 is removed, the bladder 300 pierced within the bottle as described and the bubble blowing ring 312 dipped into the mixed composition, withdrawn and bioluminescent bubbles blown. A standard bubble blowing wand [arm with ring] may be used and/or provided in place of that depicted in FIG. 12.

The bladder 300 should be constructed of a material that can be pierced by a piercing means, such as a needle or pin, made for example of thin plastic or other polymeric film. Preferably the distance from the base of the neck of the bottle to the tip of the piercing needle is less than the length of the bladder, so that the bladder will be pierced by the needle before its top edge clears the base of the neck of the bottle.

The bottle 316 may be fabricated of any material ordinarily used for dispensing bubbles. It may be transparent or translucent to the bioluminescent light so that any glow in the bottle can be seen.

Example 7
Container/Bladder Apparatus—Beverage Can

Figure 14:
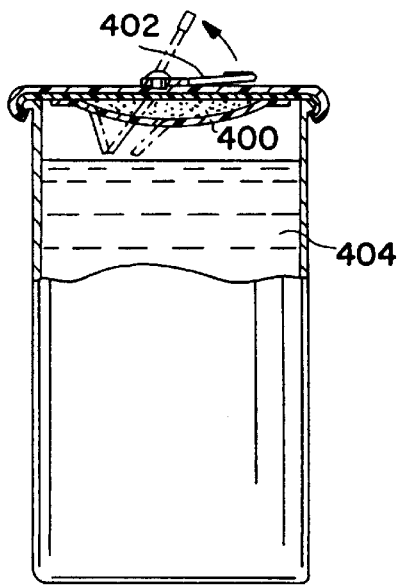
FIG. 14 is a side elevation view, partially cut away, of beverage container with a bladder apparatus actuated by opening of the beverage container.

An exemplary of the container/bladder apparatus, illustrated in FIG. 14, is suitable for use as a beverage can or bottle. It is configured similarly to a pop-top aluminum drink can but has a bladder 400 under the top which is pierced by the pop-top 402 when the can is opened. The bladder may be centered under the top of the can, as illustrated, may be off-center or may be attached to the top and side of the can. Positioning of the bladder is chosen such that it may be readily pierced and its contents mixed with the contents of the container 404. Thus, the bladder should be sufficiently thin that the pop-top 402 is able to pierce it allowing its contents to mix with the contents of the beverage can. The can is preferably fabricated of translucent or transparent material such that the glowing beverage can be observed.

An alternative embodiment includes a beverage container with two pop-tops, in which one is designed, such as including by having a point at the end, to puncture the bladder and the other can be a typical pop-top that is used for emptying the contents of the can, such as by pouring into a glass or into a person's mouth. Since the novelty of these items resides in the resulting glow in the beverage, the beverage should be poured into a glass, or the container should be transparent or translucent to the bioluminescent light.

Another alternative contemplated herein includes a mesh filter surrounding the bladder and functioning to prevent small pieces of the ruptured bladder from mixing with the contents of the can. The contents of the bladder are in aqueous composition; thus, the density of the mesh of the filter that is permeable to the luciferase and other bioluminescence generating components.

Similarly, embodiments employing other opening types are contemplated herein. For example, the bladder and corresponding container opening may be pierced with a point-ended straw, or other sharp device. Likewise, the dispensing opening [which may be the same as the bladder-associated opening] may be covered with a thin aluminum pull tab. Critical to the operation of the can/bladder combination is that the bladder preclude mixing of the contents of the bladder and the can until the consumer takes action to rupture the bladder.

The bladder may be constructed of any material which is amenable to being pierced as described and is preferably constructed of a material which will rarely if ever break into small pieces when pierced. For example, aluminum foil with a thin plastic coating, when pierced with a point-ended straw in particular, will rarely break into small pieces. The body of the can may be constructed of aluminum, plastic or similar material and is preferably constructed of a translucent material such as plastic.

The bladder includes up to all except for one component of the bioluminescence generating system, and the beverage includes the remaining component(s). For example, the bladder includes the aequorin photoprotein [typically 0.1 to 1 mg or more] in a composition containing a chelator to prevent activation of the photoprotein, and the beverage contains $Ca^{2+}$.

Example 8
Single Use, Dual Chamber Fluid Packaging Apparatus

Figure 15:
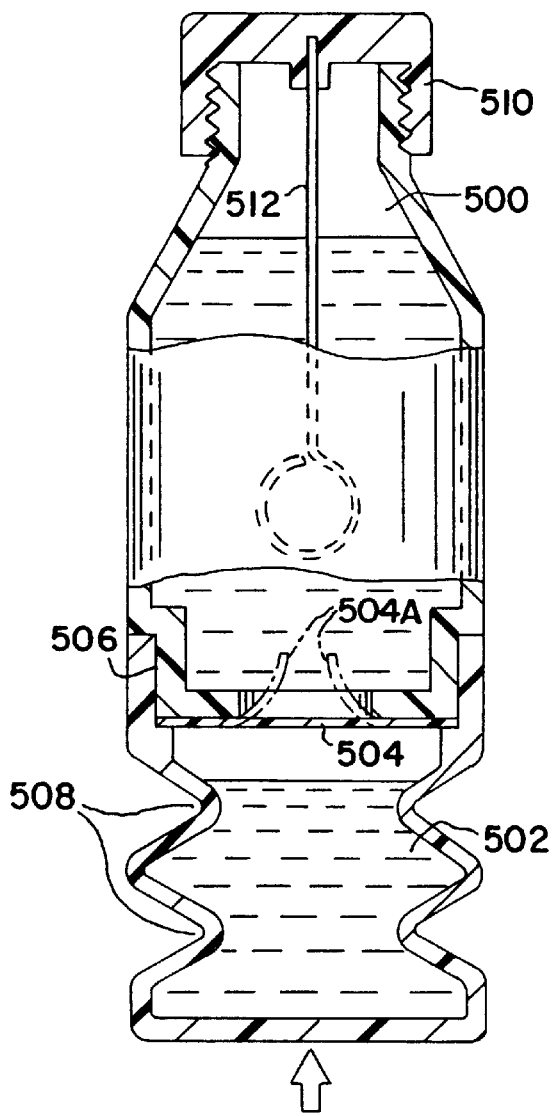
FIG. 15 is a side elevation view, partially cut away, of a single use, dual chamber fluid packaging apparatus adapted for use with bubble-blowing compositions.

FIG. 15 illustrates an exemplary embodiment of the single use, dual chamber fluid packaging apparatus or bottle described generally above, and the following description is with reference to that FIGURE. The bottle has a first chamber 500 which contains a composition including one or more, up to all but one, of the bioluminescence generating system components. Below the first chamber and operatively attached thereto, is a second chamber 502, containing the remaining bioluminescence generating system components in composition. In the embodiment illustrated, the first chamber 500 is seated in the second chamber 502 along a side seam 506 and a separation membrane 504.

The second chamber 502 is constructed of pliable material, such as plastic, that is convoluted 508 such that it can be readily collapsed against the bottom of the first chamber in the direction of the illustrated arrow. When collapsed in this way, the force of the composition contained within the second chamber ruptures the separation membrane 504A, permitting the compositions to mix. Once mixed, the compositions begin to illuminate.

This apparatus, as illustrated, is adapted for use with bubble-blowing compositions in that the cap of the bottle 510 has a bubble-blowing wand 512 attached to it. Alternatively, the apparatus may be used with a beverage and, if so used, would not have the illustrated bubble-blowing wand 512.

Another embodiment of this apparatus, not illustrated, but contemplated herein, is a bottle in which the second chamber may be secured to the first chamber or to itself in a collapsed position. For example, the second chamber can be adapted with a hooking mechanism on its exterior such that it can be hooked to itself when collapsed.

Example 9
Cap Apparatus for Use with Composition Vessels

FIGS. 16, 17 and 18 & 19 illustrate three exemplary embodiments of the cap apparatus for use with composition vessels.

A. Cork Cap Apparatus

Figure 16:
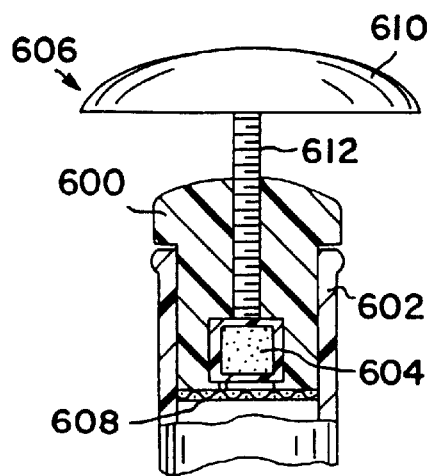
FIG. 16 is a side elevation view, partially cut away, of a cap apparatus operated by depression of the plunger assembly to rupture the capsule contained within the cork cap.

Referring to FIG. 16, a cork 600, situated within the neck 602 of a bottle and having a rupturable capsule 604 housed within it, is illustrated. In this embodiment, the bottom edge of the cork 600 is substantially U-shaped such that a pocket is formed. Contained within the pocket is the capsule which is in communication with the screen 608 which is permanently attached to the bottom of the cork. The capsule contains one or more, up to all but one, of the bioluminescence generating system components. A plunger assembly 606 is positioned, partially within the cork, such that depression of the plunger assembly 606 results in rupture of the capsule and release of its contents into the composition within the bottle. The screen 608 or other filtering device prevents fragments of the ruptured capsule from entering the vessel.

The plunger assembly 606, illustrated in FIG. 16, has a top portion 610 integral to the stem portion 612. Pressing on the top portion 610 forces the stem 612 to move within the cork 600 and against the capsule 604, thereby rupturing the capsule and releasing its contents into the vessel.

Figure 17:
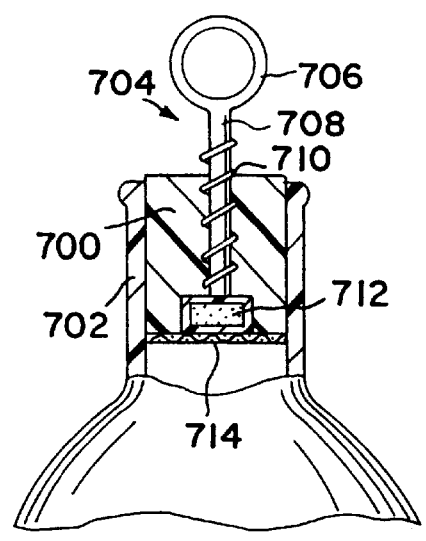
FIG. 17 is a side elevation view, partially cut away, of a cap apparatus operated by screwing the plunger assembly into the cork cap to rupture the capsule contained therein.

FIG. 17 illustrates an alternative embodiment of the cork cap apparatus. In this embodiment, the cork 700 is illustrated as being about flush with the top of the neck 702 of the bottle. The plunger apparatus 704 is adapted with a finger ring 706 for ease in handling. The stem 708, which may be pointed or blunt or any combination thereof, is threaded 710. In operation, the plunger assembly 704 is screwed into the cork 700 where it contacts a capsule 712, rupturing it and releasing its contents against the screen 714 or filter. The capsule will preferably contain powdered or otherwise condensed bioluminescence generating components.

It will be appreciated that the cork cap alone, with encapsulated compositions encased within and screen or filter attached thereto, is an alternative embodiment of the two illustrated cork cap apparatus. In this embodiment a corkscrew may be employed to rupture the capsule and to remove the cork cap.

B. Screw-top Cap Apparatus

Figure 18:
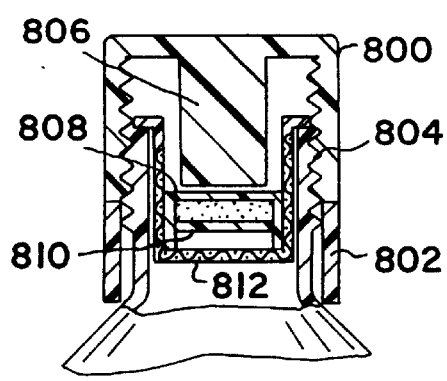
FIG. 18 is a side elevation view, partially cut away, of a cap apparatus operated by screwing the screw-cap onto the top of the bottle forcing the plunger assembly against the capsule contained within the neck of the bottle, thereby rupturing the capsule membranes.
Figure 19:
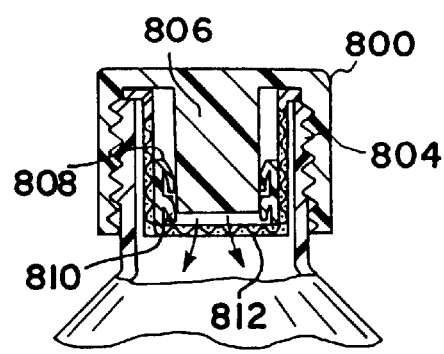
FIG. 19 is a view similar to the view of FIG. 18, with the cap apparatus tightly secured against the top of the bottle and the capsule membranes ruptured.

FIGS. 18 and 19 illustrate another exemplary embodiment of the cap apparatus for use with composition vessels. FIG. 18 shows the cap apparatus before activation or engagement. This is particularly adapted for use with a wine or champagne bottle, and includes encapsulated bioluminescence generating system components.

This embodiment generally includes a bottle-shaped vessel with a collar 802 situated about the neck 804 of the bottle and a cap 800 attached to the top of the bottle just above the collar 802. The neck of the bottle 804 is threaded to receive the screw-on cap 800. The collar 802 is situated such that a lower portion of the threads on the neck of the bottle 804 are covered thereby preventing the screw-on cap 800 from being completely attached to the bottle. Enough threads remain exposed on the top of the bottle such that the screw-on cap 800 is securely, though not completely, attached to the top of the bottle.

The screw-on cap 800 has a plunger 806 integral thereto which extends into the bottle neck 804. A screen or filter assembly 812 is attached to the interior of the bottle within the bottle neck 804. A membrane system 808, 810 or capsule or similar composition packaging is situated between the plunger 806 of the screw-on cap 800 and the screen/filter assembly 812. In operation, the collar 802 is removed, for example by removing the screw-cap 800 and lifting off or screwing off the collar 802 or by tearing off the collar 802, and the screw-on cap 800 is tightened against the top of the bottle. This forces the plunger 806 through the membranes 808, 810, rupturing them and releasing the compositions contained therein. The composition(s) pass through the screen assembly 812 and are mixed with the contents of the bottle. FIG. 19 illustrates the cap apparatus fully engaged with the membrane system ruptured.

In the embodiment illustrated, the screen assembly 812 is attached along the interior of the neck of the bottle 804 as well as across the interior of the neck, thereby forming a basket within which the membrane system 808, 810 sits. Alternatively, the screen assembly can be attached around the circumference of the bottle neck only and not along its sides to the top of the bottle, as illustrated.

The precise height of the collar 802 will be determined by the length of the plunger 806 and location of the membrane system 808, 810. The height will be sufficient to prevent the plunger 806 from being engaged through the membrane system 808, 810 prior to activation by the user, while permitting the screw-on cap 800 to be secured to the top of the bottle.

The membrane system 808, 812 contains one or more, up to all but one, of the bioluminescence generating system components. Typically the components will include the luciferase and luciferin in lyophilized form.

The illustrated embodiment is shown and described as attached to a bottle. It will be appreciated, however, that the vessel to which the cap apparatus is attached may be a can, tube or any other container. Additionally, the embodiment is exemplified and illustrated with reference to the neck of the bottle. It is not necessary that the vessel have a "neck" for the cap apparatus to function. For example, if the vessel does not have a neck, other means may be employed to hold the collar in place below the screw-on cap, such as, a lip formed on the container, below the threads, to stop the collar at an appropriate point.

With respect to these three embodiments of the cap apparatus adapted for use with composition vessels, the stem of the plunger assembly is short enough not to pierce the screen or filter device, yet long enough to effectively rupture the capsule, membrane or other packaging once engaged. The bioluminescence generating system component(s) contained within the cap apparatus may be powdered or in composition or in any form amenable to addition to the composition contained within the vessel. Additionally, the components may be contained in more than one capsule, membrane or other packaging. In this case, the component packages are adjacently positioned, such that each is ruptured by engagement of the plunger. Preferably, the remain-

Example 10
Spray container apparatus

FIGS. 20, 21 and 22 illustrate an exemplary embodiment of a spray container provided herein. This container is typically a can apparatus intended for use in combination with the bioluminescence generating systems as described herein. The following description of that exemplary embodiment is made with reference to those figures.

The spray container apparatus includes two portions, a top housing portion 902 and a bottom plunger portion 904. The contents of the top housing portion 902 include all, except one or more, of the components of a bioluminescence generating system. The top housing portion 902 also contains a conduit 912 operatively attached to a spray nozzle 920.

The top housing portion 902 of the spray container apparatus is adapted to receive the bottom plunger portion 904. In this embodiment, the top housing portion 902 and bottom plunger portion are threaded 903 and 910, respectively, such that the bottom plunger portion 904 can be screwed onto the top housing portion 902. [See FIG. 21, illustrating the spray container apparatus with the bottom plunger portion fully screwed into place.]

The top housing portion 902 additionally has a pocket 926 defined by a conical side wall 922 and a top wall/rupture membrane 916. The pocket 926 is adapted to receive a pellet 906, that contains the remaining component(s) necessary for generating bioluminescence.

The bottom plunger portion 904 of the spray container apparatus has a plunger 914 shaped and situated such that it fits into the pocket 926 of the top housing portion 902 when the bottom plunger portion 904 is screwed tightly in place. The bottom plunger portion 904 is adapted with an angular seal 918 that serves to seal the bottom plunger portion 904 against the top housing portion 902 thereby preventing leakage of the contents of the spray container apparatus.

In operation, the pellet 906 is placed into the pocket 926 of the top housing portion 902 where it contacts the top wall/rupture membrane 916 of the pocket 926. The bottom plunger portion 904 is then screwed onto the top housing portion 902, thereby forcing the plunger 914 against the pellet 906, which presses against the top wall/rupture membrane 916 of the pocket 926, rupturing the same. The pellet dissolves or is suspended in the composition contained in the top housing portion 902 and the composition glows. Depression of the spray nozzle 920 releases the contents of the spray container apparatus.

Alternative embodiments of this spray container apparatus will be appreciated. For example, the pellet 906 may be a vessel containing the necessary bioluminescence generating components that is fabricated from material that can dissolve or that will be suspended in the composition contained in the top housing portion 902 of the spray container apparatus 900 or that will release its contents upon contacting the composition, such as by passive diffusion. Examples of such material include, but are not limited to liposomes, gelatin, soluble paper and other such materials that will dissolve or release contents into aqueous compositions. Further, the spray container apparatus 900 can be adapted such that the bottom plunger portion 904 snaps onto the top housing portion 902, rather than screwing into place.

ing components required for completion of the bioluminescent reaction are contained within the vessel within any composition. These embodiments are particularly adapted to use with wine or champagne or other beverage.

Example 11
Alternative Embodiment of Dual Chamber Fluid Dispensing Apparatus—Toy Water Gun Another embodiment of the dual chamber fluid dispensing apparatus is a toy water gun, such as that illustrated in FIGS. 23 through 26. This toy water gun includes two housings [or chambers] 406, 408 that may be constructed of injection-molded plastic or other suitable material. The two housings 406, 408 are affixed, such as glued, heat sealed or by other such means, along a median seam 462 to form the body of the water gun. See especially FIGS. 25 and 26.

In operation, one housing 406 contains a mixture having less than all the components necessary for generating bioluminescence and the other housing 408 contains a mixture having the remaining components or the remaining components except for air. Depressing the trigger 410 pushes the pistons 428, 430 into their respective cylinders 450, 452 compressing the trigger springs 432, 434 and pushing the contents of the cylinder through the respective conduit means 458, 460, past the second check-valves 442, 444, out the outlet tubes 424, 426, into the mixing chamber 420 and out the nozzle orifice 422. As the trigger 410 is released, the trigger springs 434, 432 return to their relaxed state pushing the pistons 430, 428 out of the cylinders 452, 450 creating a vacuum therein that pulls the contents of the housings 406, 408 through the pick-up tubes 412, 414, past the first check-valves 438, 440 and into the cylinders 450, 452. Pumping the trigger, such as by repeatedly depressing and releasing it, moves the mixtures contained in the housings through the gun into the mixing chamber 420 and out the nozzle orifice 422.

As the mixtures leave the outlet tubes 424, 426, just prior to expulsion from the toy gun via the nozzle orifice 422, they enter the mixing chamber 420. Bioluminescence begins either upon mixing of the components or as the mixed composition contacts the air as it exits the toy gun. The mixtures may be powdered, such as those produced by lyophilization, or they may be condensed into a paste, or they may be liquid. If powdered or condensed, water or a suitable composition, such as a suitable buffer can be added prior to use.

The housings 406, 408 may be filled and refilled through the filling caps 464, 466 located at the top of each housing. The trigger 410 is attached to a trigger guide 416 which serves to guide the trigger 410 towards the two piston assemblies 472. Only one of the two piston assemblies 472 is completely illustrated, and it is visible in FIG. 23. The other piston assembly is adjacent to and, in this embodiment, identical to the one illustrated. Depression of the trigger 410 activates the two piston assemblies, e.g., 472. This causes a portion of the composition located in each housing 406, 408 to move through the toy gun into a mixing chamber 420 and out a nozzle orifice 422, as detailed above.

The piston assemblies e.g., 472 each include a piston 430, 428 which passes through a sealing o-ring 436, 429 is connected to a trigger spring 434, 432 and moves within a cylinder 452, 450. The piston assemblies each also include a spring retainer 456, 454 that secures one end of the trigger spring 434, 432 to the end wall of the cylinder. Each cylinder 452, 450 is in communication with one end of a pick-up tube 414, 412 and is about perpendicular to the pick-up tubes 414, 412. Each cylinder 452, 450 also communicates with the conduit means 458, 460.

Because the pistons 428, 430 are sealed within their cylinders 450, 452 by a sealing o-ring 429, 436, repeated movement of the pistons within the cylinders causes the air within the cylinders to be displaced thereby creating a vacuum within the pick-up tubes 412, 414 of the toy gun. This initiates the operation of the toy gun as described in detail above.

The illustrated embodiment has a trigger guard 411 that acts to prevent accidental discharge of the gun and makes the gun appear more realistic. The sighting aids 468, 470 aid in aiming the toy gun and also serve to make the gun appear realistic.

As illustrated in FIG. 25, the two pick-up tubes 412 and 414 originate in the housings 406 and 408, respectively. Each pick-up tube 412, 414 includes a check-valve 440, 438, respectively. The first check-valves 440, 438 serve to prevent fluid flow from the piston assembly cylinders 450, 452 back into the housings 406, 408. The second check-valves 442, 444, similarly prevent the fluids from flowing out of the outlet tubes 424, 426 and back into the piston assembly cylinders 452, 450.

Thus, in operation, repeated depression of the trigger 410 increases the pressure within the gun, thereby filling the mixing chamber 420 with a combination of the compositions located in the two housings 406, 408, then forcing the mixed compositions out of the toy gun through the nozzle orifice 422.

Example 12

Compressible Dispensing Apparatus

FIG. 27 illustrates an alternative exemplary embodiment of a compressible dispensing apparatus. This embodiment is particularly adapted for containing and dispensing bioluminescent slimy play material as described herein, but may be used to dispense other ingredients. The primary difference between the embodiment illustrated in FIG. 11 and that illustrated in FIG. 27 is that the latter has one or more small compartments 942, 944 located within the apparatus. These compartments are located such that compression of the apparatus expels the contents of the compartments into the main body 940 of the apparatus where those contents and any contents contained within the main body 940 mix.

The embodiment illustrated in FIG. 27 has a first compartment 942 and a second compartment 944 contained within the main body 940 of the compressible dispensing apparatus. The compartments 942, 944 are preferably formed, along at least one edge 950, 952, by rupturable membranes, such as plastic membranes, or other readily punctured dividing means. At least one other edge of each compartment 946, 948 is permanently affixed to the interior of the main body 940 of the apparatus. Thus, upon compression of the apparatus, the contents of the two compartments 942, 944 press against and rupture the rupturable membranes 950, 952, resulting in expulsion of the contents of the two compartments 942, 944 into the main body 940 of the apparatus. Because at least one edge of each compartment 946, 948 is permanently affixed to the interior of the apparatus, the compartments remain in position and readily rupture during compression.

Preferably the two compartments 942, 944 are large enough to contact one another along one contact edge 954 within the apparatus. As the sides of the apparatus are compressed, the contents of the two compartments are pressed against this contact edge 954 and against the rupturable membranes 950, 952, which membranes then rupture. Preferably, the cap 956 to the apparatus remains in place until the two compartments have been ruptured and the contents mixed within the apparatus.

The compressible dispensing apparatus is illustrated in FIG. 27 with two compartments 942, 944; however, it will be appreciated that one, three or more compartments may be included as appropriate. Factors to be considered in determining the appropriate number of compartments are the bioluminescence generating system to be used, the ingredients, particularly slimy play material ingredients to be used, the desired timing and duration of illumination, and the ultimate use for resulting composition, such as the slimy play material.

By way-of example only, where two compartments are included in the apparatus, as illustrated in FIG. 27, one compartment may contain the charged luciferin/luciferase mixture, such as aequorin photoprotein with coelenterazine and oxygen and the second compartment may contain a polyvinyl alcohol mixture. The main body of the apparatus contains the remaining ingredients, such calcium ions, necessary to complete the bioluminescence generating reaction, and also contains the other ingredients of the slimy play material, such as sodium tetraborate.

Alternatively, where the apparatus is configured with three compartments within the main body, one or more of the ingredients contained within the main body of the two compartment embodiment may instead be contained within the third compartment. For example, the sodium tetraborate may be included in the third compartment and the calcium ions, in an aqueous medium, may be in the main body of the apparatus. It will further be appreciated that the contents of each compartment and/or the main body may be in powder, liquid or semi-solid form. The liquid or semi-solid form are preferred.

Example 13

Recombinant production *Renilla reniformis* luciferase

The phagemid pTZ18R (Pharmacia) is a multi-purpose DNA vector designed for in vitro transcriptions and useful for expression of recombinant proteins in bacterial hosts. The vector contains the β-lactamase gene, which allows for the selection of transformants by resistance to ampicillin, and a polylinker site adjacent to the lacZ' gene. The heterologous gene of interest is inserted in the polylinker and transcribed from the lac promoter by induction, for example, with isopropyl-β-D-thiogalactopyranoside (IPTG).

The DNA encoding the *Renilla reniformis* luciferase has been cloned (e.g., see U.S. Pat. Nos. 5,292,658 and 5,418,155). The plasmid pTZRLuc-1 encodes the Renilla luciferase on a 2.2 Kbp EcoRI to SstI DNA fragment inserted in EcoRI and SstI sites of pTZ18R (plasmid construction is described U.S. Pat. Nos. 5,292,658 and 5,418,155; see also Lorenz et al. (1991) *Isolation and Expression of a cDNA encoding Renilla reniformis Luciferase, Proc. Nati. Acad. Sci. U.S.A.* 88:4438–4442). The initiation of transcription of the Renilla luciferase cDNA is under the control of the lacZ' promoter. *E. coli* strains harboring plasmid pTZRLuc-1 express Renilla luciferase that is functional in bioluminescence assays and retains the most of the critical properties of the native enzyme (see, e.g., U.S. Pat. Nos. 5,292,658 and 5,418,155).

A derivative of pTZRLuc-1, pTZRLuc-3.6, produces approximately 7-fold higher levels of recombinant Renilla luciferase than pTZRLuc-1 when transformed into the same *E. coli* host. Competent *E. coli* strain XL-1 was transformed using purified pTZRLuc-3.6 according to the instructions provided by the manufacturer (XL-1 Supercompetent cells™ and protocol; Stratagene, Inc., La Jolla, Calif.). Transfectants were selected by plating on Luria Broth (LB) plates supplemented with 100 μg/ml ampicillin.

Single ampicillin resistant colonies were grown in LB medium supplemented with 100 μg/ml ampicillin at ambient temperature using continuous shaking until cell growth reached mid-log phase (i.e., cell culture reaches an O.D.$_{600nm}$=0.6–0.8 units). Transcription from the lac promoter was induced by addition of 1 mM IPTG and cell culture was shaken at ambient temperature for an additional 8 hours.

Cells were harvested by centrifugation at 10,000 x g and frozen at −20° C. The cell pellet was thawed and resuspended at a 1:5 ratio (w/w) in a compositions containing 10 mM EDTA, pH 8.0, containing 4 mg/ml lysozyme (Sigma Chemical Corp.). The cells were placed in a 25° C. water bath for 30 minutes and then transferred to ice for 1 hour. The cells were lysed by sonication at 0° C. using a 1 minute pulse from an Ultrasonics, Inc. cell disruptor.

The lysed cellular debris was removed by centrifugation at 30,000 x g for 3 hours and the supernatant was decanted and retained. The pellet was resuspended at a 1:5 ratio in the above-described compositions, and the subsequent incubations, lysis and centrifugation steps were repeated. The two supernatants were combined and stored at −70° C.

The resulting "clarified lysate" was employed as a source of recombinant luciferase. Alternatively, the lysate may be subjected to additional purification steps (e.g., ion exchange chromatography or immunoaffinity chromatography) to further enrich the lysate or provide a homogeneous source of the purified enzyme (see e.g., U.S. Pat. Nos. 5,292,658 and 5,418,155).

Example 14

Cartridges for loading, charging, recharging and/or filling bioluminescent novelty items An exemplary loading, recharging or charging cartridge is depicted in FIGS. 28–34. Referring first FIG. 28, a charging cartridge is shown and generally designated 1000. This charging cartridge includes a block 1002 having two cylinders, a first cylinder 1010 and a second cylinder 1012, and a plunger 1004 having a first piston 1006 and a second piston 1008. Additional chambers may be included. Also, the device may be adapted for use with the single chamber apparatus provided herein.

As shown, the block is formed with two cylinders 1010 and 1012, and the plunger is formed with two cylindrical pistons 1006 and 1008. It is to be appreciated that a triangular, rectangular, or any other geometry vessel may be substituted for either cylinder, so long as the shape of the pistons provides for insertion into the block. Additionally, for example, the plunger 1004 may be formed such that the two pistons 1006 and 1008 are separate from the other to permit the insertion of pistons 1006 and 1008 into the block 1002 at different times.

The block 1002 and plunger 1004 may be made of any material known to one of skill in the art that does not react with the components of a bioluminescence generating system. In a preferred embodiment, the block 1002 and plunger 1004 are made of a plastic material that can be readily injection molded into a selected particular shape. Suitable plastics include, but are not limited to polyvinyl chloride (PVC), or any other plastic, TEFLON, polyethylene, or any other material that is inert to components stored and dispensed from the block 1002. Alternatively, the block 1002 and plunger 1004 can be made from a metal that is machined, cast, or otherwise formed into the particular shape.

Figure 29:
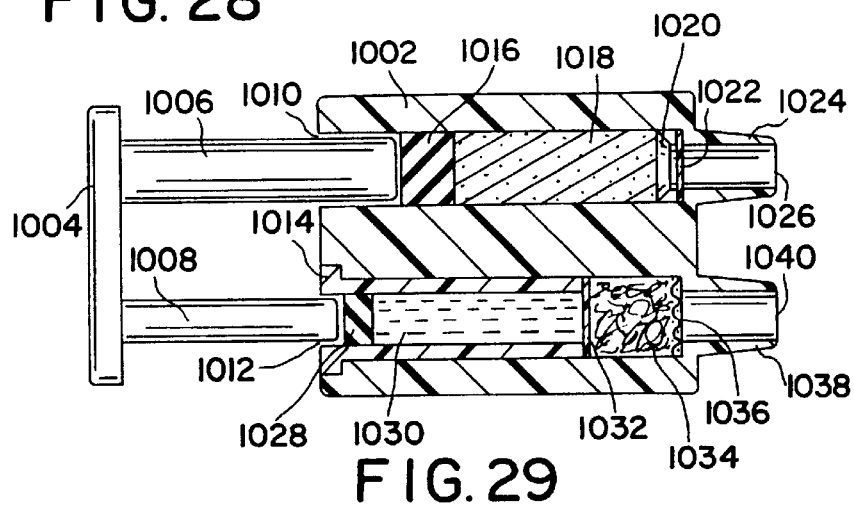
FIG. 29 is a sectional view taken on line 29—29 of FIG. 28, with the plunger in the starting position.

Referring now to FIG. 29, the first cylinder 1010 has a plug 1016 which retains, for example, dry ingredients 1018 containing one or more components of a bioluminescence generating system, preferably including a luciferase and/or luciferin and any necessary buffers and activators, e.g., ATP or $Ca^{2+}$, and more preferably a luciferase, buffers and any necessary activators, in lyophilized or other suitable form, in the cylinder 1010 and against the seal 1022. Thus, the dry or condensed ingredients 1018 are trapped within the first cylinder 1010 between the plug 1016 and the seal 1022 until the plunger 1004 and piston 1006 are forced into the first cylinder 1010. At that time, theses ingredients 1018 are forced through the funnel means 1020, thereby breaking the seal 1022, and forcing the ingredients 1018 out of the block 1002 through nozzle 1024 and out aperture 1026. The seal 1022 is preferably made of a material which is capable of being broken with only minimal pressure asserted on the plunger 1004. Such a material includes, for example, a paper, wax-covered paper, plastic sheet, foil, cellophane or any other material exhibiting the requisite properties.

The second cylinder 1012 is formed within a fluid sleeve 1014 that is inserted into the block 1002. In this way, the sleeve 1014 may be a sealed tube made from, for example, plastic, glass, or any other material that is compressible and/or breakable, thereby allowing the fluid 1030 to be forced from the sleeve 1014. The sleeve 1014 may be prefabricated and loaded with the fluid 1030 prior to insertion into the block 1002, or the fluid 1030 may be added to the sleeve 1014 once it is positioned within the block 1002, and retained therein by plug 1028.

The piston 1008 slides into the second cylinder 1012 and strikes plug 1028, advancing it into the block 1002. The advancing plug 1028 creates a fluid pressure within the sleeve 1014 which eventually breaks seal 1032 and optionally bathes the matrix material 1034 in fluid 1030. Like the seal 1022 in the first cylinder 1010, the seal 1032 in the second cylinder 1014 can be made of any material that can be broken or torn or ruptured with only minimal pressure being asserted on the plunger 1008. Such a material may be a paper, wax-covered paper, plastic sheet, foil, cellophane or any other material which exhibits the necessary characteristics.

The matrix material 1034 may be any porous material to which the bioluminescence generating component can be adsorbed, absorbed or otherwise linked, as described herein, that is non-reactive with the components of the bioluminescence generating system. When necessary, the matrix material 1034 is included and bathed in the fluid 1030 such that the component(s) of the bioluminescnce generating system affixed to the matrix material are released into the fluid 1030. As the piston is continually advanced, the fluid, containing bioluminescence generating components eluted from the matrix material, is forced through the filter 1036 and out the nozzle 1038 and aperture 1040. Filter 1036 is used to prevent the expulsion of matrix material 1034 from the second cylinder 1014. As a result, the filter 1036 may be made from a cloth or metallic weave, or any other material that will not react with the various components and compositions present within the second cylinder 1014.

It is to be appreciated, however, that the various components of the bioluminescent reaction may be distributed in different combinations between the two cylinders 1010, 1012, and the matrix material 1034. One cylinder, such as the first cylinder 1010, typically contains the dry or condensed ingredients 1018 and the second cylinder 1012 typically contains a fluid 1030 and the matrix material containing the remaining components necessary for the bioluminescent reaction. The dry or condensed ingredients may contain any combination of the components of the bioluminescence generating system, such as a luciferase and/or a luciferin, buffer salts, ATP, $Ca^{2+}$ or any other necessary activator. The fluid 1030 may be water, a buffer, an organic solvent or any other aqueous medium suitable for solubilizing or suspending one or more components of a bioluminescence generating system to be dispensed into the bioluminescent novelty item.

In a preferred embodiment, the dry ingredients 1018 include lyophilized luciferase and buffer salts in powder form, and the fluid includes an alcohol that is used to dissolve or suspend a quantity of luciferin affixed to the matrix material. Alternatively, all of the components of a bioluminescence generating system, such as the Vargula system, may be added and packaged in the first and/or second cylinders in the absence of molecular oxygen such that components are activated when combined and exposed to air.

Figure 30:
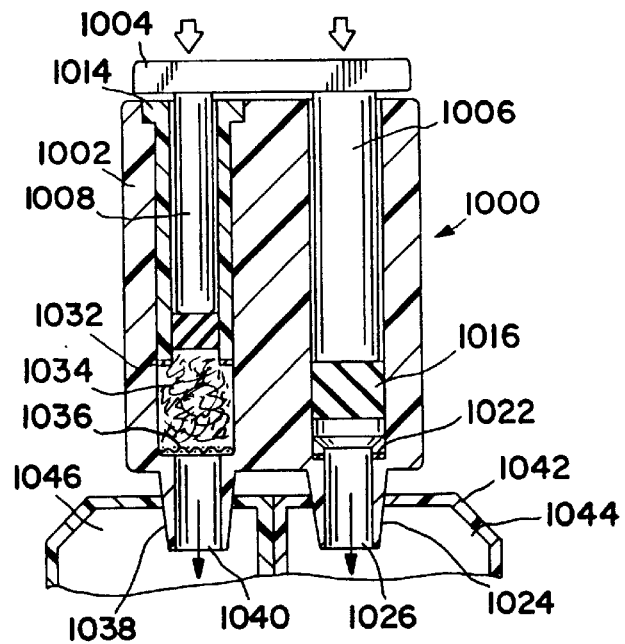
FIG. 30 is a sectional view similar to FIG. 29, showing the cartridge contents ejected into receiving chambers of a typical unit as shown in FIG. 2.

Referring now to FIG. 30, the cartridge 1000 is shown as used in conjunction with a typical bioluminescent novelty item 1042. As shown, the plunger 1004 has been pressed completely against the block 1002 causing the first piston 1006 and the second piston 1008 to be inserted completely into the block 1002. As the piston 1006 is advanced into the block 1002, the dry or condensed ingredients 1018, for example, are forced out of the first cylinder 1010, through the funnel 1020 thereby breaking the seal 1022, and out the nozzle 1024 and aperture 1026 into the chamber 1044 in novelty item 1042. Likewise, as the piston 1008 is advanced into the block 1002, the seal 1032 on the sleeve 1014 is ruptured causing the fluid 1030 to be dispensed, optionally bathing matrix material 1034. As the piston 1008 is advanced further, the fluid 1030 is forced through filter 1036, out nozzle 1038 and aperture 1040, and into chamber 1046 of novelty item 1042. In this manner, the novelty item is fully recharged with the components of a bioluminescence generating system necessary for a bioluminescent reaction, while maintaining the separation of the chemicals as required for some novelty items.

The cartridge 1000 is shown inserted into the filler holes of a typical novelty item 1042, such as those described elsewhere in this application. For example, the cartridge could be adapted to fit the numerous of the novelty items, such as the following novelty items: the filler caps 17, 19 associated with chambers 10, 12 shown in FIGS. 1 and 3; the filler caps 82, 84 shown in FIGS. 4 and 5; the filler caps 104, 106 shown in FIGS. 6, 7, and 8; and the filler caps 406, 408 on housing 466 in FIGS. 23 through 26. It should be appreciated that although several novelty items have be identified as being either chargeable or rechargeable using the cartridges disclosed herein, such identification is merely exemplary and is in no way to be intended as limiting the application of the cartridges to those particular novelty items. On the contrary, the cartridges described herein may be adaptable to charge, or recharge, virtually any bioluminescent novelty item.

Figure 31:
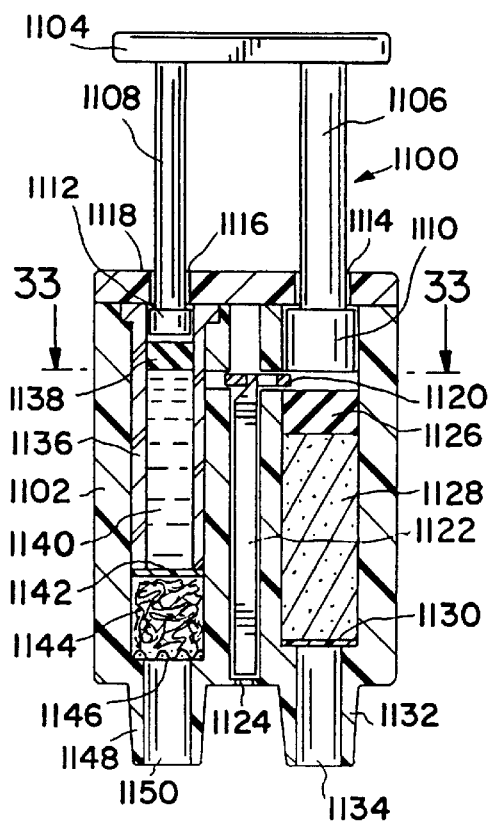
FIG. 31 is a sectional view similar to FIG. 29, showing a plunger locking device.

Referring now to FIG. 31, a second embodiment of a charging cartridge is shown and generally designated 1100. The cartridge 1100 is shaped substantially like the cartridge 1000, with the addition of a safety feature that prevents the accidental or inadvertent discharge of the cartridge when not inserted properly within a novelty item. While an accidental discharge would not be physically harmful to a human or non-human animal, such a discharge could prematurely release the bioluminescent materials. The likelihood of such an accidental discharge could, perhaps, be increased when considering the intended user of many of the novelty items, such as children.

In this exemplary embodiment, cartridge 1100 contains a block 1102 and a plunger 1104 which, like the cartridge 1000, has a first piston 1106 and a second piston 1108. Unlike the cartridge 1000, however, each of the pistons 1106 and 1108 is equipped with a piston head 1110 and 1112, respectively. These piston heads, in conjunction with cap 1118 prevent the removal of the plunger 1104 from the block 1102. As a result, the cartridge 1100 cannot be disassembled to yield direct access to the contents of the cylinders 1114 and 1116. In addition to the piston heads 1110, 1112, the cartridge 1100 is also equipped with a stop 1120 and a slide 1122 to prevent the accidental compression of the plunger 1104 into the block 1102 while the cartridge is not inserted into a novelty item. More specifically, the stop 1120 is normally positioned in the path of the first piston 1106 to prevent the advance of the first piston 1106 into the block 1102. Once the cartridge 1100 is positioned on an appropriate novelty item, the slide 1122 is automatically pressed upwards thereby moving the stop 1120 out of the path of the dry piston 1106. Once the stop 1120 is out of the way, the two pistons 1106, and 1108, may be pressed into the block 1102, thereby releasing the contents of the first cylinder 1114 and the second cylinder 1116 in the same manner as discussed above in conjunction with FIGS. 28 through 30.

Figure 32:
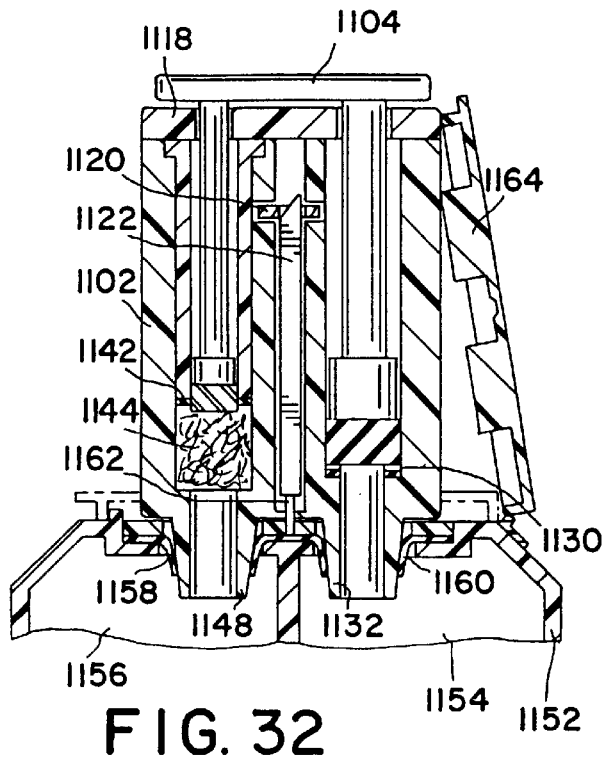
FIG. 32 is a sectional view similar to FIG. 30, showing the locking device released to allow compression of the plunger.

Referring now to FIG. 32, the cartridge 1100 is shown as used in conjunction with a properly equipped novelty item 1152. As shown, the novelty item 1152 is equipped with a pin 1162 which extends upwards from the novelty item 1152. As the cartridge 1100 is placed over the novelty item 1152, the pin 1162 forces the slide 1122 upwards thereby moving the stop 1120 from the path of piston 1106. Once piston 1106 is able to be pressed into the block, the piston 1106 and piston 1108 are forced into the block 1102. More specifically, as piston 1106 is forced into the block 1102, the piston advances plug 1126 which in turn forces the dry or condensed ingredients 1128 to break seal 1130. Once the seal 1130 is broken, the dry or condensed ingredients 1128 are further forced through nozzle 1132 and out aperture 1134, and into the first chamber 1154 of the novelty item 1152. Similarly, as the plunger is depressed, the wet piston 1108 is forced into the fluid cylinder 1116 and strikes plug 1138. As the wet piston is advanced, the plug 1138 creates a fluid pressure within the sleeve 1136, thereby rupturing the seal 1142 causing the fluid 1140 to be forced through the matrix material 1144, through filter 1146, and through nozzle 1148 and out aperture 1150 and into the second chamber 1156 in novelty item 1152.

Figure 33:
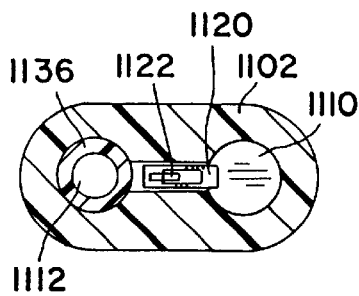
FIG. 33 is a sectional view taken along line 33—33 of FIG. 31 and showing the positioning of the locking device.

FIG. 33 provides a cross-sectional view of the cartridge 1100, showing in detail the placement of the stop 1120 and slide 1122 in relation to the dry piston head 1110. As shown, the stop 1120 extends into cylinder 1114 sufficiently to prevent the advancement of piston 1126 in cylinder 1114. It should be appreciated that while the stop 1120 is blocking the advance of only the piston 1110, that piston 1112 could be held in place in addition to, or instead of, piston 1110. Moreover, the stop 1120 and slide 1122 could be positioned anywhere in the block 1102 such that the pin 1162 could be positioned on the novelty device in an alternative location. It should also be appreciated that a spring (not shown) may be used to hold the stop 1120 in a resting position such that only with the movement of the slide 1122 can the dry piston 1106 be advanced into the block. Additionally, a spring (not shown) may be positioned to naturally urge the slide towards hole 1124 in block 1102, thereby preventing the accidental movement of the slide without the aid of a pin 1162.

In addition to the cartridges as shown above, other means may be employed to minimize the leakage of the contents of the bioluminescence generating systems in combination with the various novelty items described herein. More specifically, the novelty item 1152 may be equipped with a removable cap 1164 that is used to seal the chambers 1154 and 1156 of the novelty item 1152 to minimize the leakage of any components of the bioluminescence generating system. Further, a series of seals 1158 and 1160, or one way seal valves, can be used to prevent the escape of the components once they have been placed in the chambers of the novelty item 1152. Seal 1160 is of a type which is normally biased to a closed position to prevent the passage of material in one direction. In this application, the seal 1160 is biased closed such that any material within the chambers 1154 and 1156 is retained within the chamber. Only upon the insertion of nozzles 1132 and 1148 through the seals 1158 and 1160 is it possible for material to pass through the seal. Thus, once the nozzles 1132 and 1148 are inserted into the novelty item 1152 through the seals 1158 and 1160, the contents of the cylinders 1128 and 1140 are easily injected. Once the contents are injected, however, the nozzles are removed, and the seals 1158, 1160 return to their normal biased closed position to prevent the escape of the chemicals from the chambers 1154, 1156.

Figure 34:
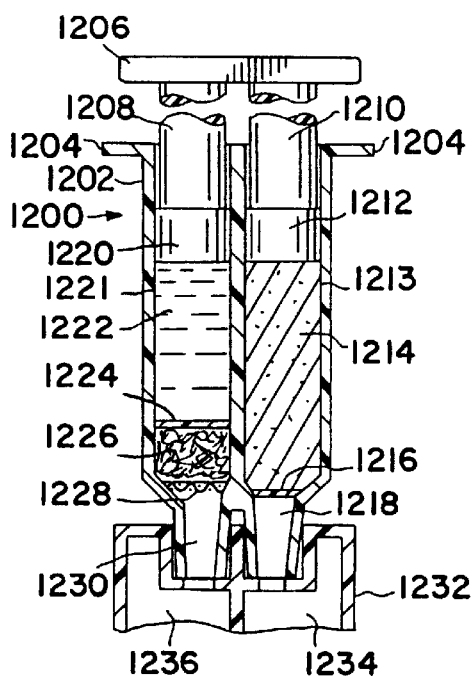
FIG. 34 is a sectional view of an alternative embodiment dual chamber refill cartridge.

In yet another alternative embodiment of a cartridge, a dispensing syringe is shown in FIG. 34 and generally designated 1200. Syringe 1200 has a body 1202 which is equipped with a circumferential flange 1204 (or a pair of tabs extending from each side of the body), and a plunger 1206. This construction provides for a one-handed operation recharging a novelty item. More specifically, by holding the body adjacent to the circumferential flange between the index finger and middle finger of a user, and using the thumb to advance the plunger 1206 into the body 1202, the entire contents of the dispensing syringe 1200 can be injected into the novelty item.

The plunger 1206 has two pistons 1210 and 1208 which are formed with plugs 1212 and 1220 respectively. These plugs 1212 and 1220 are sized to be snugly received inside the cylinders, e.g., cylinders 1213 and 1221. One cylinder, e.g., cylinder 1213, is filled with dry ingredients 1214 and held in place against the seal 1216. Like the cartridges 1000 and 1100 discussed above, as piston 1212 is advanced into cylinder 1213, the seal 1216 is ruptured allowing the expulsion of the dry ingredients 1214 out of nozzle 1218 and into chamber 1234 of novelty item 1232.

Plug 1220 is positioned in the cylinder 1221 to retain, for example, the fluid 1222 between seal 1224 and plug 1220. As with the cartridges discussed above, as piston 1208 is advanced into the body 1202, fluid pressure is created within the cylinder 1221, thereby rupturing the seal 1224. Once the seal is ruptured, the fluid is dispensed, and optionally bathes matrix material 1226 to dissolve the one or more component of the bioluminescence generating system into the fluid. As the piston 1212 is further advanced, the fluid 1222 is forced through filter 1228 and out nozzle 1230 and into chamber 1236 of novelty item 1232.

As an alternative to the nozzles 1218 and 1230, a mixing chamber (not shown) can be formed in the body 1202 or attached thereto. Such a chamber would provide for the thorough mixing of the dry ingredients 1214 and the fluid 1222, prior to introduction of the chemicals into the novelty item. Such a mixing would be advantageous where it is not feasible to keep the components of the bioluminescence generating system separate until the instant the reaction is desired, such as in a single-chambered novelty item having a single chemical input port. It is also to be appreciated that a mixing chamber can be easily formed within the cartridge 1000 and/or 1100 or attached thereto.

The charging cartridges 1000, 1100, and 1200 shown and described herein have substantially cylindrical chambers within which to store the components of the bioluminescence generating system, separately or together, in liquid or solid form. It should be appreciated, however, that any shape chamber is contemplated herein. Specifically, in cartridge 1000 and 1100 may be formed with a pair of chambers having a rectangular cross-section, or may be formed with each chamber having a semi-circular cross-section, representing one half of a cylindrical block. Virtually any shape for the block and chambers is contemplated herein, and the particular embodiments shown in FIGS. 28 through 34 are only exemplary.

In yet another alternative embodiment (not shown), the cylindrical chambers of the cartridges 1000 and 1100 are replaced by compressible tubing which are positioned within the block and filled with the necessary chemicals, but are also easily compressed to expel the chemicals within them. The compressible tubing can be made from any other material which is sufficiently rigid to contain the chemicals, such plastic, rubber or other such material, but pliable enough to allow the expulsion of the chemicals using a piston. The tubing can be formed in an accordion-shape which has pre-formed creases in the walls of the tubing, or may be formed in any manner which simplifies expulsion of the chemicals. Such a tubing construction would eliminate the need for plugs to retain the chemicals within the block, and will also simplify the manufacturing of the cartridge by eliminating the direct handling of the bioluminescent components.

As an alternative to a cartridge having a block and plunger, a cartridge may be constructed having a block made from a pliable material that allows compression of the chemical tubing or other suitable material by squeezing the sides of the block. In other words, instead of requiring a plunger having pistons which compress the chemical tubing, the block may be sealed with the chemical tubing contained inside the block, with the chemicals being expelled by squeezing the sides of the block to create the pressure necessary to rupture the chemical tubing inside.

In addition to a charging cartridge for charging and/or recharging bioluminescent novelty items, the cartridge incorporating compressible tubing can be formed to allow replacement of the compressible tubing portions within the block. More specifically, once a cartridge has been used to charge or recharge a novelty item, the compressible tubing having a fluid and at least one component of the bioluminescent reaction, and the compressible tubing having the dry ingredients, may be removed from the block, and a new set of chemical tubing may be positioned within the block. As a result, the cartridge may be repeatedly used, replacing only the chemical tubing portions. This would provide for the minimization of the costs associated with the use and repeated use of the novelty items because only the chemical tubing portions would have to be replaced, instead of discarding the entire cartridge following each use.

Since modifications will be apparent to those of skill in this art, it is intended that this invention be limited only by the scope of the appended claims.

Summary of Sequences of Representative luciferases and the reductase set forth in the Sequence Listing 1. SEQ ID NO. 1 Renilla reinformis Luciferase [U.S. Pat. No. 5,418,155]
2. SEQ ID NO. 2 *Cypridina hilgendorfii* luciferase [EP 0 387 355]
3. SEQ ID NO. 3 Modified *Luciola cruciata* Luciferase [firefly; U.S. Pat. No. 4,968,613]
4. SEQ ID NO. 4 Vargula (Cypridina) luciferase [Thompson et al. (1989) *Proc. Natl. Acad. Sci. U.S.A.* 86:6567–6571 and from JP 3-30678 Osaka
5. SEQ ID NO. 5 Apoaequorin-encoding gene [U S. Pat. No. 5,093,240, pAQ440]

6. SEQ ID NO. 6 Recombinant Aequorin AEQ1 [Prasher et al. (1987) "Sequence Comparisons of cDNAs Encoding for Aequorin Isotypes," Biochemistry 26:1326–1332]

7. SEQ ID NO. 7 Recombinant Aequorin AEQ2 [Prasher et al. (1987)]

8. SEQ ID NO. 8 Recombinant Aequorin AEQ3 [Prasher et al. (1987)]

9. SEQ ID NO. 9 Aequorin photoprotein [Charbonneau et al. (1985) "Amino Acid Sequence of the Calcium-Dependent Photoprotein Aequorin," Biochemistry 24:6762–6771]

10. SEQ ID NO. 10 Aequorin mutant with increased bioluminescence activity [U.S. Pat. No. 5,360,728; Asp 124 changed to Ser]

11. SEQ ID NO. 11 Aequorin mutant with increased bioluminescence activity [U.S. Pat. No. 5,360,728; Glu 135 changed to Ser]

12. SEQ ID NO. 12 Aequorin mutant with increased bioluminescence activity [U.S. Pat. No. 5,360,728 Gly 129 changed to Ala]

13. SEQ ID NO. 13 Recombinant apoaequorin [sold by Sealite, Sciences, Bogart, Ga. as AQUALITE®, when reconstituted to form aequorin]

14. SEQ ID NO. 14 *Vibrio fisheri* Flavin reductase [U.S. Pat. No. 5,484,723]

What is claimed is:

1. A combination, comprising:
   a) an article of manufacture; and
   b) one or more components of a bioluminescence generating system and/or a fluorescent protein, whereby the combination is a novelty item selected from among personal care items, dentifrices, soaps, body paints and powders, and bubble baths.

2. The combination of claim 1, wherein the article of manufacture is selected from among bath powders, body lotions, gels, body powders, body creams, toothpastes, mouthwashes, soaps, body paints, and cosmetics.

3. The combination of claim 1, wherein the combination comprises a luciferase.

4. The combination of claim 1, wherein the combination comprises a luciferin.

5. The combination of claim 1, wherein the combination comprises a luciferin and a luciferase.

6. The combination of claim 1 that comprises a fluorescent protein.

7. The combination of claim 6, wherein the fluorescent protein is a green fluorescent protein, a blue fluorescent protein or a phycobiliprotein.

8. The combination of claim 1 that is a cosmetic, wherein the cosmetic contains a fluorescent protein.

9. The combination of claim 1 that is for application to the nails, hair, skin or lips.

10. The combination of claim 1 that is a cosmetic.

11. The combination of claim 10, comprising a delivery vehicle that comprises least one component of the bioluminescence generating system.

12. The combination of claim 1 that is nail polish, powder or hair gel.

13. The combination of claim 11, wherein a component is a luciferase.

14. The combination of claim 11, wherein a component is a luciferin.

15. The combination of claim 11, wherein the components comprise a luciferin and a luciferase.

16. The combination of claim 11, wherein the vehicle is a liposome.

17. The combination of claim 11, wherein the vehicle is a gelatin capsule.

18. The combination of claim 11, wherein the vehicle comprises micronized particles of the component(s).

19. The combination of claim 11, wherein the vehicle is a time release vehicle.

20. The combination of claim 11, wherein the vehicle is water soluble.

21. The combination of claim 1, wherein the a component of the system is selected from among components of an insect system, a coelenterate system, a ctenophore system, a bacterial system, a mollusk system, a crustacea system, a fish system, an annelid system, and an earthworm system.

22. The combination of claim 1, wherein a component of the system is selected from among from components of Aequorea, Vargula, Renilla, Obelin, Porichthys, Aristostomias, Odontosyllis, Oplophorus, Gaussia, firefly and bacterial systems.

23. The combination of claim 1, wherein a component of the system is selected from components of *Renilla Cavarnularia*, Ptilosarcus, Stylatula, Acanthoptilum, and Parazoanthus systems.

24. The combination of claim 1, wherein a component of the system is selected Chiroteuthis, Eucleoteuthis, Onychoteuthis, Watasenia; cuttlefish, Sepiolina, Oplophorus, Sergestes, and Gnathophausia; Argyropelecus, Yarella, Diaphus, and Neoscopelus systems.

25. The combination of claim 1, wherein the bioluminescence generating system comprises a component from a coelenterate.

26. The combination of claim 10, wherein the bioluminescence generating system comprises a component from a coelenterate.

27. The combination of claim 10, wherein a component of the bioluminescence generating system is selected from among components of Aequorea, Vargula, Renilla, Obelin, Porichthys, Odontosyllis, Aristostomias, Oplophorus, Gaussia, firefly, bacterial, Mnemiopsis, Beroe Gonadostomias, Gaussia, Halisturia, Vampire squid, Glyphus, Mycotophid, Vinciguerria, Howella, Florenciella, Chaudiodus, Melanocostus Sea Pens, mollusc, mushroom, fish, insect, ctenophore and annelid systems.

28. The combination of claim 10, wherein a component of the system is selected from components of *Renilla Cavarnularia*, Ptilosarcus, Stylatula, Acanthoptilum, and Parazoanthus systems.

29. The combination of claim 10, wherein the a component of the system is selected from components of Chiroteuthis, Eucleoteuthis, Onychoteuthis, Watasenia; cuttlefish, Sepiolina, Oplophorus, Sergestes, and Gnathophausia; Argyropelecus, Yarella, Diaphus, and Neoscopelus systems.

30. The combination of claim 10, wherein a component of the system is selected from among components of Aequorea, Vargula, Renilla, Obelin, Porichthys, Aristostomias, Odontosyllis, Oplophorus, Gaussia, firefly and bacterial systems.

\* \* \* \* \*

UNITED STATES PATENT AND TRADEMARK OFFICE
CERTIFICATE OF CORRECTION

PATENT NO. : 6,113,886
DATED : September 5, 2000
INVENTOR(S) : Bryan

It is certified that error appears in the above-identified patent and that said Letters Patent is hereby corrected as shown below:

IN THE RELATED U.S. APPLICATION DATA [60]:
At lines 2 and 3, please replace "which is" with —and—.

IN THE REFERENCES CITED [56]:
Please add the following to the FOREIGN PATENT DOCUMENTS:
0025350     09/05/80     EP A2
0194102     09/10/86     EP A2
0226979     07/01/87     EP A2

Please add the following to OTHER PUBLICATIONS:
"AquaLite®. A calcium-triggered photoprotein," SeaLite Sciences Technical Report No. 3 (1994)
Anctil et al., Mechanism of photoinactivation and re-activatioon in the bioluminescence system of the ctenophore Mnemiopsis, Biochem. J. 22(1): 269-272 (1984)
Apt et al., Evolution of phycobiliproteins, J. Mol. Biol. 248: 79-96 (1995)
Assil et al., Sustained release of the antimetabolite cytarabine in the eye multivesicular liposomes, Arch. Opthalmol. 105: 400-403 (1987)

At column 31, line 11, please delete "protein";
at column 45, line 5, please replace "Chem et al." with —Chen et al.—;
at column 65, line 51, after "plastic" please replace "," with —.—;
at column 66, line 29, please replace "reacton" with —reaction—;
at column 69, line 2, please replace "absortion" with —absorption—;
at column 69, line 17, please replace "sutiable" with —suitable—;
at column 71, line 33, please replace "bioluiminescence" with —bioluminescence—.

Signed and Sealed this

Twenty-second Day of May, 2001

*Attest:*

NICHOLAS P. GODICI

*Attesting Officer*     *Acting Director of the United States Patent and Trademark Office*